(12) United States Patent
McNally et al.

(10) Patent No.: US 9,251,310 B2
(45) Date of Patent: Feb. 2, 2016

(54) THERAPY MANAGEMENT SYSTEM AND METHOD FOR PERITONEAL DIALYSIS

(75) Inventors: Larry McNally, Mundelein, IL (US); Andy Vecsey, Tampa, FL (US); Rich DeLaCruz, Indian Rocks Beach, FL (US); Salim Mujais, Northbrook, IL (US); Like Coman, Chicago, IL (US); Richard Marritt, Deerfield, IL (US); Catherine Firanek, Villa Park, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 460 days.

(21) Appl. No.: 13/024,990

(22) Filed: Feb. 10, 2011

(65) Prior Publication Data

US 2011/0131058 A1    Jun. 2, 2011

Related U.S. Application Data

(63) Continuation of application No. 10/376,022, filed on Feb. 28, 2003, now Pat. No. 7,890,341, which is a continuation-in-part of application No. 10/315,435, filed on Dec. 9, 2002, now abandoned.

(51) Int. Cl.
*G06Q 10/00* (2012.01)
*G06F 19/00* (2011.01)
(Continued)

(52) U.S. Cl.
CPC ............ *G06F 19/322* (2013.01); *G06F 19/327* (2013.01); *G06F 19/3425* (2013.01);
(Continued)

(58) Field of Classification Search
CPC ....... G06Q 50/22; G06Q 50/24; G06Q 10/00; G06F 19/3418; G06F 19/345
See application file for complete search history.

(56) References Cited

U.S. PATENT DOCUMENTS 4,096,859 A    6/1978    Agarwal et al.
RE31,302 E    7/1983    Stambler
(Continued)

FOREIGN PATENT DOCUMENTS

WO    WO02/07796    1/2002
WO    WO02/07797    1/2002

OTHER PUBLICATIONS

PAC-Xtra; Automated Peritoneal Dialysis Cycler Operator's Manual; 157-1241-999; Jan. 1991; 5C4402/5C4403; Baxter Healthcare Corporation; Copyright 1991.
(Continued)

*Primary Examiner* — Michelle L Le
(74) *Attorney, Agent, or Firm* — K&L Gates LLP

(57) ABSTRACT

A method for organizing care for a patient undergoing a peritoneal dialysis therapy under a system including at least one display device, at least one memory device, at least one processor and at least one peritoneal dialysis instrument for performing the peritoneal dialysis therapy, the method comprising: organizing information for presentation in a plurality of screens using the at least one display device, the at least one memory device, and the at least one processor, wherein each screen presents information pertinent to a particular aspect of the peritoneal dialysis therapy; and displaying in the plurality of screens information about the patient's prescription for the peritoneal dialysis therapy, information about medication the patient is taking in connection with the peritoneal dialysis therapy, and information about the patient's compliance with the peritoneal dialysis therapy.

26 Claims, 90 Drawing Sheets

(51) Int. Cl.
  *G06Q 40/08* (2012.01)
  *G06Q 50/22* (2012.01)
  *G06Q 50/24* (2012.01)

(52) U.S. Cl.
  CPC ............... *G06Q40/08* (2013.01); *G06Q 50/22* (2013.01); *G06Q 50/24* (2013.01); *G06F 19/3418* (2013.01); *G06F 19/3481* (2013.01)

(56) References Cited

U.S. PATENT DOCUMENTS

| | | |
|---|---|---|
| 4,428,381 A | 1/1984 | Hepp |
| 4,990,258 A | 2/1991 | Bjare et al. |
| 5,265,010 A | 11/1993 | Evans-Paganelli et al. |
| 5,267,314 A | 11/1993 | Stambler |
| 5,276,611 A | 1/1994 | Ghiraldi |
| 5,352,364 A | 10/1994 | Kruger et al. |
| 5,401,238 A | 3/1995 | Pirazzoli |
| 5,486,999 A | 1/1996 | Mebane |
| 5,517,405 A | 5/1996 | McAndrew et al. |
| 5,524,073 A | 6/1996 | Stambler |
| 5,555,303 A | 9/1996 | Stambler |
| 5,558,638 A * | 9/1996 | Evers et al. ............. 604/66 |
| 5,609,770 A | 3/1997 | Zimmerman et al. |
| 5,618,441 A | 4/1997 | Rosa et al. |
| 5,620,608 A | 4/1997 | Rosa et al. |
| 5,643,201 A | 7/1997 | Peabody et al. |
| 5,646,998 A | 7/1997 | Stambler |
| 5,664,109 A | 9/1997 | Johnson et al. |
| 5,672,154 A | 9/1997 | Sillen et al. |
| 5,687,716 A | 11/1997 | Kaufmann et al. |
| 5,713,350 A | 2/1998 | Yokota et al. |
| 5,737,539 A | 4/1998 | Edelson et al. |
| 5,744,027 A | 4/1998 | Connell et al. |
| 5,758,095 A | 5/1998 | Albaum et al. |
| 5,772,585 A | 6/1998 | Lavin et al. |
| 5,785,650 A | 7/1998 | Akasaka et al. |
| 5,788,851 A | 8/1998 | Kenley et al. |
| 5,793,302 A | 8/1998 | Stambler |
| 5,823,949 A | 10/1998 | Goltra |
| 5,832,448 A | 11/1998 | Brown |
| 5,833,599 A | 11/1998 | Schrier et al. |
| 5,845,253 A | 12/1998 | Rensimer et al. |
| 5,845,255 A | 12/1998 | Mayaud |
| 5,857,967 A | 1/1999 | Frid et al. |
| 5,879,163 A | 3/1999 | Brown et al. |
| 5,883,370 A | 3/1999 | Walker et al. |
| 5,897,493 A | 4/1999 | Brown |
| 5,899,855 A | 5/1999 | Brown |
| 5,911,133 A | 6/1999 | Soble |
| 5,918,603 A | 7/1999 | Brown |
| 5,924,074 A | 7/1999 | Evans |
| 5,933,136 A | 8/1999 | Brown |
| 5,936,541 A | 8/1999 | Stambler |
| 5,937,387 A | 8/1999 | Summerell et al. |
| 5,938,938 A | 8/1999 | Bosetto et al. |
| 5,951,300 A | 9/1999 | Brown |
| 5,959,529 A | 9/1999 | Kail, IV |
| 5,960,403 A | 9/1999 | Brown |
| 5,964,700 A | 10/1999 | Tallman et al. |
| 5,974,148 A | 10/1999 | Stambler |
| 5,974,389 A | 10/1999 | Clark et al. |
| 5,987,519 A | 11/1999 | Peifer et al. |
| 5,991,731 A | 11/1999 | Colon et al. |
| 5,997,476 A | 12/1999 | Brown |
| 6,014,626 A | 1/2000 | Cohen |
| 6,014,631 A | 1/2000 | Teagarden et al. |
| 6,024,699 A | 2/2000 | Surwit et al. |
| 6,026,363 A | 2/2000 | Shepard |
| 6,032,119 A | 2/2000 | Brown et al. |
| 6,050,940 A | 4/2000 | Braun et al. |
| 6,067,524 A | 5/2000 | Byerly et al. |
| 6,074,345 A | 6/2000 | van Oostrom et al. |
| 6,076,166 A | 6/2000 | Moshfeghi et al. |
| 6,081,809 A | 6/2000 | Kumagai |
| 6,101,478 A | 8/2000 | Brown |
| 6,104,626 A | 8/2000 | Katakura et al. |
| 6,108,635 A | 8/2000 | Herren et al. |
| 6,112,224 A | 8/2000 | Peifer et al. |
| 6,122,351 A | 9/2000 | Schlueter, Jr. et al. |
| 6,154,726 A | 11/2000 | Rensimer et al. |
| 6,154,750 A | 11/2000 | Roberge et al. |
| 6,157,914 A | 12/2000 | Seto et al. |
| 6,168,563 B1 | 1/2001 | Brown |
| 6,171,237 B1 | 1/2001 | Avitall et al. |
| 6,177,940 B1 | 1/2001 | Bond et al. |
| 6,188,407 B1 | 2/2001 | Smith et al. |
| 6,192,345 B1 | 2/2001 | Chicorel |
| 6,212,424 B1 | 4/2001 | Robinson |
| 6,213,942 B1 | 4/2001 | Flach et al. |
| 6,230,142 B1 | 5/2001 | Benigno et al. |
| 6,234,964 B1 | 5/2001 | Iliff |
| 6,246,992 B1 | 6/2001 | Brown |
| 6,263,330 B1 | 7/2001 | Bessette |
| 6,269,339 B1 | 7/2001 | Silver |
| 6,272,470 B1 | 8/2001 | Teshima |
| 6,277,071 B1 | 8/2001 | Hennessy et al. |
| 6,278,999 B1 | 8/2001 | Knapp |
| 6,280,634 B1 | 8/2001 | Shah et al. |
| 6,284,131 B1 | 9/2001 | Hogard et al. |
| 6,289,316 B1 | 9/2001 | Aghili et al. |
| 6,292,783 B1 | 9/2001 | Rohler et al. |
| 6,308,171 B1 | 10/2001 | De La Huerga |
| 6,311,163 B1 | 10/2001 | Sheehan et al. |
| 6,312,378 B1 | 11/2001 | Bardy |
| 6,314,405 B1 | 11/2001 | Richardson |
| 6,315,720 B1 | 11/2001 | Williams et al. |
| 6,317,719 B1 | 11/2001 | Schrier et al. |
| 6,322,502 B1 | 11/2001 | Schoenberg et al. |
| 6,336,900 B1 | 1/2002 | Alleckson et al. |
| 6,345,268 B1 | 2/2002 | De La Huerga |
| 6,347,329 B1 | 2/2002 | Evans |
| 6,358,203 B2 | 3/2002 | Bardy |
| 6,364,834 B1 | 4/2002 | Reuss et al. |
| 6,368,273 B1 | 4/2002 | Brown |
| 6,375,614 B1 | 4/2002 | Braun et al. |
| 6,385,589 B1 | 5/2002 | Trusheim et al. |
| 6,402,691 B1 | 6/2002 | Peddicord et al. |
| 6,406,426 B1 | 6/2002 | Reuss et al. |
| 6,409,662 B1 | 6/2002 | Lloyd et al. |
| 6,416,471 B1 | 7/2002 | Kumar et al. |
| 6,434,531 B1 | 8/2002 | Lancelot et al. |
| 6,804,656 B1 * | 10/2004 | Rosenfeld et al. ............. 705/3 |
| 7,033,539 B2 | 4/2006 | Krensky et al. |
| 2001/0034614 A1 | 10/2001 | Fletcher-Haynes et al. |
| 2002/0016719 A1 * | 2/2002 | Nemeth et al. ............. 705/2 |
| 2002/0040282 A1 | 4/2002 | Bailey et al. |
| 2002/0082728 A1 | 6/2002 | Mueller et al. |
| 2002/0087361 A1 | 7/2002 | Benigno et al. |
| 2002/0128861 A1 | 9/2002 | Lau et al. |
| 2002/0128862 A1 | 9/2002 | Lau et al. |
| 2002/0132214 A1 | 9/2002 | Mattson et al. |
| 2002/0133376 A1 | 9/2002 | Fritschen et al. |
| 2002/0162778 A1 | 11/2002 | Peabody et al. |
| 2003/0083901 A1 | 5/2003 | Bosch et al. |
| 2003/0220598 A1 | 11/2003 | Busby et al. |
| 2004/0010421 A1 | 1/2004 | Mina et al. |
| 2004/0015132 A1 | 1/2004 | Brown |
| 2008/0215627 A1 | 9/2008 | Higgins et al. |

OTHER PUBLICATIONS

U.S. Appl. No. 12/885,076, filed Sep. 17, 2010, Kelly et al.
U.S. Appl. No. 13/947,771, filed Jul. 22, 2013, Yu et al.
Letter from Mexican associate regarding office action for MX/a/2007/014394 dated Mar. 12, 2013.
European office action for Application No. 11 075 130.2-1651 dated Sep. 23, 2013.
European office action for Application No. 11 075 130.2-1651 dated Oct. 6, 2014.
Extended European Search Report for European Application No. 12 17 3684, dated Sep. 25, 2015.

* cited by examiner

FIG. 7

Patient Demographic Folder for
Patient [Mitchell Interman ▼]  🔍

| Transportation | Professional Contact | Employment | Care Team |
| Insurance | Emergency Contact | Next of Kin | Additional ID |
| Personal | Address | Phone / E-mail | |

Phone | Exit | Remark
[+][−] Phone Type [▼] [Home]

E-mail Address | Remark
[+][−] E-mail Type [▼] [Home]

[New] [Delete] [Save] [Reset] [<<Back] [Next>>] [Close]

File Patient Tools Wizards Window Help

Clinical Encounter (06/02/2001,Denise Albertson for Dr. Dr. Orlando Callino)

Patient [Curtis Meridian] [▶] [🔍] Date [6/02/2001] [▶] Edit date/Clinician

| Encounter Summary | Renal Disease | System Review | Physical Assessment |

- Renal Disease History
- Medications
- Allergies
- System Review
- Medical History
- Surgical History
- Family/Social History
- Hypertention: Maternal:
- Physical Assessment
- Problems and Plans General Category:

[New] [Delete] [Save] [Reset] [Print] [Close]

```
Welcome to the Patient Transfer Wizard                    [_][□][X]

Click Next to Continue
              ◇  Import Patient Data    ○
              ◇  Export Patient Data    ⊙

[ < Back ] [ Next > ] [ Cancel ]
```

```
Welcome to the Patient Transfer Wizard                    [_][□][X]

Enter the path for the exported patient(s) 'Rssxfer.db' file.
        Enter your password and click Next to continue.

File Path  [                    ]  [...]

Password   [*****]
        Verify Password  [*****]

[ < Back ] [ Next > ] [ Cancel ]
```

```
Welcome to the Patient Transfer Wizard                    [_][□][X]

Select the patient(s) you wish to export. Click finish to export patient(s).
              Patient List              Selected Patients
           Adams, Andrew       [🔍]    Anderson, Annie
           Bond, John          [▶▶]
           Brown, Bryan        [▶]
           CAPD, Andrew
           Casterllo, Carmen   [◀]
           CCPD, Cecil         [◀◀]
           Dayton, Doris

[ < Back ] [ Finish ] [ Cancel ]
```

FIG. 17

| Diagnosis Code Maintenance | | | | | | | | | | | — ☐ X |
|---|---|---|---|---|---|---|---|---|---|---|---|
| Filter: [                          ] | | | | | | | Show Inactive ☑ | | | | |
| All | Primary | Detailed | Co-Morbid | Discharge | | | | | | | |
| Active | Code | Description | | | Registry | Analysis | Pri | Det | Co-M | Dis | |
| ☑ | 401 | Hypertension | | | | | ☐ | ☐ | ☑ | ☐ | |
| ☑ | 401.0 | Hypertension Malignant | | | | | ☐ | ☐ | ☑ | ☐ | |
| ☑ | 401.0 | Hypertension Benign | | | | | ☐ | ☐ | ☑ | ☐ | |
| ☑ | 401.9 | Hypertension Unspecified | | | | | ☐ | ☐ | ☑ | ☐ | |
| ☑ | 403 | Hypertensive renal disease | | | | | ☑ | ☐ | ☐ | ☐ | |
| ☑ | 403.0 | Hypertensive renal disease, Malignant | | | 70 | 403 | ☐ | ☑ | ☐ | ☐ | |
| ☑ | 403.1 | Hypertensive renal disease, Benign | | | | | ☐ | ☑ | ☐ | ☐ | |
| ☑ | 403.9 | Hypertensive renal disease, Unspecified | | | | | ☐ | ☑ | ☐ | ☐ | |
| ☑ | 404 | Hypertensive heart and renal disease | | | | | ☑ | ☐ | ☐ | ☐ | |
| ☑ | 404.0 | Hypertensive heart and renal disease, Malignant | | | | | ☐ | ☑ | ☐ | ☐ | |
| ☑ | 404.1 | Hypertensive heart and renal disease, Unspecified | | | | | ☐ | ☑ | ☐ | ☐ | |
| ☑ | 404.9 | Hypertensive heart and renal disease, Unspecified | | | | | ☐ | ☑ | ☐ | ☐ | |
| ☑ | 405 | Secondary hypertension | | | | | ☐ | ☐ | ☑ | ☐ | |
| ☑ | 405.0 | Secondary hypertension, Malignant | | | | | ☐ | ☐ | ☑ | ☐ | |

[ New ] [ Delete ] [ Save ] [ Reset ]       [ Import.. ]       [ Close ]

| Diagnosis Code Maintenance | | | | | | | | | | | — ☐ X |
|---|---|---|---|---|---|---|---|---|---|---|---|
| Filter: [                          ] | | | | | | | Show Inactive ☑ | | | | |
| All | Primary | Detailed | Co-Morbid | Discharge | | | | | | | |
| Active | Code | Description | | | Registry | Analysis | Pri | Det | Co-M | Dis | |
| ☑ | 403 | Hypertensive renal disease | | | 70 | 403 | ☑ | ☐ | ☐ | ☐ | |
| ☑ | 404 | Hypertensive heart and renal disease | | | 70 | 403 | ☑ | ☐ | ☐ | ☐ | |

[ New ] [ Delete ] [ Save ] [ Reset ]       [ Import.. ]       [ Close ]

Clinical History Folder — □ ×

Name: Integra, Angela

Lab Results

Serum Chemistries

| | BUN | Creatinine | Glucose | Sodium | Potassium | Chloride | CO2 | Calcium | Phosphate | Magnesium |
|---|---|---|---|---|---|---|---|---|---|---|
| units | mg | mg | mg | mg | mg | mg | mg | mg | mg | mg |
| ref range | 140-150 | 140-150 | | 100-170 | 140-150 | 140-150 | | | | |
| 8/10/2002 | 149.3 | 148.6 | 147.9 | 147.2 | 146.5 | 145.8 | 145.1 | 144.4 | 143.7 | 149.3 |
| 8/17/2002 | 146.8 | 146.1 | 145.4 | 144.7 | 144.0 | 143.3 | 142.9 | 141.9 | 141.2 | 146.4 |
| 8/24/2002 | 147.8 | 147.1 | 146.4 | 145.0 | 145.0 | 144.3 | 143.6 | 142.9 | 142.2 | 147.4 |

☐ Show Detail

[New] [Delete] [Save] [Reset]          [Close]

FIG. 21

Patient Demographic Folder

Name: Integra, Angela

| Facility | Care Team |
| --- | --- |

| Staff Job Type | Staff Person | Start Date | End Date |
| --- | --- | --- | --- |
| PRIMARY Physician | Dr. Strangelove | 11/13/2000 | |
| HOME CARE Physician | Dr. B.J. Hornicut | 11/13/2000 | |
| PRIMARY Nurse | Margaret Houlihan | 5/9/2000 | |
| Nurse | Alyssa Ogawa | 11/13/2000 | |
| Nurse | Tom Parris | 6/19/2000 | |
| | | 2/5/2000 | |

Staff Job Type: PRIMARY Physician ▼ [+]
Staff Person: Dr. Strangelove ▼

Start Date: Nov. 13, 2000
End Date:

| Phone | Ext. | Category | Remark |
| --- | --- | --- | --- |
| 813-555-1212 | | Home | after 6:00PM |
| 813-999-1234 | | Cell | |

[New] [Delete] [Save] [Reset]

☐ Include History

[Close]

FIG. 22

Clinical History for Patient

Patient:

| Medical/Surgical History | Family/Social History | Hospitalizations | Emergency Dept. Visits |
|---|---|---|---|
| Medications | Allergies | Labs | Diagnostics |

| | Start Date | Category | Drug | Maint Dose | Units | Route | Frequent. |
|---|---|---|---|---|---|---|---|
| – | | A2 Receptor Blockers | Acebutolol | 400.00 mg | | Oral | Twice |

Copy From | Medications Maint. | Prescriptions

Category: A2 Receptor Blockers
Drug: Acebutolol
Template: config 1
Load Dose: 500.00  Maint. Dose: 400.00  Units: mg
Route: Oral
Frequency: Twice per  Period  Day(s)
Ordered By:  Start Date Refills: 
PRN ☑
Reason:
Instructions:
Follow Up:
Stop Date:

Treatment ☑

Allergies:

New | Delete | Save | Reset

Close

FIG. 23

Medication Maintenance

| Medication Category | Medication | Medication to Category | Medication Dictionary |

Category: A2 Receptor Blockers

| Description | Medication | Route |
|---|---|---|
| Acebutolol | 1289 | 1250 |
| Acebutolol | | |

Config 1
Config 2

Description: Acebutolol
Category: A2 Receptor Blockers
Medication: Acebutolol
Load Dose: 500.00   Maint. Dose: 400.00   Units: mg
Route: Oral
Frequency: Twice per   Period: Day(s)
PRN ☑   Treatment ☑   Duration: 5

Config 1

Delete   Save   Reset

New   Close

FIG. 29

File  Patient  ProCard  Window  Bill  Help

Exit  Patient  Compliance  Demograph  Clinical Care  Planned PD Rx  Patient Wiz  Staff Wiz  Reports  Print Screen Welcome to the PD Prescription Wizard for Anderson, Annie Navigation
- Modes/Ordered By
- Therapy Parameters
- *Nurse's Menu*
- Solutions/Manual Exchg.
- Make Adjustments
- Prompts/Special Fields
- Additional Rx Information
- Supply Chain Nurse's Menu Min. Drain Vol. [    ]

Smart Dwells:       ⦿ Yes    ○ No
Heater Bag Empty:   ○ Yes    ⦿ No
Tidal Full Drains:  ○ Yes    ⦿ No
Language:           [English ▼]
Flush:              ⦿ Yes    ○ No
Program Locked:     ○ Yes    ⦿ No Calculated
- Cycles.        [ 0 ]
- Dwell Time.    [08.27] (hrs./min.)
- Tidal Volume.  [ 150 ] ml
- UF per Cycle.  [ 0 ] ml

[Import Rx from ADEQUEST]

[<<Back]  [Next>>]  [Finish]  [Cancel]

File  Patient  ProCard  Window  Bill  Help

Exit  Patient  Compliance  Demograph  Clinical  Care Planned  PD Rx  Patient W/c  Staff W/c  Reports  Print Screen  Reminders Welcome to the PD Prescription Wizard for Anderson, Annie Navigation
- Modes/Ordered By
- Therapy Parameters
- Nurse's Menu
- Solutions/Manual Exchg.
- Make Adjustments
- Prompts/Special Fields
- Additional Rx Information
- Supply Chain Additional Rx Information

| | Pre Therapy: | Post Therapy: |
|---|---|---|
| Blood Pressure: | [ ] | [ ] / [ ] |
| Dry Weight: | 69.8 | [ ] |
| Pulse: | [ ] | [ ] |
| Temperature: | [ ] | [ ] |
| Blood Sugar: | [ ] | [ ] mg/dl |
| Urine Volume: | [ ] ml | |
| UF Goal: | 0 ml | |

Calculated
- Cycles: 0
- Dwell Time: 08.27 (hrs./min.)
- Tidal Volume: 150 ml
- UF per Cycle: 0 ml Import Rx from ADEQUEST    Back    Next    Finish    Cancel

File Patient Tolls Wizards Window Help

Exit Patient Compliance Demograph Clinical Care Planned PD Rx Patient Wiz Staff Wiz Reports Print Screen Reminders Clinical Encounter (07/26/2002,DR4,CKD for Dr. DR1,CKD)

Patient: BF2,CKD    Date: 7/26/2002 - DR4    To Do

| Encounter Summary | Renal Disease | System Review | Physical Assessment |

Renal Disease History
Change in Micturition: Nocturia Yes; Urinary Retention: No; Proteinuria:Yes; Nausea ; Yes

Medications
Analgesic-Migraine: Almotriptan

Allergies
PCN

System Review
Skin: Pruritis; Eyes: Change(s) in vision; Respiratory and Cardiovascular: Edema: Gastrointestinal: Nausea, Vomiting

Medical History
Ischemic Heart Disease; 1992: Arrythymias and Conduction Problems: 1992; Hypertension: 1988

Surgical History
Appendectomy 1960

Surgical History
Hypertension: Maternal: Coronary Artery Disease

Physical Assessment
General Appearance/
Unknown: Normal=Yes: Respiratory/Inspection: Thorax AP Diameter. Cardiac PMI Displaced Laterally= Yes Cardiac/Murmurs: Diastolic Murmur=Yes, Systolic

Problems and Plans
General Category:
Glomerulonephritis
Specific Diagnosis: Dense deposit disease, MPGN type 2

[New] [Delete] [Save] [Reset] [Print/Export] [Close]

File Patient Tolls Wizards Window Help

Exit  Patient  Demograph  History  Encounter  CKD path  Pathway  Patient Wiz

Care Pathways for Patient Curtis Meridian
Patient [Curtis Meridian]

| Access Planning | Dialysis Initiation | Transplant |

| Educational Assessment | CKD Education | Modality |

Dialysis Modality
Patient Choice
[APD ▼]   Date [6/12/2002 ▼]

Physician Choice
[CAPD ▼]   Date [6/4/2002 ▼]

Nurse Choice
[CAPD ▼]   Date [6/4/2002 ▼]

Final Choice
[CAPD ▼]   Date [6/12/2002 ▼]

If patient choice discordant with final choice reason:
☑ Patient changed mind
☑ Family changed mind
☑ Family Situation Changed
☑ Physician Driven Choice
☑ Changes in Patient Health Status
☑ Modality Selected was not Available Modality Choice ☑

Eligibility Evaluation

[New]  [Delete]  [Save]  [Reset]  [Close]

File Patient Tolls Wizards Window Help

Exit  Patient  Demograph  History  Encounter  CKD path  Pathway  Patient Wiz

Care Pathways for Patient Curtis Meridian

Patient  Curtis Meridian

| Educational Assessment | CKD Education | Modality |

| Access Planning | Dialysis Initiation | Transplant |

Transplant Coordinator  Rick Jaworski
Transplant Center  BARNES CLINIC

☑ Kidney          ☑ Pancreas          ☐ Heart          ☐ Liver
☑ Transplant Referral Submitted          Date 7/16/2002
☐ On Cadaver Wait List                   Date
☐ LRD Work Initiated                     Date Date of last annual evaluation 12/30/2001    Date on waiting list 12/16/2001

Initial Workup
☐ Medical/ Surgical Evaluation Completed    Date
☑ Lab Test Completed                         Date 7/16/2002
☐ Imaging Completed                          Date
☐ Tissue Typing Completed                    Date New        Delete        Save        Reset        Close To Do

FIG. 61a

| Test | Care Pathway Assignments ||||||
|---|---|---|---|---|---|---|
| | Renal Disease | Anemia | Anemia Therapy Profile | Diabetes Mellitus | Mineral Metabolism | Lipid Disorders |
| BUN | X | | | X | | |
| Creatinine | X | | | X | | |
| Sodium | X | | | | | |
| Potassium | X | | | | | |
| Chloride | X | | | | | |
| CO2 | X | | | | | |
| Calcium | X | | | | X | |
| Phosphorus | X | | | | X | |
| Magnesium | X | | | | | |
| Uric Acid | X | | | | | |
| Total protein | X | | | | | |
| Albumin | X | | | | | |
| Globulin | X | | | | | |
| Anion gap | X | | | | | |
| Corrected calcium | X | | | | | |
| Total bilirubin | | | | | | |
| ALT | | | | | | |
| AST | | | | | | |
| Alkaline Phosphatase | | | | | X | |
| Total cholesterol | | | | | | X |
| LDL | | | | | | X |
| HDL | | | | | | X |
| Triglycerides | | | | | | X |
| Total cholesterol/HDL ratio | | | | | | X |
| LDL/HDL ratio | | | | | | X |
| Total volume | X | | | | | |
| Total creatinine | X | | | | | |
| Creatinine concentration | X | | | | | |
| Total protein | X | | | | | |
| Protein concentration | X | | | | | |
| Total urea | X | | | | | |
| Urea concentration | X | | | | | |
| Creatinine clearance | X | | | | | |
| Color | X | | | | | |
| Specific gravity | X | | | | | |
| pH | X | | | | | |
| Protein | X | | | | | |
| Glucose | X | | | X | | |
| Nitrites | X | | | | | |
| Leukocyte esterase | X | | | | | |
| Urobilinogen | X | | | | | |
| Bilirubin | X | | | | | |
| Keotones | X | | | | | |
| WBC | X | | | | | |
| RBC | X | | | | | |
| Casts | X | | | | | |
| Crystals | X | | | | | |
| Yeast | | | | | | |
| Bacteria | X | | | | | |

FIG. 61b

| Care Pathway Assignments | | | | | | |
|---|---|---|---|---|---|---|
| Test | Renal Disease | Anemia | Anemia Therapy Profile | Diabetes Melltus | Mineral Metabolism | Lipid Disorders |
| Hemoglobin | | X | X | | | |
| Hematocrit | | X | X | | | |
| RBC Count | | X | | | | |
| MCV | | X | | | | |
| MCH | | X | | | | |
| MCHC | | X | | | | |
| WBC count | | X | | | | |
| Platelet count | | X | | | | |
| Reticulocyte count | | X | | | | |
| Iron | | X | X | | | |
| TIBC | | X | X | | | |
| Ferritin | | X | X | | | |
| Transferrin Saturation | | X | X | | | |
| HIV | | | | | | |
| Hepatitis B | | | | | | |
| Hepatitis C | | | | | | |
| VDRL | | | | | | |
| ADA | | | | | | |
| Anti-ds-DNA | | | | | | |
| CH50 | | | | | | |
| C4 | | | | | | |
| ANCA | | | | | | |
| Anti-GBM | | | | | | |
| Cryoglobulin | | | | | | |
| ASO | | | | | | |
| ADNaseB | | | | | | |
| CRP | | | | | | |
| HbA1C | | | | X | | |
| Microalbumin | | | | X | | |
| Calcium/Phosphorus Product | | | | | X | |
| Intact PTH | | | | | X | |
| 1,25 Vitamin D | | | | | X | |
| Cap | | | | | X | |
| CIP | | | | | X | |
| Erythropoietin level | | | X | | | |

FIG. 61c

|  |  | Male | | Female | | |
| --- | --- | --- | --- | --- | --- | --- |
| Test | Standard Units | Low | High | Low | High | Standard Text Ref Range |
| BUN | mg/dL | 5.0 | 20.0 | 5.0 | 20.0 | |
| Creatinine | mg/dL | 0.6 | 1.3 | 0.5 | 1.0 | |
| Sodium | mEq/L | 136.0 | 145.0 | 136.0 | 145.0 | |
| Potassium | mEq/L | 3.5 | 5.1 | 3.5 | 5.1 | |
| Chloride | mmol/L | 95.0 | 108.0 | 95.0 | 108.0 | |
| CO2 | mmol/L | 20.0 | 32.0 | 20.0 | 32.0 | |
| Calcium | mg/dL | 8.5 | 10.3 | 8.5 | 10.3 | |
| Phosphorus | mg/dL | 2.5 | 4.5 | 2.5 | 4.5 | |
| Magnesium | mmol/L | 0.6 | 1.0 | 0.6 | 1.0 | |
| Uric Acid | mg/dL | 4.0 | 8.5 | 2.7 | 7.5 | |
| Total protein | g/dL | 6.0 | 8.5 | 6.0 | 8.5 | |
| Albumin | g/dL | 3.5 | 5.0 | 3.5 | 5.0 | |
| Globulin | g/dL | | | | | |
| Anion gap | mEq/L | | | | | |
| Corrected calcium | mg/dL | | | | | |
| Total bilirubin | mg/dL | | | | | <=1.3 |
| ALT | U/L | 7.0 | 52.0 | 7.0 | 52.0 | |
| AST | U/L | 13.0 | 39.0 | 13.0 | 39.0 | |
| Alkaline Phosphatase | U/L | 31.0 | 104.0 | 31.0 | 104.0 | |
| Total cholesterol | mg/dL | | | | | |
| LDL | mg/dL | | | | | |
| HDL | mg/dL | | | | | |
| Triglycerides | mg/dL | | | | | |
| Total cholesterol/HDL ratio | | | | | | |
| LDL/HDL ratio | | | | | | |
| Total volume | mL | | | | | |
| Total creatinine | mg/volume | | | | | |
| Creatinine concentration | mg/volume | | | | | |
| Total protein | mg/volume | | | | | <=150mg/day |
| Protein concentration | mg/dL | | | | | |
| Total urea | mg/volume | | | | | |
| Urea concentration | mg/dL | | | | | |
| Creatinine clearance | mL/min/1.73m^ | 82.0 | 125.0 | 75.0 | 115.0 | |
| Color | no units | | | | | |
| Specific gravity | no units | 1.001 | 1.035 | 1.001 | 1.035 | |
| pH | no units | 4.6 | 8.0 | 4.6 | 8.0 | |
| Protein | no units | | | | | None |
| Glucose | mg/dL | 70.0 | 125.0 | 70.0 | 125.0 | 0-Trace |
| Nitrites | no units | | | | | None |
| Leukocyte esterase | no units | | | | | Negative |
| Urobilinogen | no units | | | | | 0-Trace |
| Bilirubin | no units | | | | | None |
| Keotones | no units | | | | | None |
| WBC | no units | 0.0 | 4.0 | 0.0 | 4.0 | |
| RBC | no units | 0.0 | 3.0 | 0.0 | 3.0 | |
| Casts | no units | | | | | Rare |
| Crystals | no units | | | | | |
| Yeast | | | | | | None |
| Bacteria | no units | | | | | None |

FIG. 61d

| Test | Standard Units | Male Low | Male High | Female Low | Female High | Standard Text Ref Range |
|---|---|---|---|---|---|---|
| | | | | | | None |
| Hemoglobin | g/dL | 13.8 | 17.2 | 12.0 | 15.6 | |
| Hematocrit | % | 41.0 | 50.0 | 35.0 | 46.0 | |
| RBC Count | 10^6/uL | 4.4 | 5.8 | 3.9 | 5.2 | |
| MCV | fL | 78.0 | 102.0 | 78.0 | 102.0 | |
| MCH | pg | 27.0 | 33.0 | 27.0 | 33.0 | |
| MCHC | g/L | 32.0 | 36.0 | 32.0 | 36.0 | |
| WBC count | X10^3/uL | 3.8 | 10.0 | 32.0 | 36.0 | |
| Platelet count | X10^3/uL | 130.0 | 400.0 | 130.0 | 400.0 | |
| Reticulocyte count | % of RBC's | 0.5 | 2.3 | 0.5 | 2.3 | |
| Iron | ug/dL | 25.0 | 170.0 | 25.0 | 170.0 | |
| TIBC | ug/dL | 200 | 450 | 200 | 450 | |
| Ferritin | ng/dL | 18.0 | 350.0 | 18.0 | 350.0 | |
| Transferrin Saturation | % | 12 | 57 | 12 | 57 | |
| HIV | | | | | | Negative |
| Hepatitis B | | | | | | Negative |
| Hepatitis C | | | | | | Negative |
| VDRL | | | | | | Nonreactive |
| ANA | | | | | | Negative (<1:40) |
| Anti-ds-DNA | IU/mL | | | | | <30 |
| CH50 | U/mL | 31.0 | 66.0 | 31.0 | 66.0 | |
| C4 | mg/dL | 16.0 | 47.0 | 16.0 | 47.0 | |
| ANCA | mg/dL | 75.0 | 161.0 | 75.0 | 161.0 | Negative (<1:20) |
| Anti-GBM | | | | | | Negative (<1:20) dilution |
| Cryoglobulin | | | | | | <0.01 ppt/mL/48 hours |
| ASO | IU/mL | | | | | |
| ADNaseB | | | | | | |
| CRP | mg/dL | | | | | < 0.8 |
| HbA1C | % | 3.5 | 6.0 | 3.5 | 6.0 | |
| Microalbumin | ug/min | | | | | < 15 |
| Calcium/Phosphorus Product | mg/dL | | | | | < 60 |
| Intact PTH | pg/mL | 11.0 | 54.0 | 11.0 | 54.0 | |
| 1,25 Vitamin D | pg/mL | | | | | |
| CAP | pgm/mL | | | | | |
| CIP | pgm/mL | | | | | |
| Erythropoietin level | mU/mL | 3.0 | 19.0 | 3.0 | 19.0 | |

FIG. 61e

| Test | Standard Units | Male Low | Male High | Female Low | Female High | Standard Text Ref Range |
|---|---|---|---|---|---|---|
| BUN | mmol/L | 1.8 | 7.1 | 1.8 | 7.1 | |
| Creatinine | umol/L | 5.0 | 115.0 | 44.0 | 88.0 | |
| Sodium | mmol/L | 136.0 | 145.0 | 136.0 | 145.0 | |
| Potassium | mmol/L | 3.5 | 5.1 | 3.5 | 5.1 | |
| Chloride | mmol/L | 98.0 | 107.0 | 98.0 | 107.0 | |
| CO2 | mmol/L | | | | | |
| Calcium | mmol/L | 2.15 | 2.50 | 2.15 | 2.50 | |
| Phosphorus | mmol/L | 0.87 | 1.45 | 0.87 | 1.45 | |
| Magnesium | mmol/L | 1.5 | 2.5 | 1.5 | 2.5 | |
| Uric Acid | mmol/L | 0.24 | 0.51 | 0.16 | 0.43 | |
| Total protein | g/L | 60.0 | 85.0 | 60.0 | 85.0 | |
| Albumin | g/L | 35.0 | 50.0 | 35.0 | 50.0 | |
| Globulin | | | | | | |
| Anion gap | | | | | | |
| Corrected calcium | mmol/L | | | | | |
| Total bilirubin | mmol/L | | | | | <=22 |
| ALT | U/L | | | | | |
| AST | U/L | | | | | |
| Alkaline Phosphatase | ukat/L | 0.3 | 2.1 | 0.3 | 2.1 | |
| Total cholesterol | mmol/L | | | | | |
| LDL | mmol/L | | | | | |
| HDL | mmol/L | | | | | |
| Triglycerides | mmol/L | | | | | |
| Total cholesterol/HDL ratio | | | | | | |
| LDL/HDL ratio | | | | | | |
| Total volume | mL | | | | | |
| Total creatinine | mmol/L | | | | | |
| Creatinine concentration | | | | | | |
| Total protein | g/d | | | | | <=150mg/day |
| Protein concentration | | | | | | |
| Total urea | mmol/L | | | | | |
| Urea concentration | | | | | | |
| Creatinine clearance | mL/sec | 1.37 | 2.08 | 1.25 | 1.92 | |
| Color | | | | | | |
| Specific gravity | no units | 1.001 | 1.035 | 1.001 | 1.035 | |
| pH | no units | 4.6 | 8.0 | 4.6 | 8.0 | |
| Protein | | | | | | |
| Glucose | mmol/L | 3.9 | 5.8 | 3.9 | 5.8 | |
| Nitrites | | | | | | |
| Leukocyte esterase | | | | | | |
| Urobilinogen | | | | | | 0-Trace |
| Bilirubin | | | | | | Negative |
| Keotones | | | | | | Negative |
| WBC | | | | | | <=5 high power field |
| RBC | mmol/L | | | | | <=3 high power field |
| Casts | | | | | | |
| Crystals | | | | | | |
| Yeast | | | | | | |
| Bacteria | | | | | | |

FIG. 61f

|  |  | Male | | Female | | |
| --- | --- | --- | --- | --- | --- | --- |
| Test | Standard Units | Low | High | Low | High | Standard Text Ref Range |
| Hemoglobin | g/dL | 138 | 172 | 120 | 156 | |
| Hematocrit | | 0.41 | 0.5 | 0.35 | 0.46 | |
| RBC Count | X10^12/uL | 4.4 | 5.8 | 3.9 | 5.2 | |
| MCV | | | | | | |
| MCH | | | | | | |
| MCHC | | | | | | |
| WBC count | X10^9/L | 3.8 | 10.0 | 3.8 | 10.8 | |
| Platelet count | X10^9/L | 130.0 | 400.0 | 130.0 | 400.0 | |
| Reticulocyte count | umol/L | .005 | .023 | | | |
| Iron | umol/L | 4.0 | 30.0 | 4.0 | 30.0 | |
| TIBC | umol/L | 36 | 81 | 36 | 81 | |
| Ferritin | ug/L | 18.0 | 350.0 | 18.0 | 204.0 | |
| Transferrin Saturation | % sat | 0.12 | 0.57 | 0.12 | 0.57 | |
| HIV | 1,000,000,000/L | | | | | |
| Hepatitis B | | | | | | |
| Hepatitis C | | | | | | |
| VDRL | umol/L | | | | | |
| ANA | | | | | | Negative (<1:40) |
| Anti-ds-DNA | kIU/L | | | | | <30 |
| CH50 | kU/L | 31.0 | 66.0 | 31.0 | 66.0 | |
| C4 | g/L | 0.16 | 0.47 | 0.16 | 0.47 | |
| ANCA | g/L | .75 | 1.61 | .75 | 1.61 | Negative (<1:20) |
| Anti-GBM | | | | | | |
| Cryoglobulin | | | | | | |
| ASO | | | | | | |
| ADNaseB | | | | | | |
| CRP | mg/L | | | | | < 0.8 |
| HbA1C | | .03 | .06 | | | |
| Microalbumin | | | | | | |
| Calcium/Phosphorus Product | mmol/L | | | | | |
| Intact PTH | pmol/L | 1.2 | 5.8 | 1.2 | 5.8 | |
| 1,25 Vitamin D | | | | | | |
| CAP | | | | | | |
| CIP | | | | | | |
| Erythropoietin level | IU/L | | | | | < 25 |

FIG. 62

File Patient Tolls Wizards Window Help

Exit Patient Demograph History Encounter CKD Path Pathway Patient Wiz Reports Print Screen Help Clinical Pathways for Patient BF2,CKD Patient [BF2,CKD ▼] 🔍

| Renal Disease | Anemia | Diabetes Mellitus | Mineral Metabolism |

| Hypertension | Lipid Disorders | Nutrition | Preventative |

Vaccination
  Date
  Tetanus Booster
  Influenza Vaccine
  Pneumococcal Date
  Hepatitis B
  Series Complete ☐  [Guidelines]

Screening
  Next Due
  Colon Ca
  Pap Smear
  Mammogram
  Psa
  Ppd
  Hiv
  [Guidelines]

[New]  [Delete]  [Save]  [Reset]  [Close]

ToDo

```
File Patient Tools Wizards Window Help

Patient: [____▶]  [🔍]        [🏠 Home] [🕐 Previous] [✉ Next] [?]

Access: [_____▶]        [_ □ ×]

| Summary | Access | Infection | Non-Infection | Medications | Hospitalization |

Hospital Details
Hospital Admission:  Bayfront Medical  09/01/2002
                     Diagnosis   Asthma
                     Physician   CKO-FULLACCESS CKD

| Problem              | Presentation Date | Treatment Provider |
| Exit Site Infection  | 9/1/2002          | Patient Home       |

| Treatment History | Hospitalization |

Access Details

[New]     [Delete]     [Save]     [Reset]     [Print/Export]     [Close]
```

![Screenshot of Access Planning window with Educational Assessment and CKD Education tabs, showing Modality (HD/PD), Access Type (Native Vein), Referral Date to Surgeon, Access Procedure Completion Date (Sept. 26, 2002), Follow-Up Assessment Date, Remarks fields, and buttons: New, Delete, Save, Reset, Access Details, Close.]

| Category | Observation |
|---|---|
| Lungs | Good Volume |
| Heart | OK |
| Edema | none |
| Access Condition | NA |
| Chief Complaint | none |
| Appetite | Good |

Observation Type: ○ Equipment Check  ○ Pre-Assessment  ○ Post-Assessment  ○ Additional Tabs: Meridian Setup | Medications | Vital Signs | Lab Studies | Fluid Work Sheet | Dialyzer Reuse | Final Signoff | Observation | Realtime Completed by support on 9/28/01 at 01:32:59am
Patient access site has infections as of 9/4/02

Buttons: New | Delete | Save | Reset | New Tx | Delete Tx | Close

Menu: File Patient Tools Wizards Window Help

Home | Previous | Next
Name:  Date:

```
File Patient Tools Wizards Window Help

[Home]  [Previous]  [Next]  [?]

Patient Name: Anderson, Annie          First Treatment: 1/1/99 00:00:00
Known As: Anderson, Annie              Last Treatment: 1/20/99 23:59:59
Primary ID: Ga-01                      Calendar days: 20
Therapy Mode: CCPD IPD                 Treatments: 17

Compliance         Compliance Calendar
Status  Report      Factor                  January
  ○  □ UF Goal         25      [01][02][03][04][05][06][07][08][09][10][11] 12 13 [14][15][16][17][18] 19 20
  ⊘  □ Total Volume     5       01 02 03 04 05 06 07 08 09 10 11 12 13 14 15 16 17 [18] 19 20
  ○  □ Therapy Time     5       01 02 03 04 05 06 07 08 09 10 11 12 13 14 15 16 17 [18] 19 20
  ○  □ Dry Weight       1       01 [02][03] 04 05 06 [07][08][09][10] 11 [12][13] 14 15 [16] 17 [18] 19 20
  ⊘  □ Skipped Treatments 0     01 02 03 04 05 06 07 08 09 10 11 12 13 14 15 16 17 [18][19][20]
  ○  □ Rx Changed       0       01 02 03 04 05 06 07 08 09 10 11 12 13 14 15 16 17 [18] 19 20
  ○  □ HomeChoice PRO Messages  01 [03] 04 05 06 07 08 09 10 11 12 13 14 15 16 17 [18] 19 20
     □ Compliance Summary  5

[View Selected Reports]
  [Print Selected Reports]                      [Reselect]    [Close]

Status Legend:
 ● = OK
 ○ = Warning
 □ = Patient Access Infection Presented
```

THERAPY MANAGEMENT SYSTEM AND METHOD FOR PERITONEAL DIALYSIS

PRIORITY CLAIM

This application claims priority to and the benefit of U.S. patent application Ser. No. 10/376,022, filed Feb. 28, 2003, now U.S. Pat. No. 7,890,341, entitled "System And A Method For Providing Integrated Access Management For Peritoneal Dialysis And Hemodialysis", which is a continuation-in-part of U.S. patent application Ser. No. 10/315,435, filed Dec. 9, 2002, entitled "System And A Method For Tracking Patients Undergoing Treatment And/Or Therapy For Renal Disease", the entire contents of each of which are hereby incorporated by reference and relied upon.

BACKGROUND

The present invention generally relates to a system and method for tracking a patient. More specifically, the present invention relates to a system and a method for tracking patients throughout their therapy lifetime. Specifically, the system and the method of the present invention is particularly applicable for patients whose care and/or treatment may vary in location or types of treatment which may result from the changing conditions of the patient. More specifically, the present invention relates to a system and method for tracking patient history for renal patients from the initial diagnosis of the patient of chronic kidney disease (CKD) through a therapy lifetime of a patient, i.e. CKD, peritoneal dialysis (PD), hemodialysis (HD) and/or transplant. Further, the present invention relates to a system and a method for tracking, managing and/or summarizing information relating to PD and/or HD, including access placement, infections, medications and/or hospitalization.

It is, of course, generally known to track the history of a patient treated for a specific disease, ailment, condition, therapy, or the like. Usually, information regarding the patient is recorded by a healthcare professional, such as, a doctor, a nurse, or the like. Typically, paper or a chart is used for the doctor or nurse to input information regarding the patient during treatment and/or therapy. More recently, computers are implemented to record and to store information regarding a patient. The information may be input during a patient's visit or subsequently by office personnel, for example.

Typically, in the case of a patient suffering from renal disease, often the various therapies required by the patient throughout the lifetime of the patient are separately tracked but not otherwise combined. Often, information from previous therapies are necessary to completely ascertain and/or to accurately evaluate the patient, the history of therapy to the patient and to diagnose and/or advise further treatment or the like for the patient. To do this, information recorded on paper or the separate software systems must be entered into other databases or other software tools and/or re-entered by viewing the appropriate history of interest of a particular patient. Further consideration in the treatment or therapy which the patient is seeking through an appropriate physician, facility, or other healthcare technician, professional, or the like may then be necessary.

Currently, a patient may be assigned to a nephrologist or physician to obtain a specific treatment or therapy as that treatment or therapy relates to the condition of the patient. To assign a new physician to a patient currently requires manual re-assignment of the patient and/or the records associated with that patient to the extent that any records have been previously recorded and/or exist. The new physician, therefore, has no access to any treatment history in electronic format and that information must be printed and entered manually by the new physician. Moreover, often various codes are created for a particular therapy for a given patient. As a result, the physician or other healthcare professional must manually enter data which may not be easily updated if a new set of codes had been created.

More and more, various therapies are conducted by a patient in the home of the patient. However, limitations exist regarding the types of therapy and the extent of particular therapies that may be administered to the patient at home. These limitations are often due to the inability to collect information regarding the patient and the machine that may be administering therapy to the patient as well as limitations that may be communicated to/from a dialysis center, for example, to the patient within the home. Moreover, certain patients may receive therapy at the home and subsequent therapy at another location due to changes in condition of the patient. However, as set forth above, the information regarding the therapy is not often readily available or transferable with the patient. As a result, necessary information regarding the particular stage or condition of the patient and/or the therapy of the patient is often misunderstood or inadequately assessed.

Still further, physicians often lack the understanding necessary to treat a patient. As a result, patients are not identified, characterized or channeled into care pathways by the physician due to a lack of necessary understanding of the patient by the physician to effectively and/or accurately direct the same. Chronic Kidney Disease (CKD) care pathways are not generally accurately tracked or evaluated particularly with respect to renal disease, hypertension, anemia, CKD education, dialysis initiation, lipid disorders, diabetes mellitus, morbidities planning, and the like. Moreover, software that provides a unified clinical and encounter summary screen is not available which often results in a failure to provide tracking of a continuum of care for renal patients within a single database.

Current existing renal-related clinical software used, for example, at dialysis centers by dialysis providers, are not simple to use, are not flexible in their reporting capabilities and are not integrateable with other renal-related clinical software. As a result, use of existing software to treat dialysis patients fails to provide continuity of care and data capture relating to patient and/or the therapy of the patient. Moreover, data that is captured is not standardized making the captured data difficult to interpret and/or transferable to other healthcare providers. Non-standardized data results in inefficient data retrieval and often excess or unnecessary data that may be input or otherwise targeted. Further, the organization of the care of the patient is, therefore, sacrificed due to an inability to track consistent information regarding patient care and therapies undergone by the patient.

A need, therefore, exists for an improved integrated tool to manage patients. More specifically, a need, exists for a system and a method for managing renal patients from CKD through PD, HD to transplant throughout the different points of clinical encounter experienced by the patient.

SUMMARY

The present invention provides a system and a method for treating, tracking and/or evaluating a patient. More specifically, the present invention relates to a system and a method for electronically tracking and managing the treatment or therapy associated with a patient, particularly a patient undergoing renal therapy and providing care pathways for Chronic Kidney Disease (CKD), PD, HD and transplant.

To this end, in an embodiment of the present invention, a system is provided to track and manage information regarding a patient undergoing a plurality of therapies therapy for a disease. The system has an input means for receiving the information regarding the patient and the plurality of therapies wherein the patient receives at least one of the plurality of therapies to treat the disease wherein the information is tracked and managed for the patient for each of the plurality of therapies. The system also has means for displaying the information related to each of the plurality of therapies relating to the disease of the patient.

In an embodiment, one of the plurality of therapies relates to peritoneal dialysis.

In an embodiment, one of the plurality of therapies relates to hemodialysis.

In an embodiment, the information is input by a healthcare professional.

In an embodiment, the information is input by the patient.

In an embodiment, the system has a screen associated with the display means wherein the information includes data relating to treatment of the patient.

In an embodiment, the system has a screen associated with the display means wherein the information includes data relating to a problem associated with the patient.

In an embodiment, the system has a screen associated with the display means wherein the information includes data relating to hospital admission of the patient.

In an embodiment, the system has a screen associated with the display means wherein the information includes data relating to an implant detail of the patient.

In an embodiment, the system has a screen associated with the display means wherein the information includes data relating to a clinical assessment of the patient.

In an embodiment, the system has a screen associated with the display means wherein the information includes data relating to a dynamic assessment of the patient.

In an embodiment, the system has a screen associated with the display means wherein the information includes data relating to an infection of the patient.

In an embodiment, the system has a screen associated with the display means wherein the information includes data relating to a medication for the patient.

In an embodiment, the system has a screen associated with the display means wherein the information displayed includes data relating to planning dialysis care for the patient.

In an embodiment, the system has a screen associated with the display means wherein the information includes a compliance factor.

In an embodiment, the disease is renal disease.

In an embodiment, the therapy corresponds to at least one of chronic kidney disease, peritoneal dialysis, hemodialysis and transplant.

In an embodiment, the system has a screen associated with the display means wherein the information includes a history of medications for the patient.

In an embodiment, the system has a screen associated with the display means wherein the screen includes a treatment summary for the patient receiving one of the plurality of therapies for the disease.

In an embodiment, the system has a screen associated with the display means wherein the screen includes a treatment summary for the patient receiving one of the plurality of therapies for the disease wherein the treatment summary includes a history of treatment for the patient.

In an embodiment, the system has a screen associated with the display means wherein the screen includes a treatment summary for the patient receiving one of the plurality of therapies for the disease wherein the treatment summary includes a history of infections for the patient.

In an embodiment, the system has a screen associated with the display means wherein the screen includes a treatment summary for the patient receiving one of the plurality of therapies for the disease wherein the treatment summary includes access information for the patient.

In an embodiment, the system has a screen associated with the display means wherein the screen includes a treatment summary for the patient receiving one of the plurality of therapies for the disease wherein the treatment summary includes information relating to a center at which the patient receives one of the plurality of therapies for the disease.

In an embodiment, the system has a screen associated with the display means wherein the screen includes a treatment summary for the patient receiving one of the plurality of therapies for the disease wherein the treatment summary includes a hospitalization summary for the patient receiving one of the plurality of therapies for the disease.

In an embodiment, the input means for receiving the information is retrievable on a plurality of display screens.

In an embodiment, the system has an access tab screen on the means for displaying wherein the access tab screen displays a summary of implant details for the patient.

In an embodiment, the system has an access tab screen on the means for displaying wherein the access tab screen displays a summary of clinical assessments for the patient.

In an embodiment, the system has an access tab screen on the means for displaying wherein the access tab screen displays a summary of dynamic assessments for the patient.

In an embodiment, the system has a chronic kidney disease planning pathway for the patient.

In an embodiment, the system has a screen associated with the means for displaying wherein the screen includes information to order prescriptions for the patient.

In an embodiment, the system has a screen associated with the means for displaying wherein the screen includes hemodialysis information.

In an embodiment, the system has a screen associated with the means for displaying wherein the screen includes information for the patient to effect ordering of a prescription.

In an embodiment, the system has a screen associated with the means for displaying wherein the screen includes a peritoneal dialysis window for the patient.

In an embodiment, the system has a screen associated with the means for displaying wherein the screen relates to compliance information of the patient.

In another embodiment of the present invention, a method is provided for a user to track and manage a history of a patient undergoing one of a plurality of therapies for a disease. The method comprises the steps of inputting information into a system regarding the patient and each of the plurality of therapies; tracking the information input to the system regarding the patient and each of the plurality of therapies; and collecting data relating to the patient wherein the data relates to the plurality of therapies of the patient.

In an embodiment, one of the plurality of therapies is peritoneal dialysis.

In an embodiment, one of the plurality of therapies is hemodialysis.

In an embodiment, the method further has the step of displaying data relating to the health of the patient.

In an embodiment, the disease is renal disease.

In an embodiment, the disease is chronic kidney disease.

In an embodiment, the method further has the step of summarizing information for the patient based on the collected data.

In an embodiment, the method further has the step of identifying a medication for the patient.

In an embodiment, the method further has the step of displaying a history of medications received by the patient.

In an embodiment, the method further has the step of displaying a history of treatment of the patient.

In an embodiment, the method further has the step of displaying a history of infections of the patient.

In an embodiment, the method further has the step of displaying non-infection problems associated with the patient.

In an embodiment, the method further has the step of inputting hospitalization information regarding the patient.

In an embodiment, the method further has the step of displaying a hospitalization summary for the patient.

In an embodiment, the method further has the step of providing a plurality of display screens to display the information.

In an embodiment, the method further has the step of creating a chronic kidney disease planning pathway for the patient.

In an embodiment, the method further has the step of providing a window for the patient to effect ordering of a prescription.

In an embodiment, the method further has the step of providing a hemodialysis window to evaluate treatment of the patient.

In an embodiment, the method further has the step of providing a peritoneal dialysis window to evaluate treatment of the patient.

In an embodiment, the method further has the step of providing a peritoneal dialysis window to evaluate compliance of the patient with the treatment.

It is, therefore, an advantage of the present invention to provide a system and a method for providing care to a patient.

Another advantage of the present invention is to provide a system and a method for tracking care or therapy to a patient.

And, another advantage of the present invention is to provide a system and a method for determining care pathways for Chronic Kidney Disease.

Yet another advantage of the present invention is to provide a system and a method for accurately summarizing care, treatment and/or therapy provided to a patient.

A still further advantage of the present invention is to provide a system and a method to evaluate and/or to capture PD, HD and transplant eligibility.

Yet another advantage of the present invention is to provide a system and a method for treating a patient implementing a comprehensive integrated software that covers a continuum of care for the renal patient within a single database.

Moreover, an advantage of the present invention is to provide a system and a method for standardizing dosage templates using a medication dictionary to automatically create a medication resulting in reduced time and/or keystrokes necessary to effect creation of the medication and to improve standardization of the same.

Moreover, an advantage of the present invention is to provide a system and a method for sending a description and/or supply order electronically and securely.

A further advantage of the present invention is to provide a system and a method for creating reports regarding a patient where the reports are dynamic and are able to be modified via sorting and row and/or column placement.

A still further advantage of the present invention is to provide a system and a method for identifying a reason for discordance between patient choice and final choice through dialysis modality.

Yet another advantage of the present invention is to provide an integrated access management program for PD and HD patients.

A still further advantage of the present invention is to provide a system and a method for monitoring a patient via the Internet or a modem.

And, another advantage of the present invention is to provide a system and a method that allows customization and access to components of the dialysis software with respect to a patient.

A further advantage of the present invention is to provide a system and a method for transferring a patient from one physician to another physician or other healthcare provider.

Yet another advantage of the present invention is to provide a system and a method for transferring a patient from one database to another database without losing or otherwise requiring separate input of information regarding the patient.

Yet another advantage of the present invention is to provide a system and a method for identifying routine laboratory tests and/or simplified comparison of pre-treatment results and/or post-treatment results.

A still further advantage of the present invention is to provide a system and a method for identifying care givers associated with a particular patient to enhance the assignment of a patient care team.

Moreover, an advantage of the present invention is to provide a system and a method that allows multiple facilities to use one database with different security profiles.

Yet another advantage of the present invention is to provide a system and a method that provides customized viewing and/or access rights for each member of a renal care team.

A still further advantage of the present invention is to provide a system and a method for managing access sites for a patient undergoing treatment for peritoneal dialysis (PD) or hemodialysis (HD).

A further advantage of the present invention is to provide a system and a method for access information of for a patient undergoing treatment for peritoneal dialysis (PD) or hemodialysis (HD), the information relating to access placement, infection problems, non-infection problems, medications, and/or hospitalizations.

Yet another advantage of the present invention is to provide a system and a method that provides simple tracking of PD and HD management in a single module.

Still another advantage of the present invention is to provide a system and a method that provides a display of the history surrounding the access management system.

Another advantage of the present invention is to provide a system and a method that provides a display of the treatment history for a patient.

Yet another advantage of the present invention is to provide a system and a method that provides a display of the hospitalization history for a patient.

Still another advantage of the present invention is to provide a system and a method that provides a display of the access history for a patient.

Additional features and advantages of the present invention are described in, and will be apparent from, the detailed description of the presently preferred embodiments and from the drawings.

BRIEF DESCRIPTION OF THE FIGURES

FIG. 7 illustrates a center and patient demographic screen in an embodiment of the present invention.

FIG. 8 illustrates a screen that prompts input or information regarding a clinical encounter in an embodiment of the present invention.

FIG. 9 illustrates a screen relating to a CKD care pathway in an embodiment of the present invention.

FIG. 10 illustrates a screen relating to a CKD care pathway in an embodiment of the present invention.

FIG. 14 illustrates a patient transfer screen in an embodiment of the present invention.

FIG. 17 illustrates an import and maintenance screen in an embodiment of the present invention.

FIG. 18 illustrates an import and maintenance screen in an embodiment of the present invention.

FIG. 20 illustrates a clinical history screen in an embodiment of the present invention.

FIG. 21 illustrates a patient demographic screen in an embodiment of the present invention.

FIG. 22 illustrates a clinical history screen in an embodiment of the present invention.

FIG. 23 illustrates a medications maintenance screen in an embodiment of the present invention.

FIG. 29 illustrates a screen which contains nurse information in an embodiment of the present invention.

Figure 32:
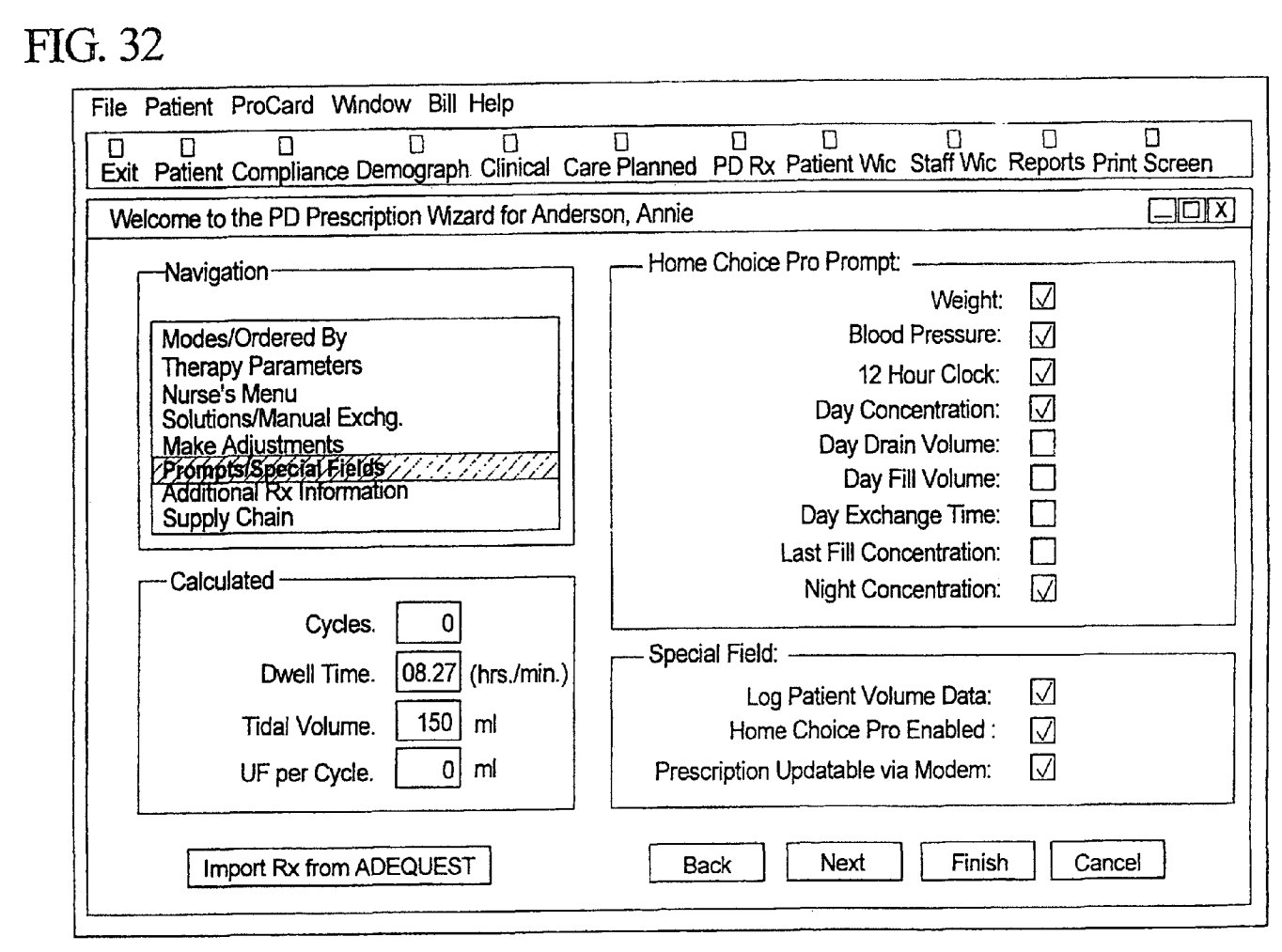

FIG. 32 illustrates a screen which provides prompts and special fields to a -user in an embodiment of the present invention.

FIG. 33 illustrates a screen which contains prescription information in an embodiment of the present invention.

FIG. 50 illustrates a screen that pops up as a reminder regarding specific items that must be completed in a "to-do list" format in an embodiment of the present invention.

FIG. 51 illustrates a screen containing clinical encounter information in an embodiment of the present invention.

FIG. 52 illustrates a screen containing clinical pathway information in an embodiment of the present invention.

FIG. 54 illustrates a screen containing a mineral metabolism pathway in an embodiment of the present invention.

FIG. 55 illustrates a screen containing education tracking in an embodiment of the present invention.

FIG. 56 illustrates a screen containing education assessment in an embodiment of the present invention.

FIGS. 57(a) and 57(b) illustrate a screen containing care pathway information for modality eligibility and/or planning in an embodiment of the present invention.

FIGS. 58(a) and 58(b) illustrate a screen relating to modality choice which indicates a care giver's opinion for which therapy should be chosen for the patient based on eligibility criteria or patient discussion in an embodiment of the present invention.

FIG. 59 illustrates a screen for access planning to note a type of dialysis access chosen in an embodiment of the present invention.

FIGS. 60(a) and 60(b) illustrate dialysis initiation screens which track a type of dialysis access in an embodiment of the present invention.

FIGS. 61(a) through 61(f) illustrate charts defining various care pathway assignments based on various laboratory results in an embodiment of the present invention.

FIG. 62 illustrates a clinical pathway screen relating to preventative measures in an embodiment of the present invention.

FIG. 64 illustrates a clinical pathway screen for lipid disorders in an embodiment of the present invention.

FIG. 67 illustrates an access summary screen in an embodiment of the present invention.

FIG. 68 illustrates a treatment history screen in an embodiment of the present invention.

FIG. 69 illustrates a hospitalization summary screen in an embodiment of the present invention.

FIG. 70 illustrates an access screen containing implant details of a patient in an embodiment of the present invention.

FIG. 71 illustrates an access screen containing clinical assessment of a patient in an embodiment of the present invention.

FIG. 72 illustrates an access screen containing culture sample indicators in an embodiment of the present invention.

FIG. 73 illustrates an access screen containing dynamic assessments of a patient receiving hemodialysis in an embodiment of the present invention.

FIG. 74 illustrates an access screen containing dynamic assessments of a patient receiving peritoneal dialysis in an embodiment of the present invention.

FIG. 75 illustrates a screen containing infection data in an embodiment of the present invention.

FIG. 76 illustrates a screen containing non-infection problem data in an embodiment of the present invention.

FIG. 77 illustrates a screen containing medications data in an embodiment of the present invention.

FIG. 78 illustrates a screen containing hospitalization data in an embodiment of the present invention.

FIG. 79 illustrates a CKD access planning screen in an embodiment of the present invention.

FIG. 80 illustrates a screen containing hemodialysis prescription information in an embodiment of the present invention.

FIG. 81 illustrates a screen containing hemodialysis treatment information in an embodiment of the present invention.

FIG. 82 illustrates a screen containing PD prescription information in an embodiment of the present invention.

FIG. 83 illustrates a screen containing PD compliance information in an embodiment of the present invention.

DETAILED DESCRIPTION

The present invention relates to a system and a method for providing care and or therapy to a patient. Moreover, the present invention provides a system and a method for tracking care or therapy to a patient, particularly a patient with renal disease. More specifically, the present invention relates to a system and a method for tracking therapies and/or care to a patient throughout the various stages of renal disease, particularly Chronic Kidney Disease (CKD).

Figure 1:
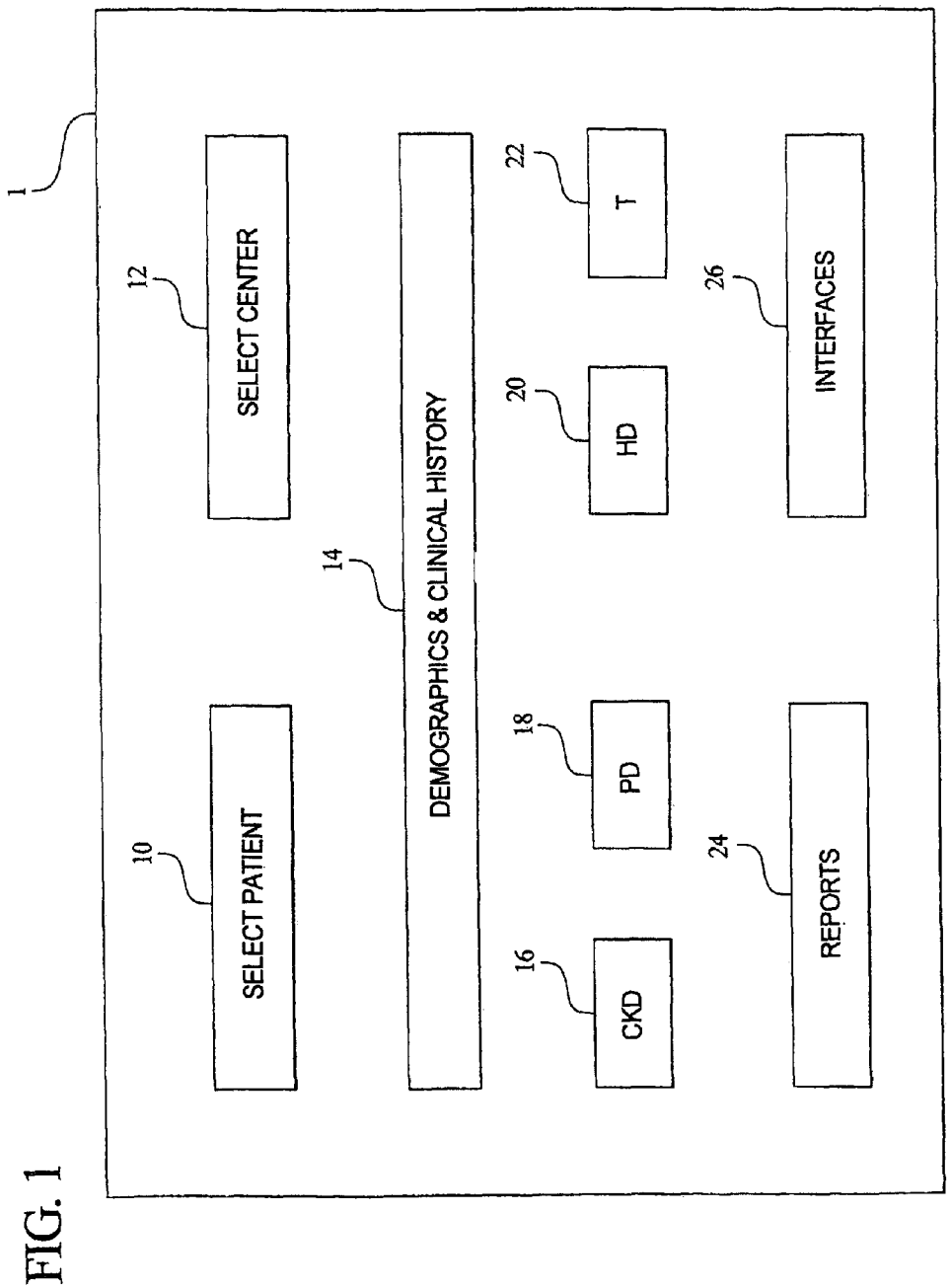
FIG. 1 illustrates a block diagram of a system in an embodiment of the present invention.

The present invention generally relates to a system 1 that may be integrated such that a patient undergoing therapy has a history that tracks the patient during any stage of that therapy using the system 1. As illustrated in FIG. 1, the system 1 is integrated such that a patient 10 or a group of patients 10 or a center 12, such has a hemodialysis center, are integrated within the system 1. The demographics and clinical history of each of the patients 10 and each of the centers 12 are included within the integrated system 1 such that the patient 10 is tracked throughout any stage of renal disease, particularly chronic kidney dialysis (CKD module) 16, peritoneal dialysis (PD module) 18, hemodialysis (HD module) 20, and/or transplant (T module) 22. The integrated system 1 also generates reports 24 and has multiple interfaces 26 with external resources or other processes relevant to the care of the patient 10. Demographics 14a of the patient 10 may be input into the system 1 such that the patient 10 may be identified at least by name, birth date, age, gender and/or other identifiers. The clinical history 14b within the integrated system 1 is capable of tracking history of the patient 10 from the onset of care. The clinical history 14b may include events, descriptions and/or dates. In addition, descriptions and/or dates of the following may be included: co-morbidities, hospitalizations, medications, surgeries and/or labs.

Within the CKD module 16 of the system 1, the status of renal function, related complications, co-morbidities profiling, medications/lab tracking and the like may be identified. Within the PD module 18, access, prescription, complications or infections or other information, patient status, compliance, summary reports as well as other functions and other information may be provided. Within the hemodialysis module 20, similar information, namely, description, complications, infections, catheter information, patient status, compliance, reports and other functions and information may be tracked. Within the transplant module 22, a transplant patient identifier, a history of treatment, as well as medication/lab tracking and/or co-morbidities tracking may be provided. The reports 24 with any portion of the system 1 may include physician, nurse, administrative and/or ad hoc reports. An interface 26 may be provided within the system 1 to link with other clinical systems, laboratories, supply chains, and/or other service requirements.

Figure 2:
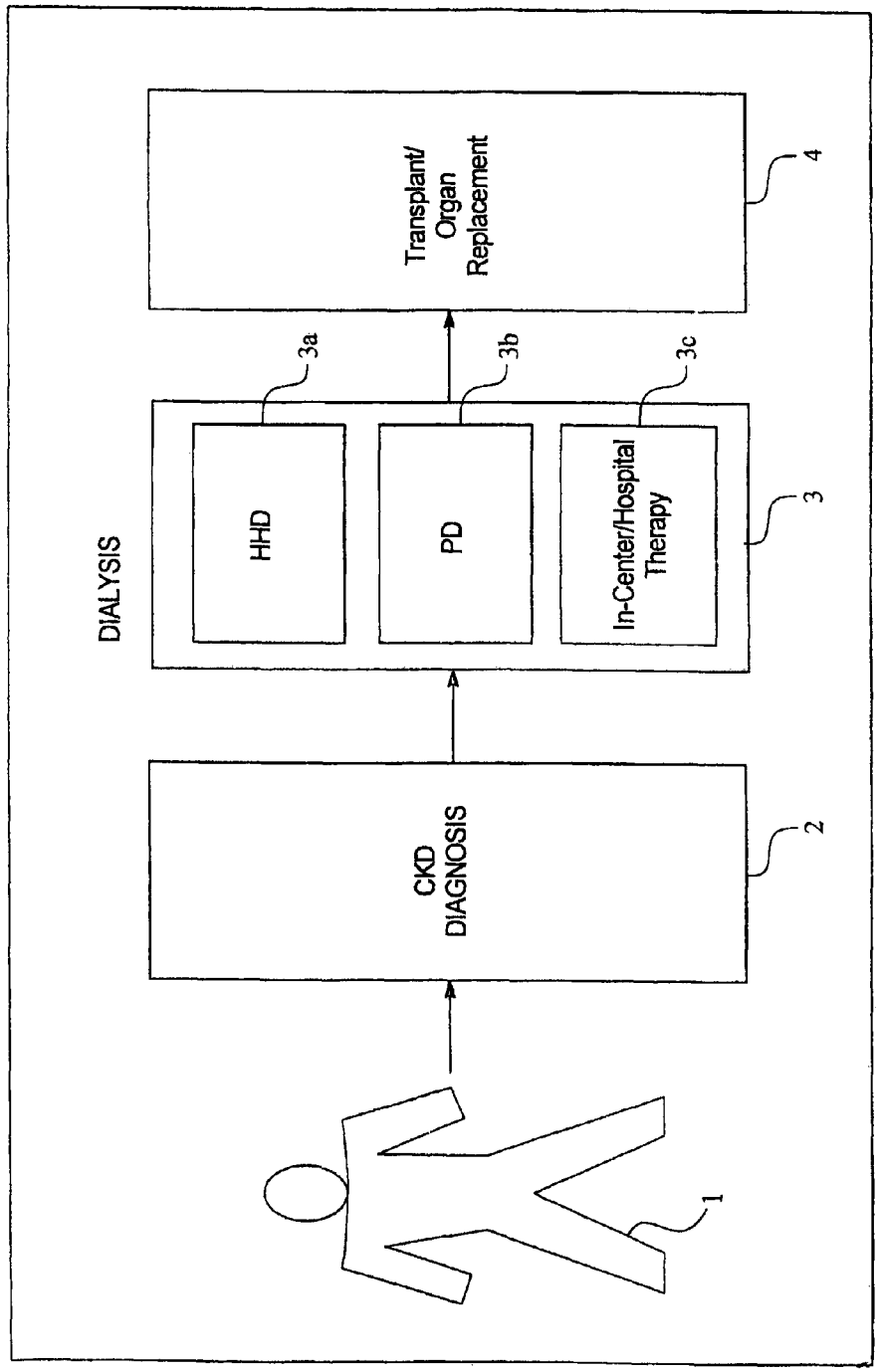
FIG. 2 illustrates a black box diagram associated with treatment of a patient in an embodiment of the present invention.

FIG. 2 generally illustrates the cycle of a patient. An at-risk patient 10 may be diagnosed at step 2 as a patient with chronic kidney disease (CKD). Step 3 is a dialysis section wherein the patient undergoes one of home hemodialysis as shown within Step 3 at 3a, peritoneal dialysis (PD) at 3b, or in-center or hospital therapy as shown at 3c. At step 4, some patients may be identified as requiring organ replacement or transplant. As shown in FIG. 2, at the diagnosis step, CKD may be identified, characterized and/or patients may be channeled into care pathways utilizing educational and medical guidelines. To this end, physicians may gain an understanding of the patient and patient adjustment may be enhanced through education. As a result, dialysis may be initiated in a timely manner and/or clinical outcomes may be improved.

If PD is suggested and/or required for the patient, a link is provided resulting in continuity of care for the patient and monitoring of the patient through continuous monitoring of the patient and automated transfer of the information regarding the patient into the system 1. A patient may also be monitored for compliance to prescribed versus delivered therapy during PD. As a result, enhanced problem identification and/or simplified patient training may be provided. In addition, home hemodialysis monitoring may be provided resulting in real-time monitoring of the patient during dialysis. A physician or other medical or clinical staff may link to the home of a patient via the internet or modem.

Figure 3:
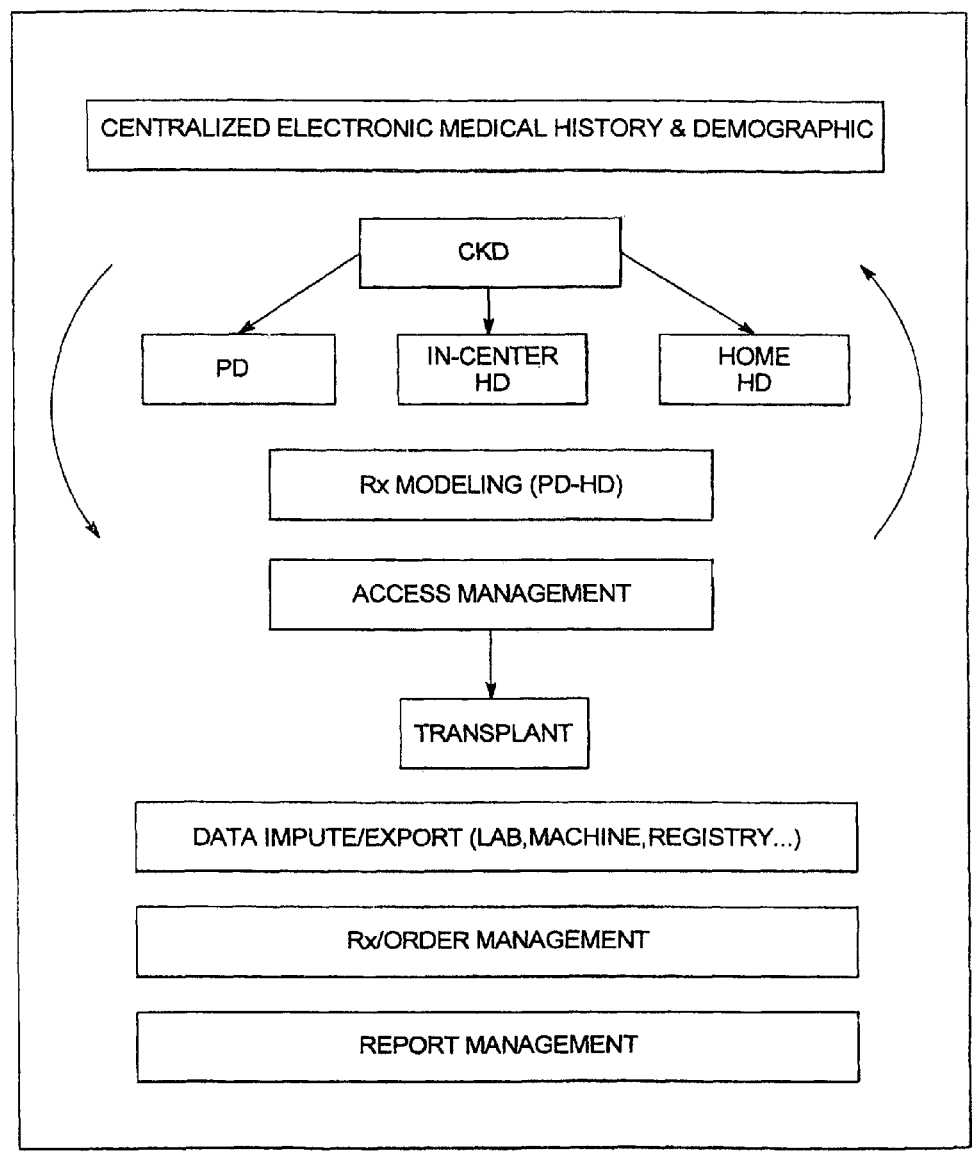
FIG. 3 illustrates a diagram of modules for tracking and/or monitoring a patient throughout the various stages of renal disease in an embodiment of the present invention.

As shown in FIG. 3, the system 1 of the present invention provides centralized electronic medical history and demographic information that is integrally installed on a single platform with data import, data input, and data export capabilities with a laboratory and/or registries and the like. Prescription and order management may also be provided as well as report management.

Within the system 1, certain functions may be activated or deactivated depending on the particular patient. First, the patient may be identified as a patient with chronic kidney disease and may require peritoneal dialysis, in-center hemodialysis, and/or home hemodialysis. Prescription modeling and/or access management may be provided as required depending on the type or types of therapy which the patient may be undergoing. Further, a transplant module may also be activated or deactivated based on the particular patient.

The system 1 of the present invention may be implemented to provide a single system and method for tracking and/or monitoring a patient throughout the various stages of renal disease and to identify the appropriate pathways for each patient and organizing the care standardization of data capture resulting in the continuity of care and data capture for each patient, as well as efficient data retrieval and targeted data exploration for the patient.

Figure 4:
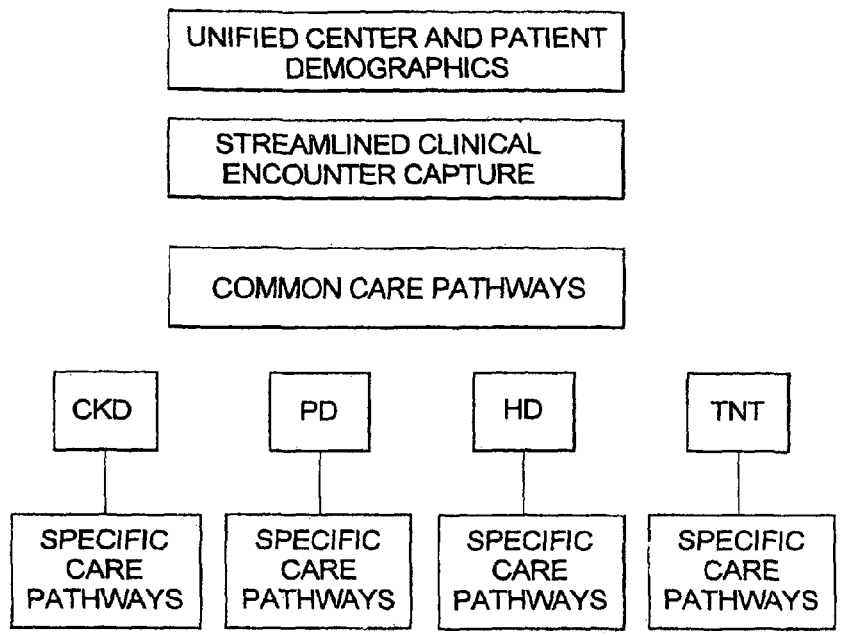
FIG. 4 illustrates a flowchart for identifying care pathways in an embodiment of the present invention.

As shown in FIG. 4, an approach or method using the system 1 and method of the present invention results in unified center and patient demographics input into the system and streamlining the clinical encounter captured as a result of use of the system and method of the present invention. FIG. 4 shows common care pathways identified for each of CKD, PD, HD and transplant. As a result of those particular identifications, specific care pathways may then be identified for each patient within each category of treatment, namely, CKD, PD, HD and transplant.

Figure 5:
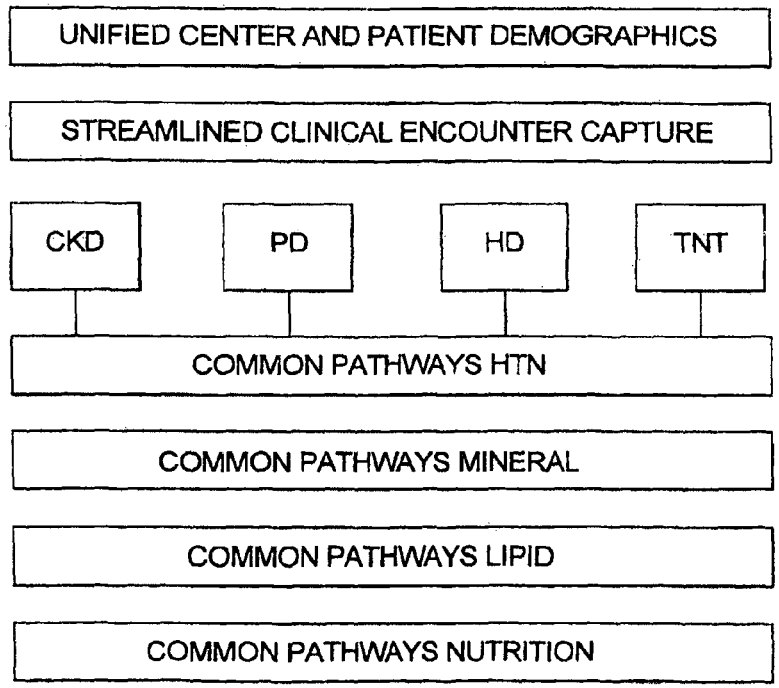
FIG. 5 illustrates a flowchart for identifying care pathways in an embodiment of the present invention.

FIG. 5 illustrates an alternate approach in which unified center and patient demographics are obtained through streamlining clinical encounter capture for each of CKD, PD, HD and transplant therapies and common pathways for various data identified, tracked and/or otherwise addressed, such as hypertension, mineral, lipid and/or nutrition.

Figure 6:
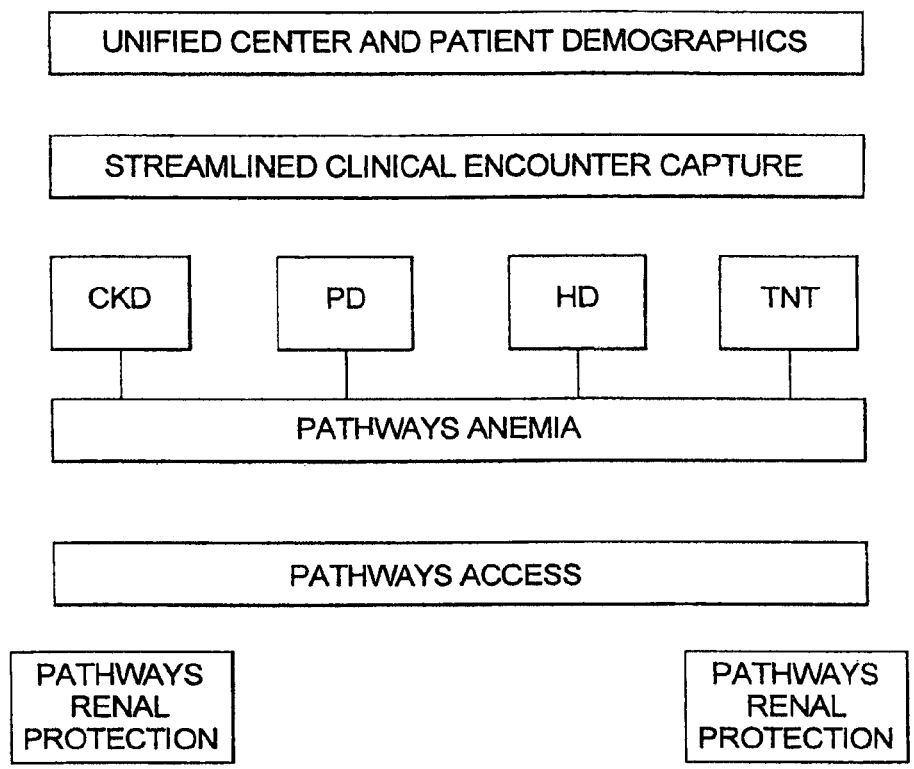
FIG. 6 illustrates a flowchart for identifying care pathways in an embodiment of the present invention.

As shown in FIG. 6, another approach through unified center and patient demographic input through streamlined clinical encounter capture for each of CKD, PD, HD and transplant treatments, various pathways are identified such as, for example, anemia, providing pathway access to subsequent pathways for renal protection.

FIG. 7 illustrates an embodiment of a center and patient demographic screen for a particular patient. The screen provides for input via tabs 30 for various demographic information for a particular patient such as professional contact information and emergency contact information, employment information, insurance information, personal information, address information, telephone or e-mail information, and the like.

FIG. 8 illustrates a screen that prompts input or information regarding clinical encounter. Various tabs are provided, such as the encounter summary tab 32 which identifies various information regarding the specific encounter of the particular patient by the physician or other medical professional treating the patient. The tabs may include information regarding summarizing the encounter, information regarding renal disease, system review and/or physical assessment of the patient.

Figure 9:
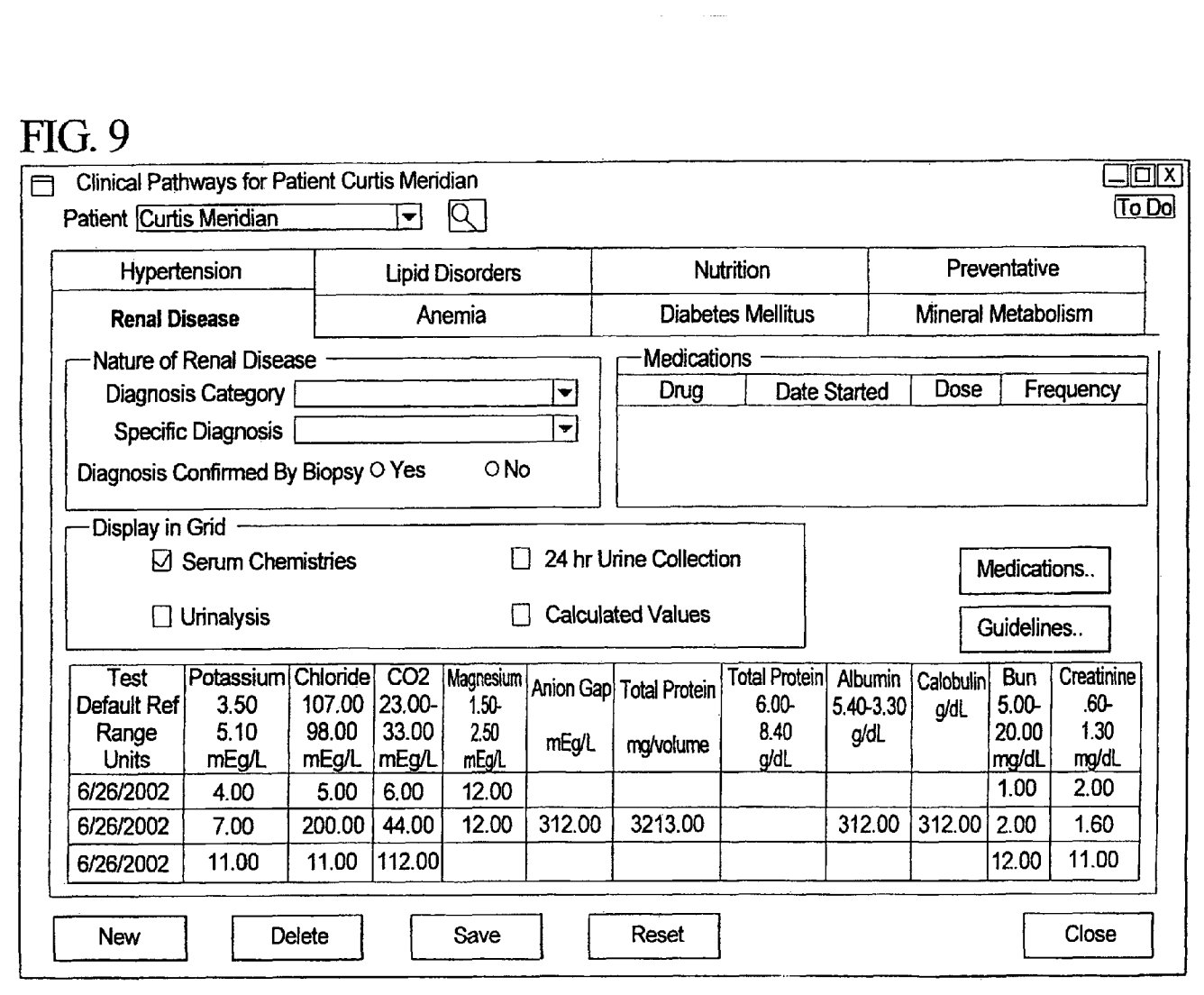
Figure 10:
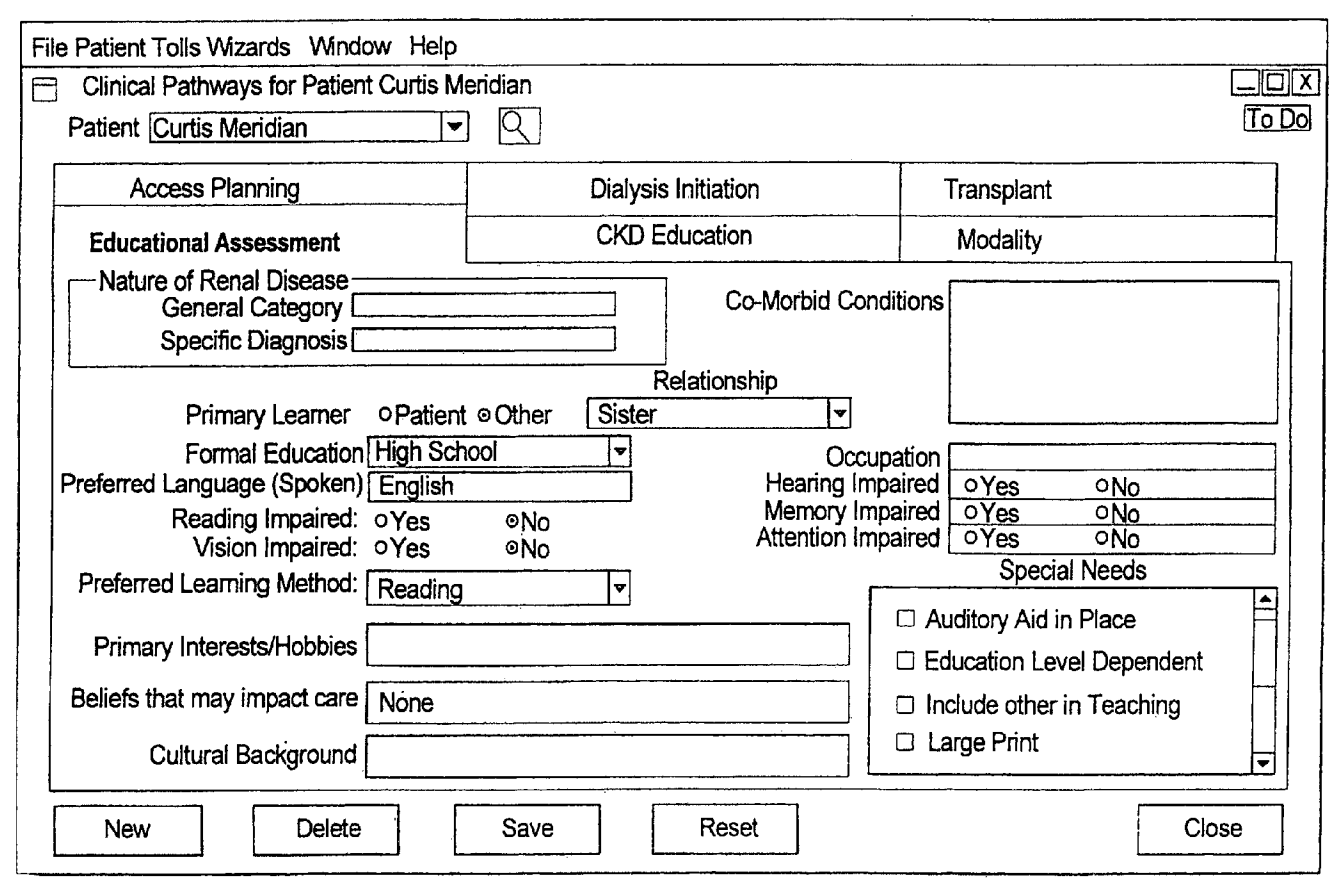

A care pathway may then be identified for the particular patient identified by various tabs or, for example, hypertension (HPT), lipid disorders, nutrition, preventative, renal disease, anemia, diabetes mellitus and/or mineral metabolism, and the like as shown in FIG. 9. Additional care pathways may also be provided for a patient, such as tabs for access planning, dialysis initiation, transplant, educational assessment, CKD education, and modality as shown in FIG. 10.

Figure 11:
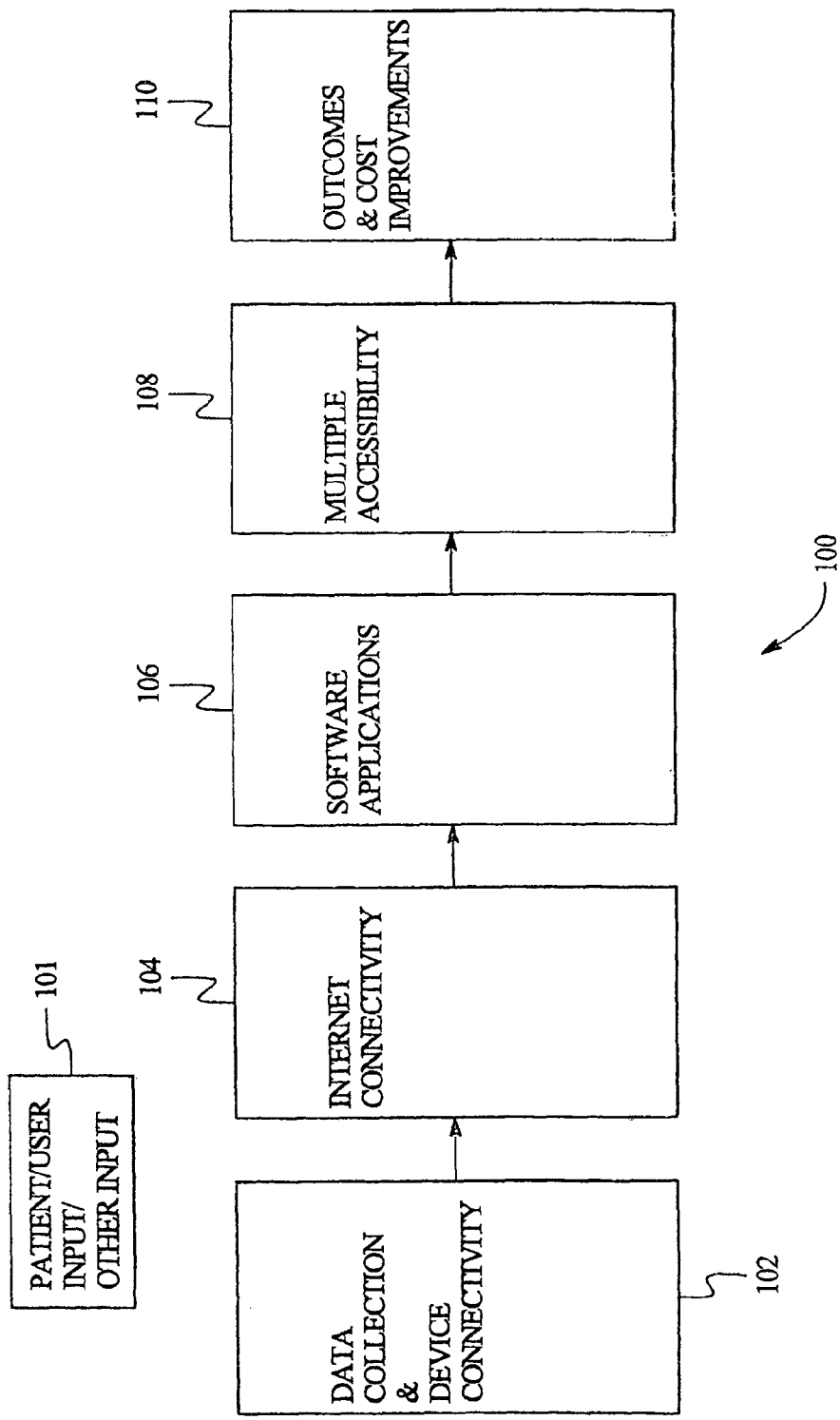
FIG. 11 illustrates a block diagram of a method for tracking patient activity in an embodiment of the present invention.

FIG. 11 illustrates a method 100 for using the system 1 of the present invention. A first step is identified at step 102 where data collection and device connectivity are provided. Data may be collected through manual input via, for example, the integrated software of the system 1 requiring patient input or center input or other user input as shown at step 101. The input may also be provided via, for example, a personal digital assistant or other wireless input device. Alternatively or in addition, machine input may be provided by direct monitoring, for example, of a patient within a center. Or, for example, if home hemodialysis is taking place, the information may be transferred, data may be collected and/or moved to and/or from multiple patients without regard to the type of therapy which the patient may be undergoing during any stage of the renal disease of the patient.

Internet connectivity with a consolidated database may be provided as shown at step 104. The internet connectivity may be provided at a data hub providing information to the internet via a browser. Or, a server database may be provided that may provide the necessary legal, privacy, security and/or regulatory issues for the monitoring of the patient through the various stages of renal disease. Connected to the internet are various software applications as shown at step 106 wherein information may be downloaded to and/or from the software to provide the necessary processing of the data for any type of renal disease that the patient may be experiencing. The method provides multiple accessibility as shown at step 108 or multiple users and multiple tools. Among the users may be the patient, a clinician or other medical or technical professional. A provider, a supplier, a laboratory or other corporate or professional resource may also be defined as a "user." Multiple tools may also be provided to assist with the administration of care to the patient throughout each stage of the renal disease that may be experienced by the patient. For example, tools that may be used to assist the patient or any other users include a computer, e-mail, telephone, telefax, or the like.

The final step 110 of the method 100 results in various outcomes that may be provided as a result of the method of the present invention as illustrated in FIG. 11. The patient may be tracked through his/her therapy lifetime. In addition, the system and method of the present invention tracks multiple patients through their therapy lifetimes. The history of patients is not lost as the patient is transferred from one therapy option to another option. In addition, all history from the CKD phase may be transferred with the patient or patients to the dialysis and/or transplant care professionals, or medical care clinicians or other professionals. The system and the method provides a comprehensive integrated software tool that allows renal patient data to be transferred from the CKD phase to the patient's first therapy option to ensure continuity in treatment history.

All therapy options may be recorded within the software so patients may be transferred to and from PD, HD, and/or transplant therapies without losing previous treatment history. Clinical and therapeutic features include the managing and/or monitoring of CKD patients to track renal disease progression and/or complications. Data may be recorded for therapy option education, modality selection, and/or access placement preparation. In addition, clinical patient management may be provided to track medications and/or monitor compliance. Further, complications and/or infections may be tracked. Further, co-morbidities may be managed; and clinical assessment and/or history of the patient may be monitored. As a result, the organization of the delivery of care may be enhanced by creating a single source for all clinical information. Timely initiation of dialysis may also be provided that may reduce urgent start of the particular dialysis therapy, improved clearances, as well as saved medical professional time for physicians, nurses, or other medical professionals.

From an operational and administrative standpoint, data may be captured from machines and other sources. Captured data may be accessed and/or exchanged remotely. Remote access and/or exchange include clinical data and/or machine parameters via two-way communication. Moreover, data may also be automatically imported, and the data may also be exported. Dialysis product supply management may be enabled resulting in electronically presenting new patients and/or creating initial orders. Further, prescriptions may be automatically submitted to, for example, suppliers. Still further, remote diagnostics of dialysis devices may be provided through the system and method of the present invention to determine and/or solve problems associated with, for example, showing which patient may be connected. Problems may be determined and/or fixed with, for example, a modem and/or the internet. As a result, a single source for clinical data and/or machine data may be created. Patients visits may be reduced and annual data entry may be eliminated. Administrative time and paperwork, as well as human errors, may also be reduced and/or saved. From a patient's standpoint, anxiety or hassle that a patient may experience may be lessened or eliminated. Moreover, missed exchanges required by the patient may be reduced and/or eliminated.

Figure 12:
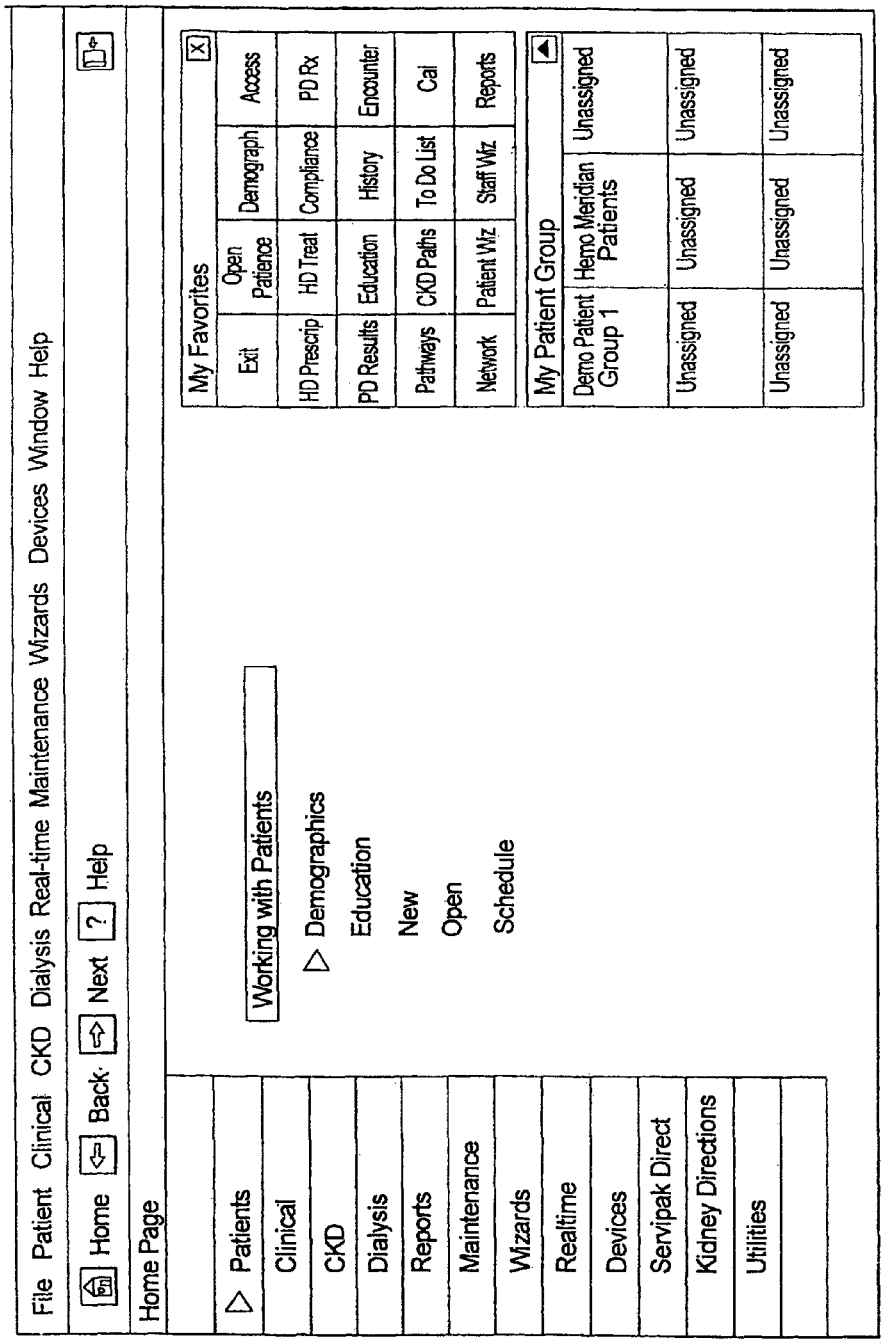
FIG. 12 illustrates a new entry screen in an embodiment of the present invention.

To initiate use of the system and method of the present invention, an entry screen, as illustrated in FIG. 12, may be provided. The patient entry screen provides customization as well as access to all components of the system and method of the present invention.

Figure 13:
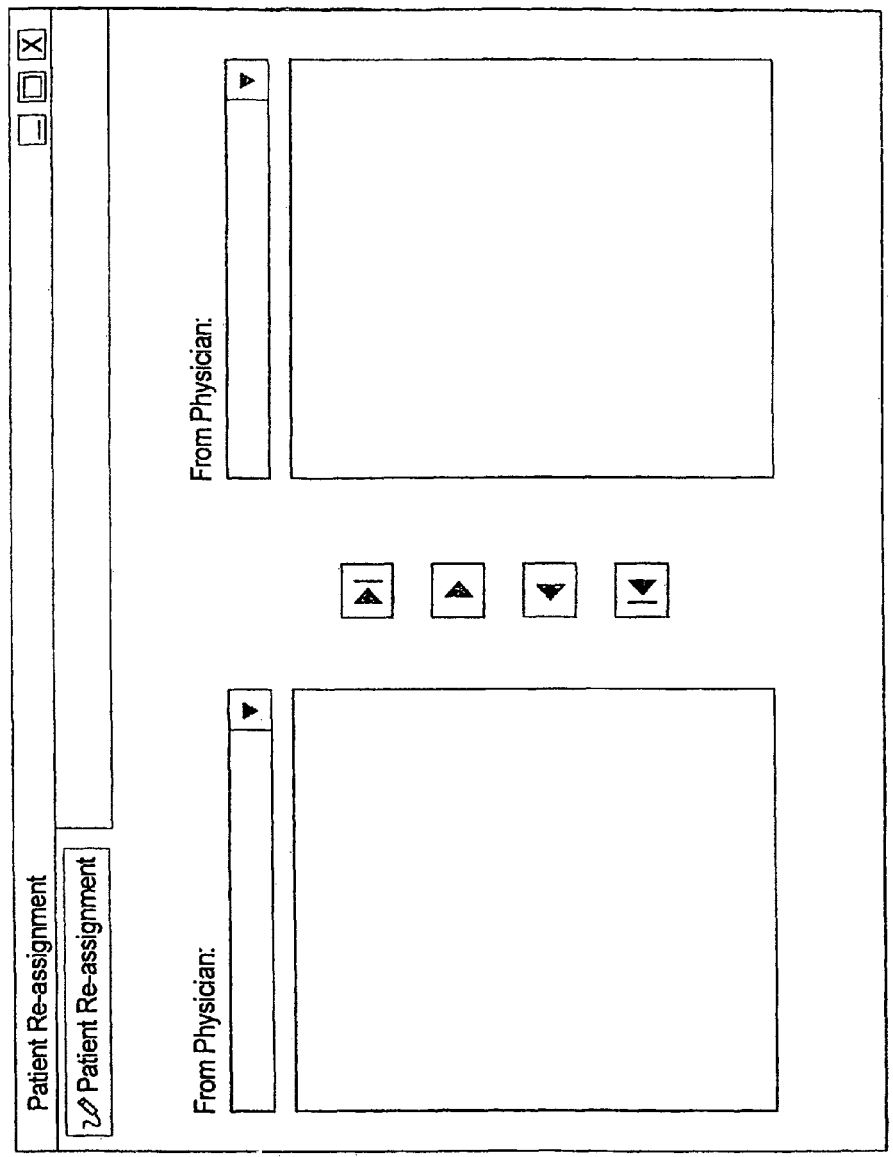
FIG. 13 illustrates a patient re-assignment screen in an embodiment of the present invention.
Figure 15:
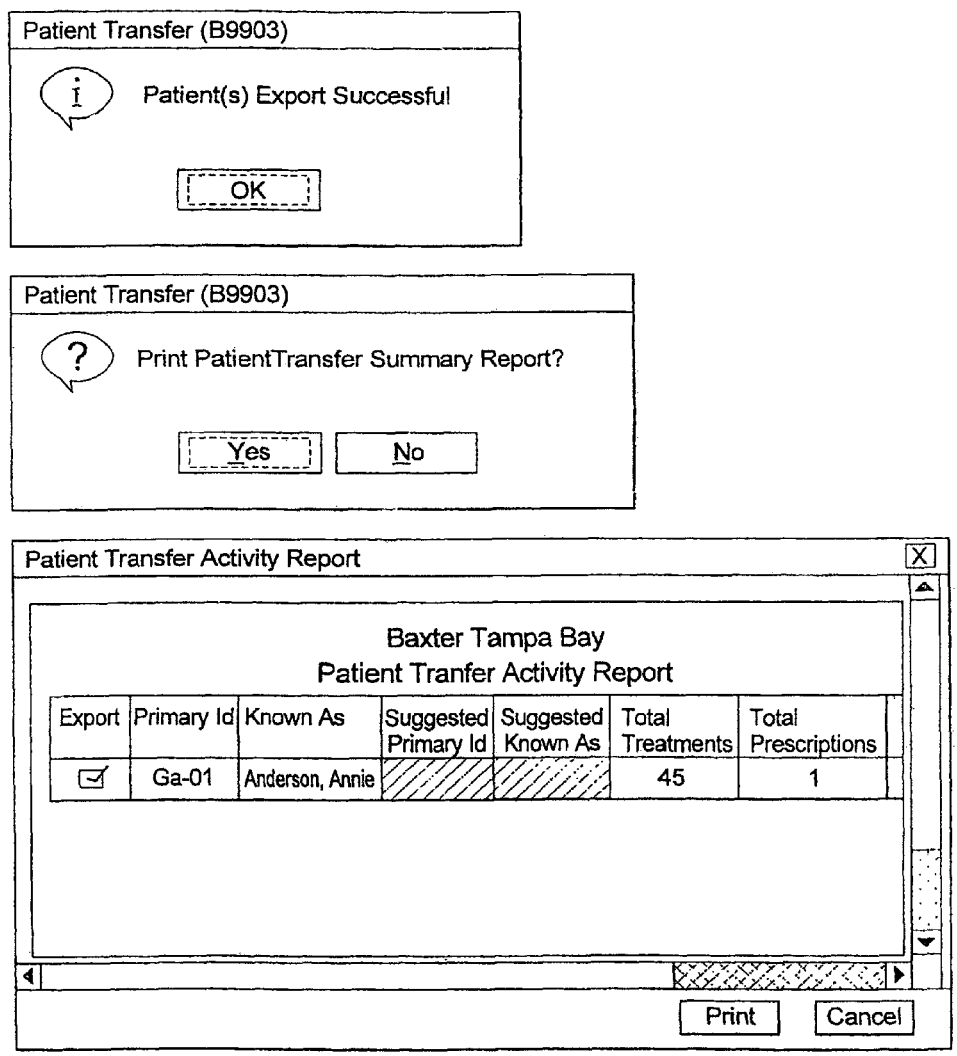
FIG. 15 illustrates a patient transfer screen in an embodiment of the present invention.

FIGS. 13-15 illustrate screens for transferring or re-assigning patients from one physician to another physician. As a result, patients may be transferred between physicians in a simplified fashion. The records of the patient are also transferred to the new physician and access may be provided through the records or the patient from the previous physician.

First, as illustrated in FIG. 13, the patient reassignment is performed by identifying the current physician of the patient. The physician's name may be identified as part of a drop down menu of physicians already input to the system of the present invention. The new physician may be identified in a second area of the screen which may also be provided in a drop down menu of physicians already input into the system.

As shown in FIG. 14, the patient transfer may be affected by importing and/or exporting patient data which may be password protected as shown in FIG. 14. One or more patients may be exported by the user by identifying patient name, a patient list, and transferring information from the patient list to the selected patient list for transfer of the patient.

Following transfer of the patient, as illustrated in FIG. 15, the user is notified that the export of the patient has been successful. The user may print a patient transfer summary report which may include various customized pieces of information. The report information for a particular patient may be customized as will be discussed hereinafter. It should be understood and appreciated that any report or function of the system may be customized as desired for the particular patient and/or the center and/or the medical professional or other user.

Another feature of the present invention is generally illustrated with respect to FIGS. 16-19 which provides for import and/or maintenance capabilities for diagnosis codes (ICD or registries) which may differ by module, ie, CKD, PD, HD and transplant.

Figure 16:
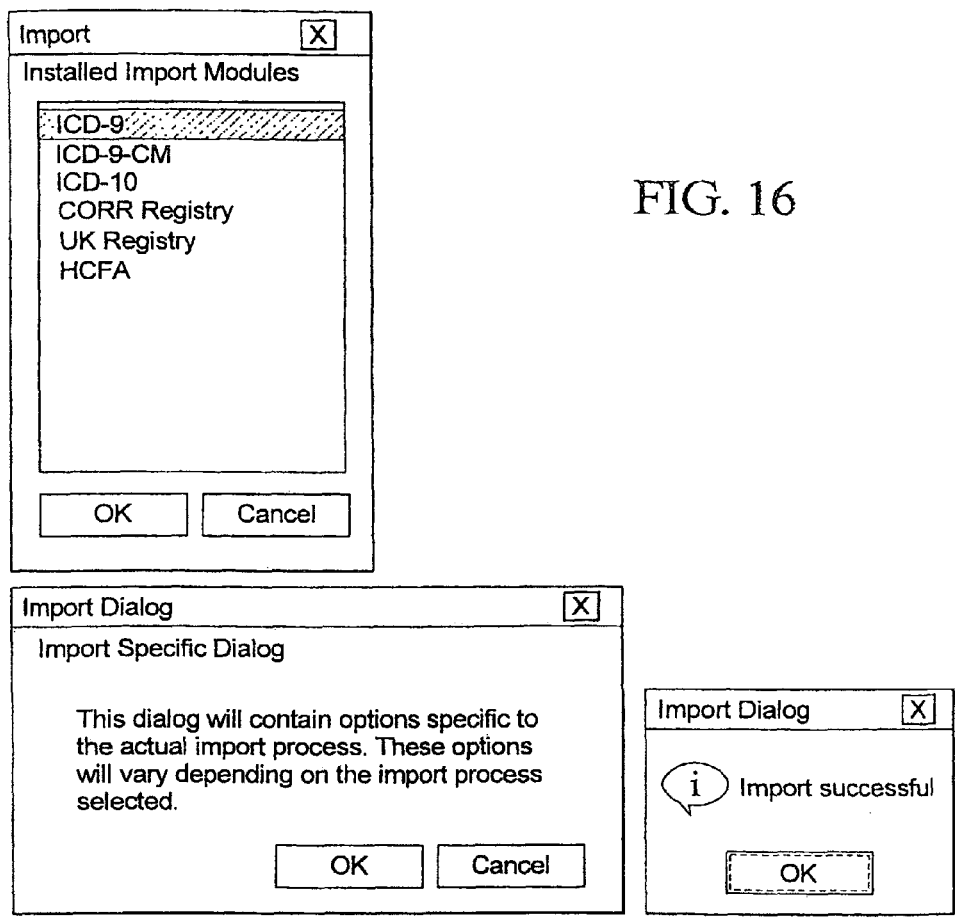
FIG. 16 illustrates an information import screen in an embodiment of the present invention.
Figure 18:
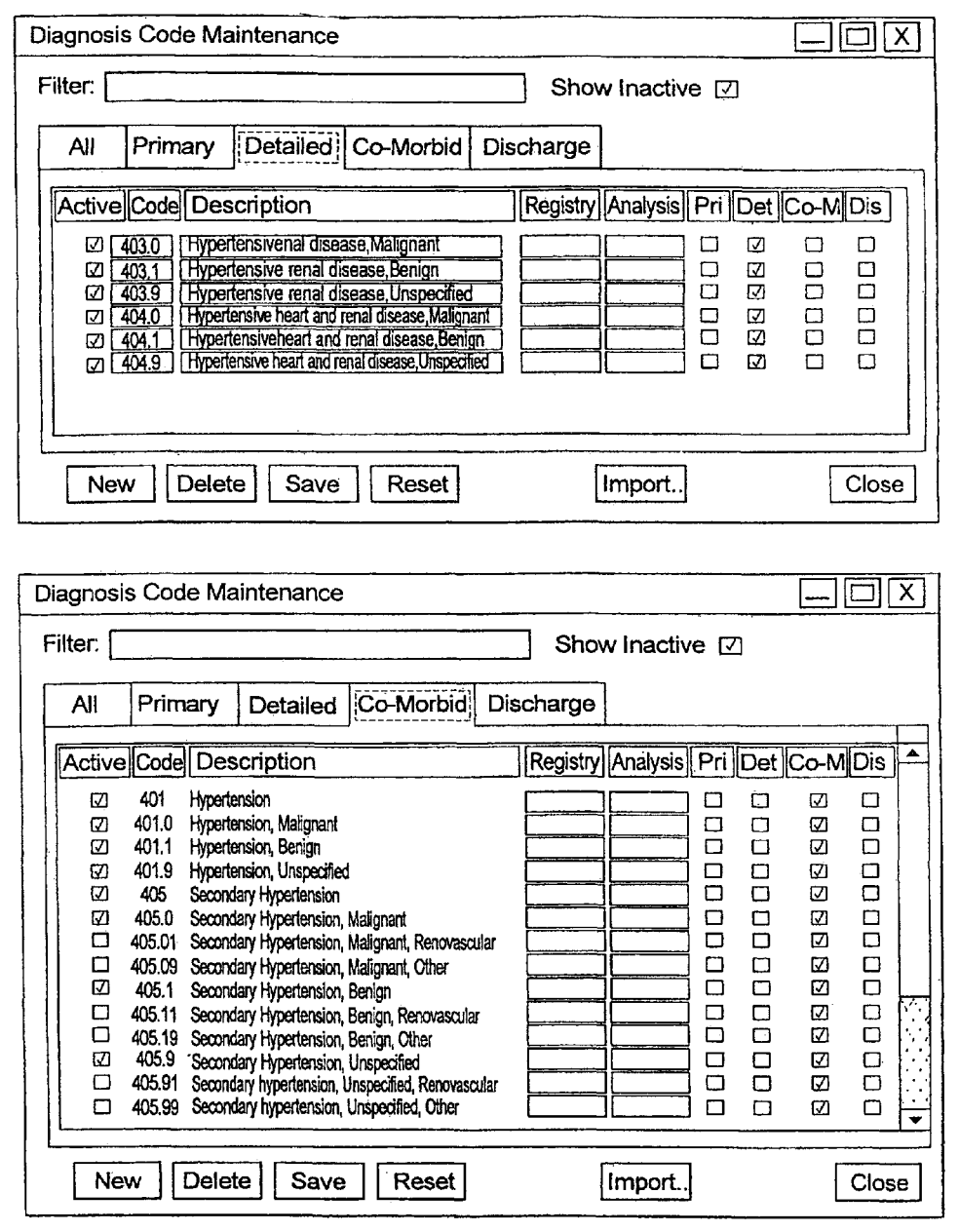
Figure 19:
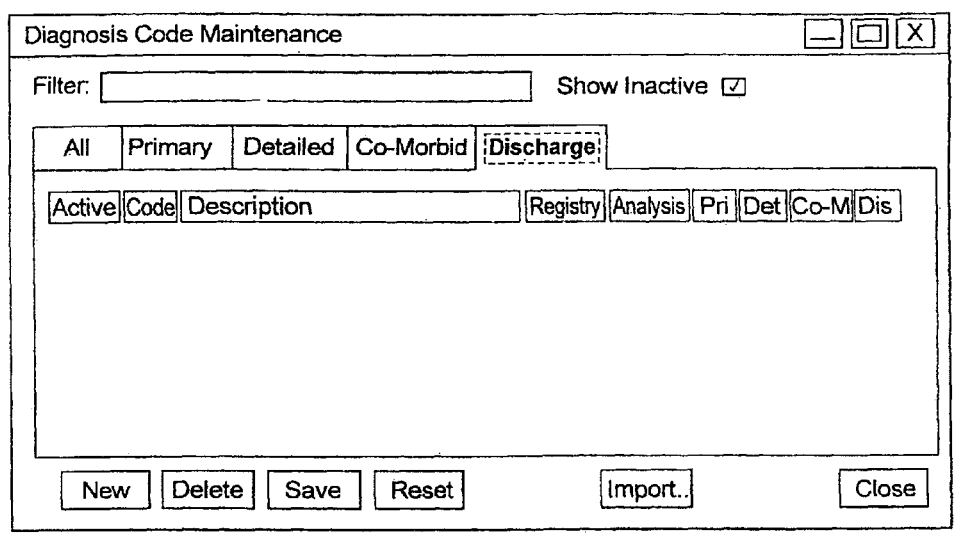
FIG. 19 illustrates an import and maintenance screen in an embodiment of the present invention.

As shown in FIG. 16, the installed import modules can be identified and imported. Diagnosis code maintenance may be provided to identify, for example, various codes associated with, for example, hypertension, as illustrated in FIG. 18. FIG. 19 illustrates, for example, existing diagnosis codes within the renal link which may be used to identify the particular code for word and/or maintenance. The diagnosis codes maintenance window adds fields for "active", "registry", and "internal system code". In addition, fields may be added for code type association as well as validation rules. The validation rules may include active codes that are unique, active descriptions that are unique and may not delete particular rows. Ability to filter by code and/or description may be provided a checkbox for display.

FIG. 20 generally illustrates screens for identifying routine lab tests for renal patients and/or to provide for analysis of pre-treatment results as well as post-treatment results. The lab results category screens illustrated in FIG. 20 provide a database linking category and source columns headed to test results table. Display groups may be selected by category. The results may be provided any column and display may be filtered to show any test results within a specific acceptable range. Moreover, test results may be displayed by filtering outside an acceptable range.

In addition to the foregoing, as illustrated in FIG. 21, enhanced renal patient care team assignment maintenance may be identified by displaying associated care givers with each renal patient. To this end, a patient name may be identified and the entire care team may be illustrated on the screen. As a result, each care giver, physician, or the like, may be immediately provided and accessed through this link.

The patient re-assignment feature, discussed above with reference to FIGS. 14 and 15, transfers renal patient data from one physician to another without manually re-assigning each patient to a new nephrologist, physician or other medical professional. The patient transfer feature transfers a CKD patient from one database to a dialysis-transplant facility database in the integrated system and method of the present invention. As a result, a new nephrologist or physician may be provided with access to treatment history in an electronic format and that history would not require printing and/or separate manual entry by the new physician. The import maintenance capabilities for diagnosis codes prevents manual entry of data by the user and provides simplified updating if a new set of codes are created.

The lab result category described with reference to FIG. 20 assists with simplified identification of routine lab tests of renal patients and simplified comparison of pre-treatment and post-treatment results. As a result, users may easily group routine lab tests.

The patient care team assignment maintenance location described with reference to FIG. 21 identifies all care givers associated to each renal patient. As a result, one central location provides a comprehensive function to track the team members from CKD, dialysis, and transplant. All of the above functions described with reference to FIGS. 12-21 are performed automatically and replace manual processes that previously were performed by a user that resulted in mistakes, or mis-entries or the like.

Another feature of the system and method of the present invention includes a medication dictionary which enables a user to create and/or save medication or prescription templates for subsequent use and/or recording and/or for prescribing treatment to a patient. FIGS. 22 and 23 illustrate a medication screen for entry of information in a template format. As a result, various components of a prescription may be standardized and saved as a "standard prescription". A series of computer dialogues are provided by the medication dictionary to enter a configuration name, medication, medication category, load dose, maintenance dose, dose unit of measure, route, frequency, frequency period, PRN (Y/N), treatment related PRN in dialysis (y/N), PRN and/or duration. In addition to those input categories, units of measure, route, frequency and frequency period may be presented as select lists to assist with the standardization of configurations and/or selections of medications for prescriptions.

FIGS. 22 and 23 illustrate screens providing medication templates for a patient resulting in a standard prescription for a particular patient. Fields within the medication configuration maintenance window may be pre-populated when a configuration is selected. Drop-down lists may be implemented to identify and assist with completing the necessary field or fields within the prescription window and/or medication tab. After a medication is selected, available configurations populate the window using the medication dictionary. The field and/or reports associated with the medication and prescription may be manipulated like any other report within the system 1 of the present invention as will be described hereinafter.

The medication dictionary creates a group of standard medication configurations for frequently prescribed medications which may be customized for a particular patient throughout the stages of renal disease. The medication dictionary contains configurations for frequently prescribed medications that may be transferred from patient to patient within each stage of renal disease.

To effect or implement a medication dictionary, a medication maintenance may first be selected by a system administrator wherein the system displays a medication configuration dialogue. The system administrator selects one of a plurality of medications, and configurations for that medication are automatically input by the system. The system administrator may select or identify desired components of the medication or the particular therapy and/or the particular patient. The system administrator may enter values for dosage, maintenance dosage, and/or duration period. Values may be further selected for units, frequency, frequency time period and routes from drop-down lists for each category. In addition, the system administrator may indicate whether medication may be given during treatment. The medication information may then be saved, and the system may store the same in the application database.

Figure 24:
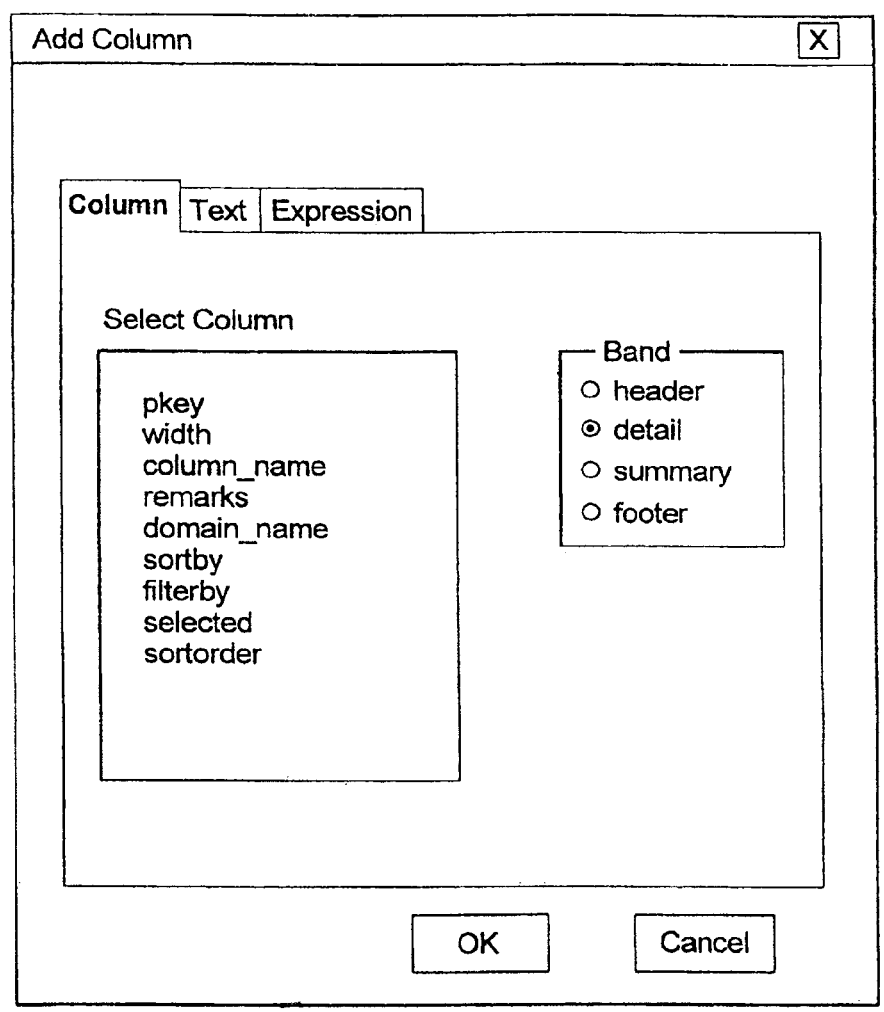
FIG. 24 illustrates a screen which prompts a user to add information to a patient file in an embodiment of the present invention.
Figure 25:
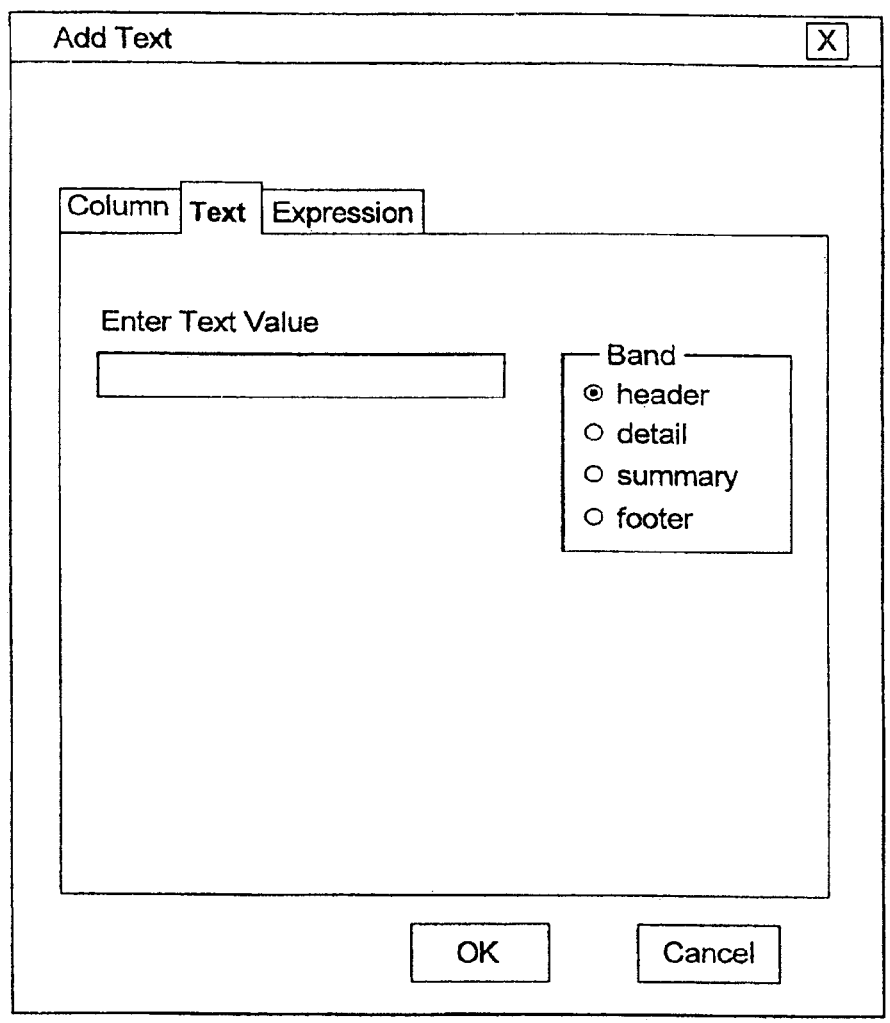
FIG. 25 illustrates a screen which prompts a user to add information to a patient file in an embodiment of the present invention.
Figure 26:
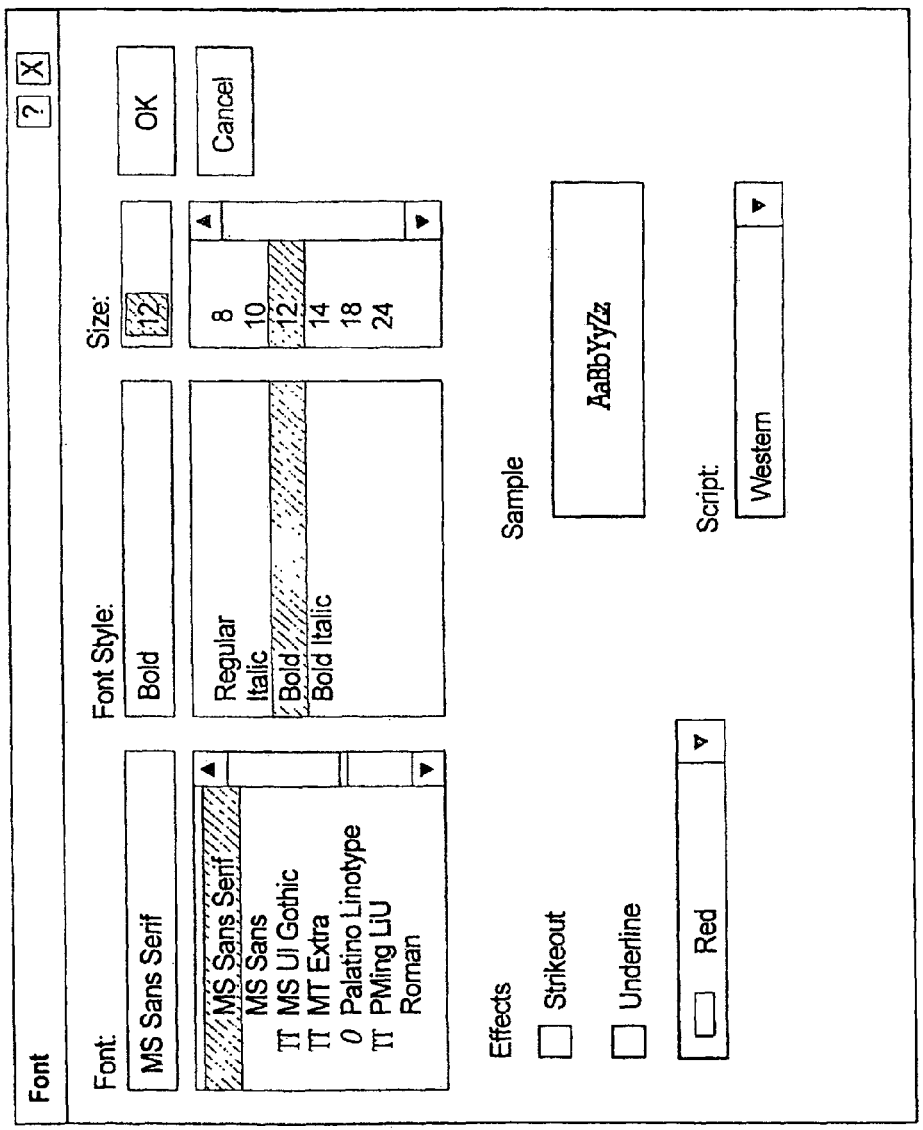
FIG. 26 illustrates a screen which prompts a user to select a font in an embodiment of the present invention.
Figure 27:
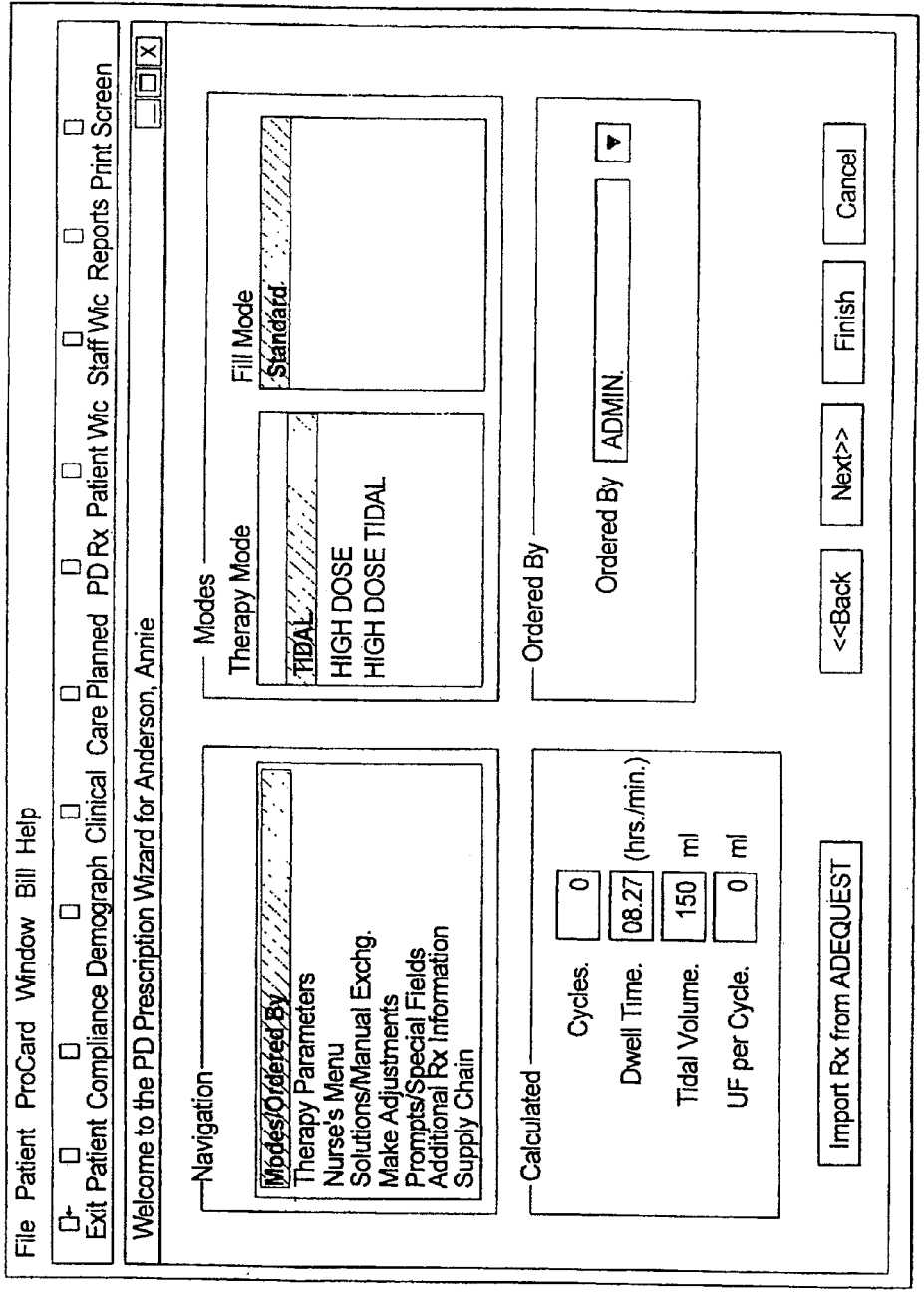
FIG. 27 illustrates a screen which prompts a user to select a mode related to filling of a prescription in an embodiment of the present invention.
Figure 28:
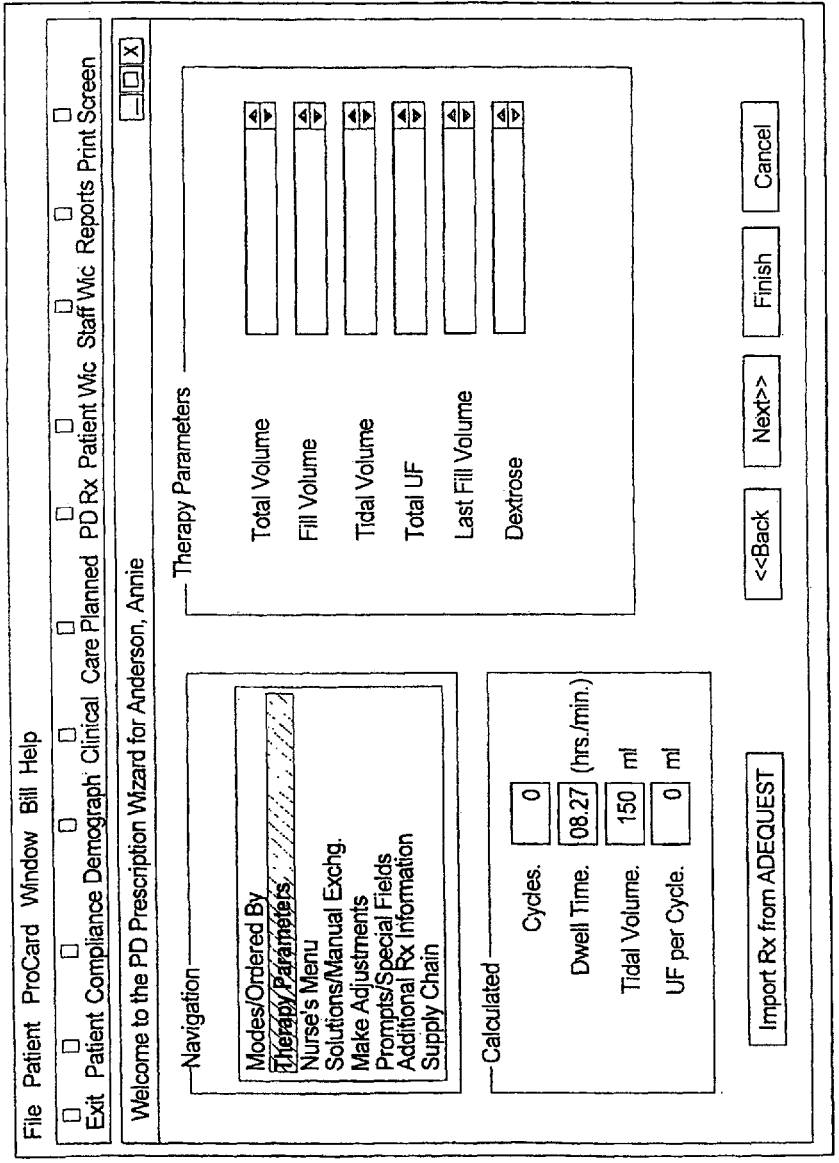
FIG. 28 illustrates a screen which provides therapy parameters in an embodiment of the present invention.
Figure 30:
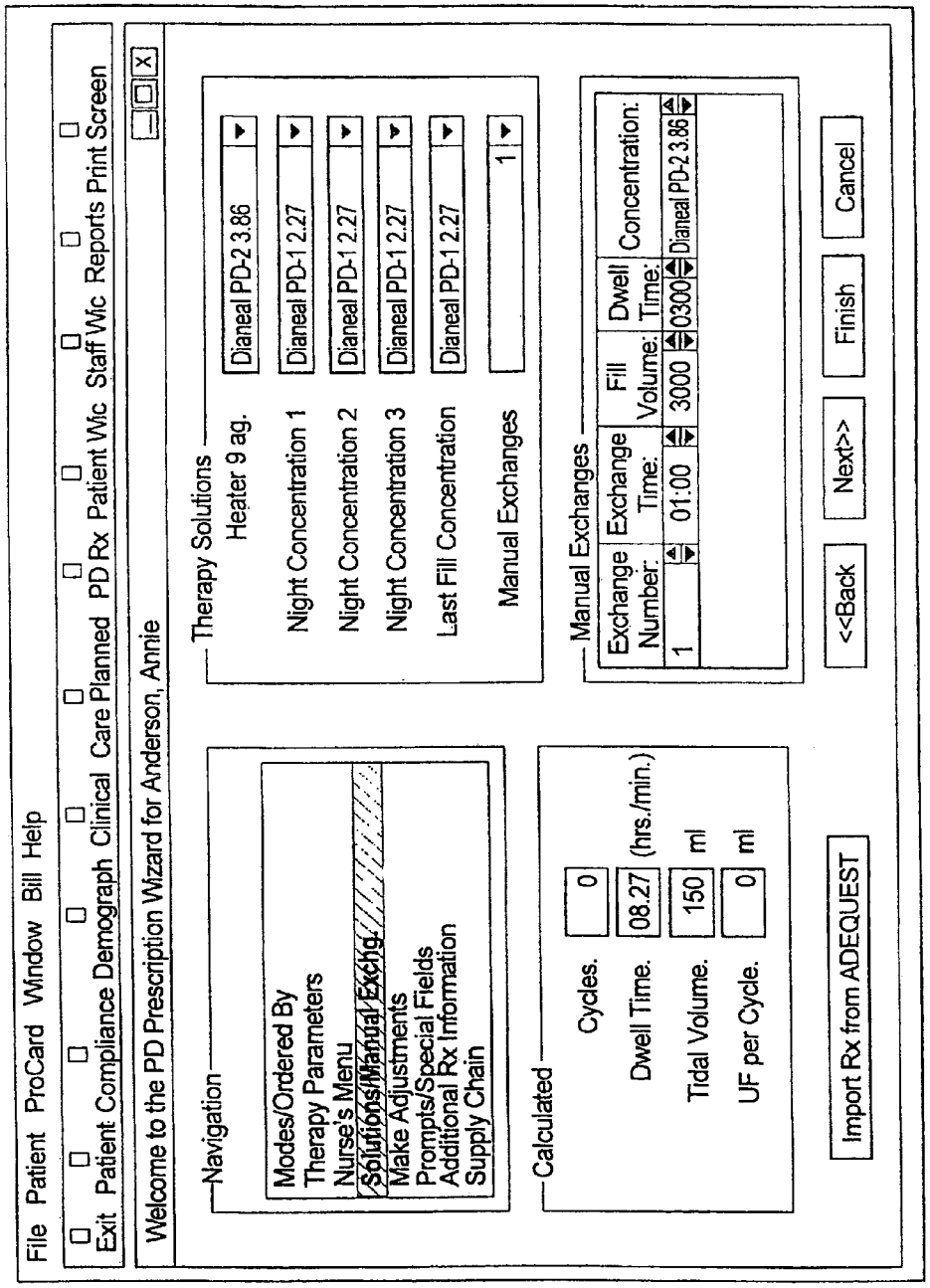
FIG. 30 illustrates a screen which provides therapy solutions and manual exchanges in an embodiment of the present invention.
Figure 31:
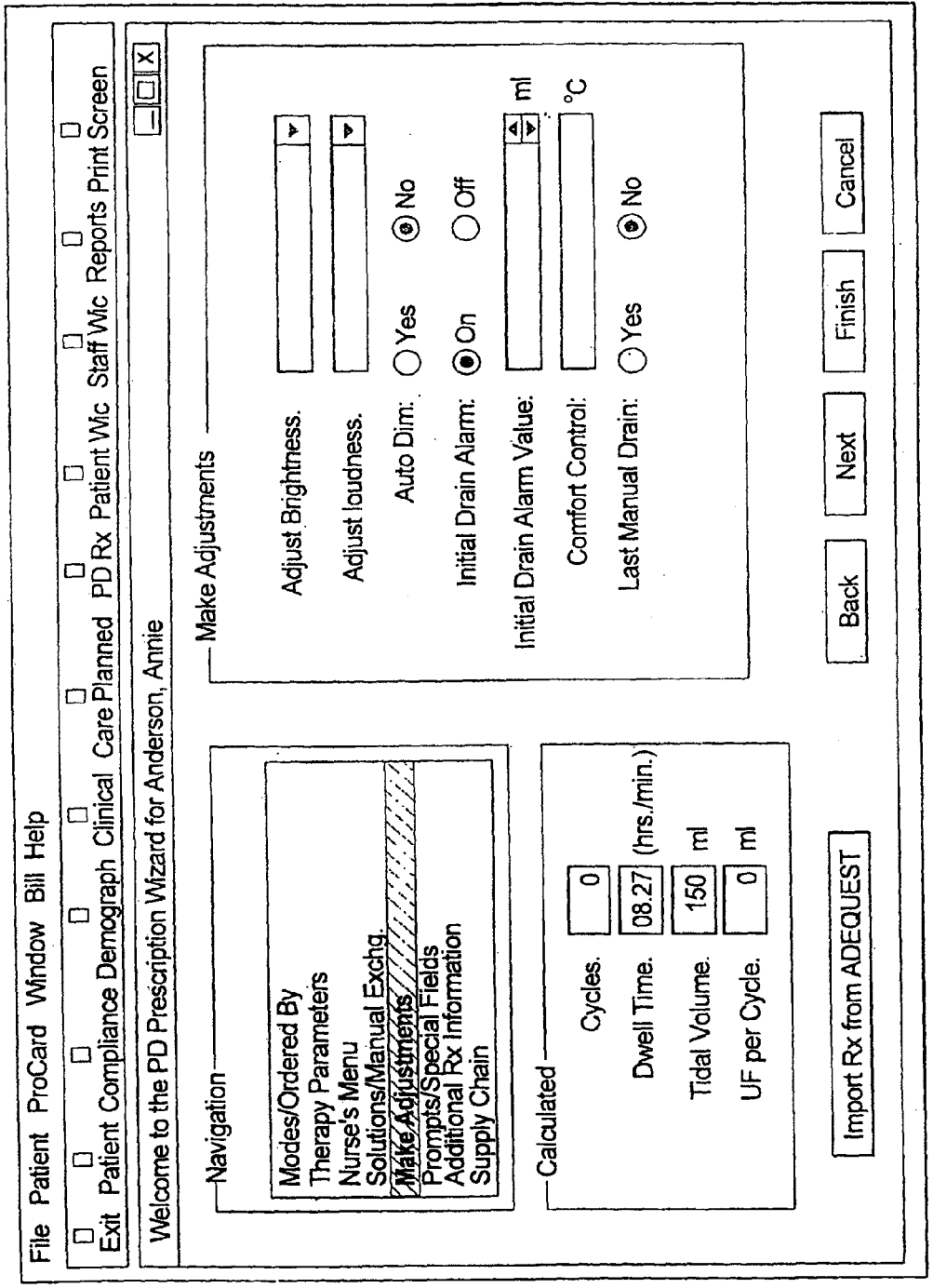
FIG. 31 illustrates a screen which enables a user to adjust information within the system in an embodiment of the present invention.
Figure 34:
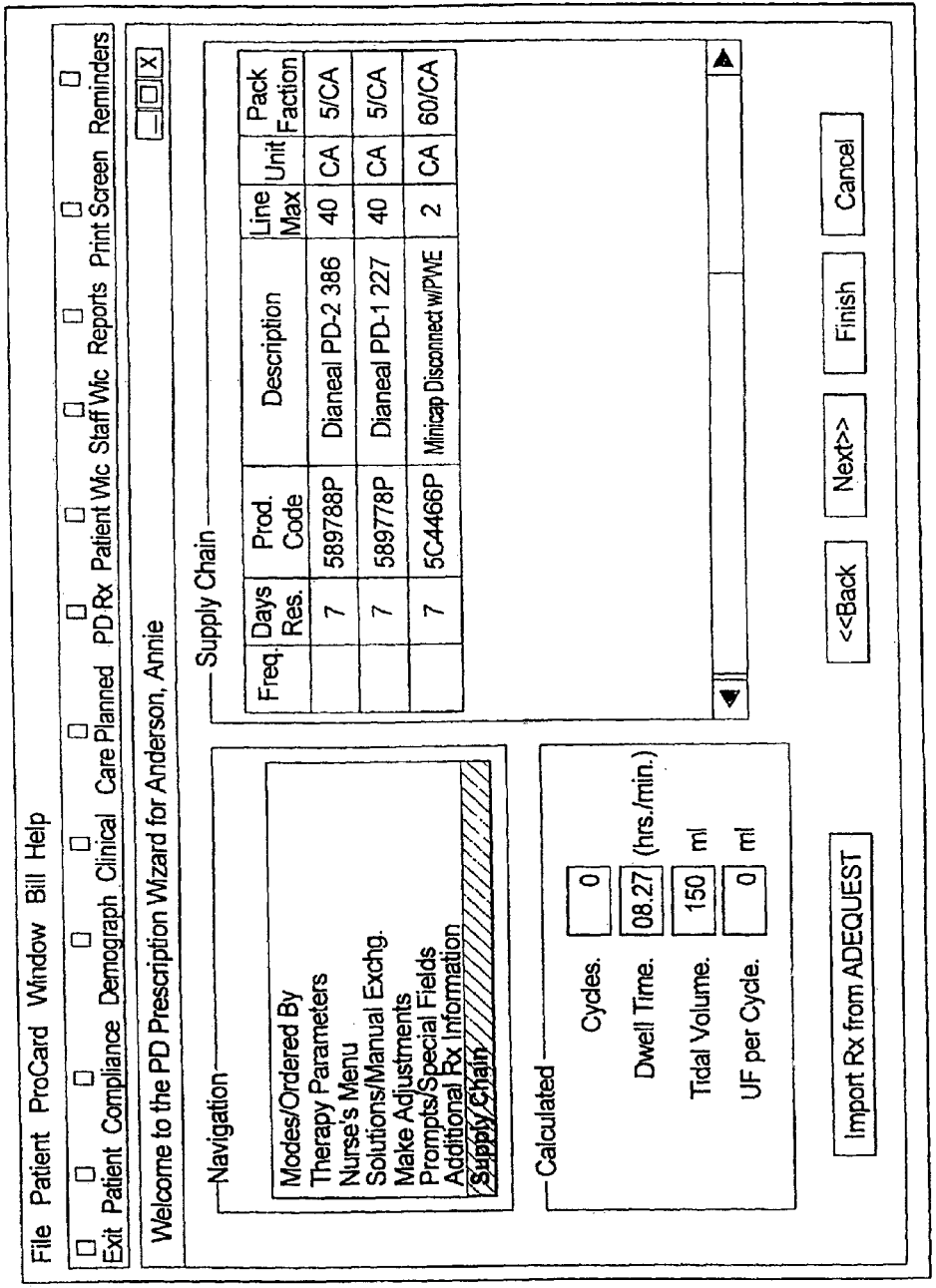
FIG. 34 illustrates a screen which contains supply chain information in an embodiment of the present invention.
Figure 35:
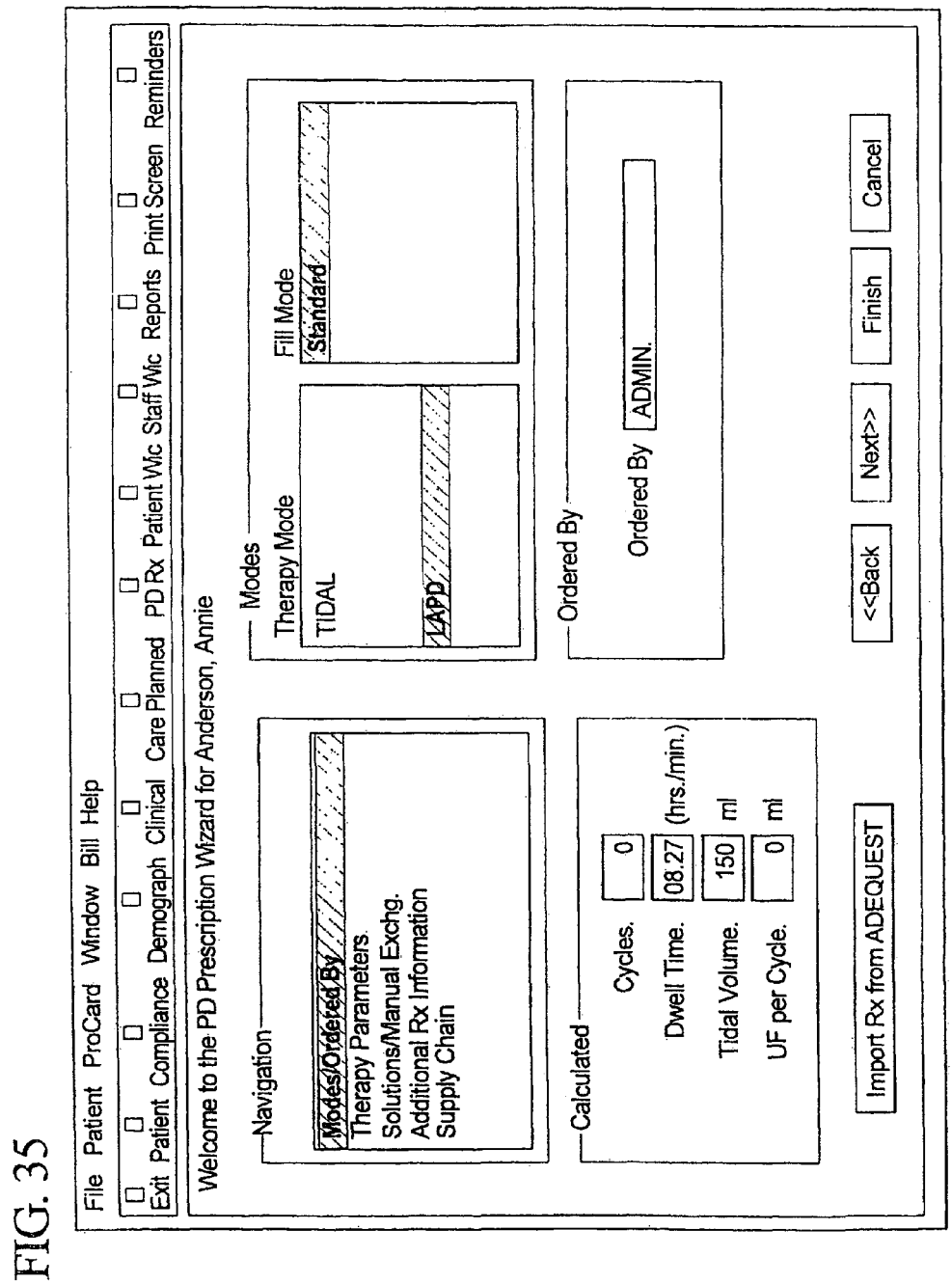
FIG. 35 illustrates a screen which enables a user to select a mode of therapy in an embodiment of the present invention.

Moreover, medication history may be maintained with use of the system and method of the present invention. The history and/or medication selected by the user and current medications for the selected patient may be displayed. The system and method of the present invention further provides a report engine that provides the ability to sort on any column; the ability to filter on any column; the ability to search for text strings within a remark field; the ability to move, hide, and/or re-arrange column; and the ability to hide a reports sections. FIG. 24 illustrates a screen that may prompt a user to identify the ability to add a column and prompts for making a column by word specific "bands." After a report is selected, sorts, additions or deletions may be affected. In addition, text may be added as illustrated by FIG. 25 within specific bands. Similarly, expressions may be added through a series of prompts within the screen. Fonts within any report may also be adjusted and modified through a font prompting screen as generally illustrated in FIG. 26. Font may be adjusted by font type, font style and/or font size for any report within the system.

As previously described, the system and method of the present invention may be executed on a computer within the home of a patient. The PC may be connected to an instrument via a serial connection. Alternatively, the PC may be connected to a modem and is capable of connecting to the Internet or intranet. After a PC in the home of the patient is turned on, the system and method of the present invention awaits a connection signal from the system operating within, for example, a clinic. The application automatically establishes a connection with the PC within the home of the patient via modem or TCP/IP protocol. An approved security algorithm communicates and receives the application through the system. The system and method of the present invention includes the ability to securely monitor home dialysis patients via a modem and/or the internet. The internet may be used to eliminate long distance charges and also add encryption on all data sent and received on the communication pathways.

The system of the present invention uses software to communicate with dialysis instruments within the home of the patient. The system via the software retrieves data from the instrument within the home. The system provides a secure way of communicating with the instruments in patient's home via modem and TCP/IP protocols. In addition, appropriate security is provided at the patient's side of the system. After the connection is established, the information from the patient's side may be transferred and may be received via the selected communication protocol from, for example, the clinic. The PC in the home of the patient may be connected to the instrument via a serial connection. For modem connections, however, a modem is attached to the PC. For TCP/IP connections, the PC is attached to a cable modem that is capable of reaching the internet/intranet.

The server for the system has two modules: one module for service and the other module for the controller. The service module provides low level communications with a network of instruments. The collected information may be made available via an interface for use by the system and method of the present invention. The service module also provides automatic collection of treatment data wherein the controller provides a graphic interface to monitor the functionality of the system. The controller may also provide for configuration management.

A third module may be used to provide security for the packets sent and received in the home of the patient. The third module may run on the PC in the home to manage the modem and TCP/IP connections between the instrument and the clinic. The software used at both ends of the connection adhere to Advanced Encryption Standard (AES) for packets sent and received in the home of the patient.

The system provides control and/or security for modem connections to the patient. Commands may be provided for a modem port to be assigned to a particular telephone number, status of the connection may be queried, and the connection may be terminated. The system may further provide control for TCP/IP connections to the system of the patient. Commands provide for a TCP/IP resource to be assigned to the connection, status of the connection to be queried, and the connection to be terminated. The interfaces for the control of the connections may be available via screens provided by the system and method of the present invention.

The controller further provides configuration of the machine resources for the system. The controller may write to the registry with the appropriate resource type: modem, in-center, or TCP/IP. As a result, the server may be configured for any of the three resource types. Source maps may store this configuration information, and interfaces may expose information to the system and method of the present invention. The demographics window of the system and method of the present invention allow a user to configure a home patient for a modem or TCP/IP connection. A modem checkbox in the screen of the demographics window populates a listbox control with "modem" and/or "TCP/IP" in the checkbox. The control is automatically enabled when the user selects "home hemo connection" within the category list of types of treatment.

The system and method of the present invention allows a user to assign a home patient to a modem or TCP/IP station. The menu and the window may be changed from real time-connect/disconnect modem to a full time, home hemo connection. After a connection is made to the system within the home of the patient, real time monitoring of the home system may be provided in the same manner as a machine used at a dialysis center. If a connection is lost, the network window may indicate the same to the user. A home station that loses a connection may be sorted to the top of a list beneath any other stations which may have alarms associated with the home station.

To establish modem connections, serial connection is made between the instrument and the PC in the home of the patient. The modem may be set to auto answer and may be connected to the PC. The patient's system may be started on the PC, and a port may be opened to the modem to await a call from the clinic.

Within the clinic, the system 1 may wait for the user to begin the call to the home of the patient. Using a home hemo connection window, a call from the clinic may be made using the modem connection to the PC in the clinic via telephone lines directly to the patient's home. The modem in the home then answers the call, and the client's system is connected to the clinic system. Packets that may be transferred between the connection are encrypted using AES.

After the call has ended using the connection window, the modem in the home returns to auto-answer with a port open. At this point, the patient's system is ready for another incoming call. The modem in the clinic may then establish another outgoing call to another patient.

Similarly, TCP/IP connections to the home of the patient are established by the serial connection made between the instrument and the PC in the home of the patient. The setup of the client's system in the home includes the static IP address and port number of the TCP/IP server system that runs within the clinic. The patient's system automatically attempts to connect to the clinic using the static IP address and port number via the cable modem across the internet. A number of times for each attempt may be configurable, and a default may be established for the number of times.

Within the clinic, the system waits for the user to begin the connection to the specific home of the patient. Using the connection window of the system 1 and method 100 of the present invention, a connection attempt from the clinic is made to the system within the clinic. In the system, a switch may respond to the connection being established from the patient's home. Through this connection, a new thread is spawned in the system at the clinic to continue the connection. As a result, the main connection thread is made available to respond to other connection attempts made by other home patient TCP/IP clients. Circuits that may be passed between this connection may also be encrypted using AES.

After the connection is terminated, the patient's system resets its connection thread and begins attempts to connect to the clinic's TCP/IP server within a specific time frame, i.e. every thirty seconds, which may be configurable and set for the patient. The system may reset its switch preventing attempts to connect the same from the patient's system, and all subthreads used in the terminated connection may be dropped.

The system 1 and the method 100 of the present invention may further guide a user to create PD prescription and/or supply chain orders. To this end, navigation and streamline processes create patient prescriptions based on the patient's therapy mode may be provided. The system may step a user through logical groups of data elements to create the new PD prescription. This example is based on the presumption that the patient received a previous prescription. The previous prescription data may be used as a default, and the user may navigate among the various steps and save a new record at any time. If this prescription is the first prescription for the patient, the first prescription for a different therapy mode fill mode combination and the appropriate machine default values may be set. The user may complete each step sequentially and save the record after completing the final step.

In a first step, the user selects a therapy mode, fill mode, and an ordering physician. Selection of modes at this point establishes defaults limits for subsequent steps. As a result, work flow inconvenience may be eliminated when the user defines the fill mode changes. As a result, previously entered data may be reset to the machine default for the new fill mode. The user may then be required to return to the first tab and start over. FIGS. 27-35 illustrate the steps that the system 1 and the method 100 of the present invention implement to prompt a user to effect the prescription fill and recording of the prescription within the system 1 and method 100 of the present invention.

As will be further described, the system 1 and the method 100 of the present invention enables a user to digitally assign a patient's prescription and supply chain components and/or send to the supply chain website or otherwise received at the supply chain. As a result, a physician's digital certificate acting as an actual signature is provided for the prescription. To this end, an interface may be provided between the system 1 of the present invention and various supply chain systems to effect home patient ordering and delivering of prescriptions. Each system may include a variety of applications and/or interfaces. First, country specific rules may be provided in an application to enter and maintain rules specific to each country at which a supply chain may be used to effect completion and/or delivery of a prescription. Data maintained in the application may include a country identifier, whether a prescription is required for an order to be generated, whether a digital signature is required on a prescription, a level at which a digital signature may be required, and whether a physician identification exists.

Another application may include unit registration and may allow a dialysis center or a supply chain to register and maintain information unique to their business. To this end, a web-based front end may be provided to register and manage unit specific data. Data entry may be used for initial sign-up to the supply chain. The front end may also prompt the user to set up the information and download a list of patients associated with the unit. An interface may be provided through the supply chain systems to retrieve a list of valid entities associated with the system. Further, an interface with the supply chain systems may be provided to retrieve a list of positions associated with the center. In addition, an interface with the supply chain systems to retrieve a list of patients associated with the center may also be provided with the unit registration application.

A patient enrollment interface may be provided that allows for the automated initiation of new patient enrollment subsequent to update of the supply chain systems. A patient enrollment interface may include updating supply chain address book information regarding patient enrollment. A module may add new patient name and address information to the supply chain database. Further, the patient enrollment interface may include update supply chain patient activity information that may add information to the supply chain database that may be necessary to complete a transaction. In addition, the patient enrollment interface may update supply chain patient demographic information available at the time of enrollment and maintained in the supply chain system. Further, initial supply chain prescriptions may be created within a supply chain system. Initial orders may be generated and acknowledged using predefined distribution methods and recipient lists that acknowledge that the order was created.

A product prescription management interface may also be provided. The automated processing of updates to patient's product prescriptions in the supply chain system may be performed from initiated events. An inventory management and replenishment order generation interface may be provided for the automated updating of patient inventory in the supply chain system from transactions previously initiated or from, for example, an external hand-held device. A replenishment order and order acknowledgment may be automatically triggered, at least upon defined inventory levels.

Still further, a patient management interface may be provided to update patient information in the supply chain system from previous transactions. Patient address book information, patient gain/loss information and patient demographic information may be updated and the interface may be built upon the patient enrollment interface. Synchronization between the supply chain and previous systems may be ongoing and allow changes initiated in the supply chain system to be communicated. The interfaces, patient name and address changes, mode of treatment changes, patient and activation and product prescription changes may also be provided The system of the present invention may download formatted transactions to a transmission layer for eventual processing in a system at the supply chain. Formatted transactions may be imported from the transmission layer for updating of the database. The transmission layer may facilitate processing of transactions between the supply chain system. An application server and associated code for the web application is built as a front end to the transmission layer. A database facilitates the storage of data as the data is passed through the transmission layer. Procedures may be stored and/or activated to initialize, extract, format and transmit data in and out of the transmission layer. A standardized method for formatting data passed to and from the transmission layer may be provided, i.e. SNTP, ASCII, or the like.

The supply chain system provides back-end processes to receive and send data to and from the transmission layer. In the supply chain system, file formats may be used in the transmission of data back and forth to the transmission layer; to schedule jobs that may invoke programs that store procedures to receive data from the transmission layer; to apply supply chain business rules and update supply chain databases provided; and to schedule jobs that may invoke programs and stored procedures to extract data transactions from the supply chain databases and send them to the transmission layer.

Figure 36:
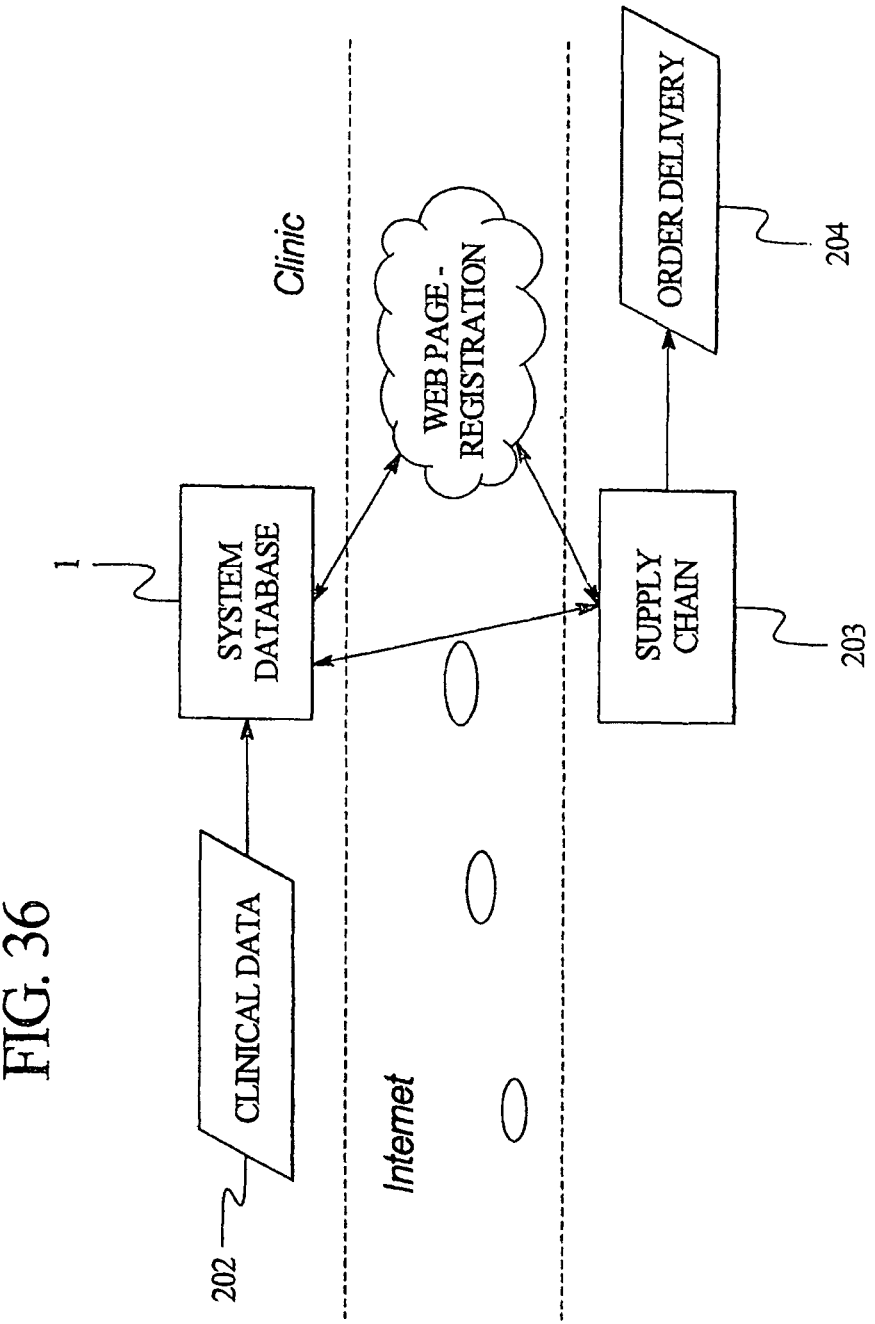
FIG. 36 illustrates a block diagram of supply chain integration in an embodiment of the present invention.

FIG. 36 generally illustrates the supply chain integration between the system 1 via the internet to the point at which supplies are provided and/or sent for delivery. To this end, the system 1 includes clinical data entry 202 to the system 1 of the present invention via the internet or directly to the supply chain 23 to provide information necessary to effect order delivery, as shown at 204. To enroll a patient to the supply chain, such as a home hemodialysis patient, a healthcare professional, a doctor, or the like enters patient treatment information into the system 1 as well as patient and demographic information. Further, a prescribing physician is assigned to the account including "bill to" information. The patient prescription is input which may include capture of an electronic signature. A patient account number may then be assigned, and information regarding the patient may be recorded including the prescription information, or the demographic information of the patient. Then, the patient initial order may be generated. The supply chain patient enrollment and prescription transaction may then be submitted to the supply chain via the Internet or via infrastructure supported at the location of the supply chain.

Figure 37:
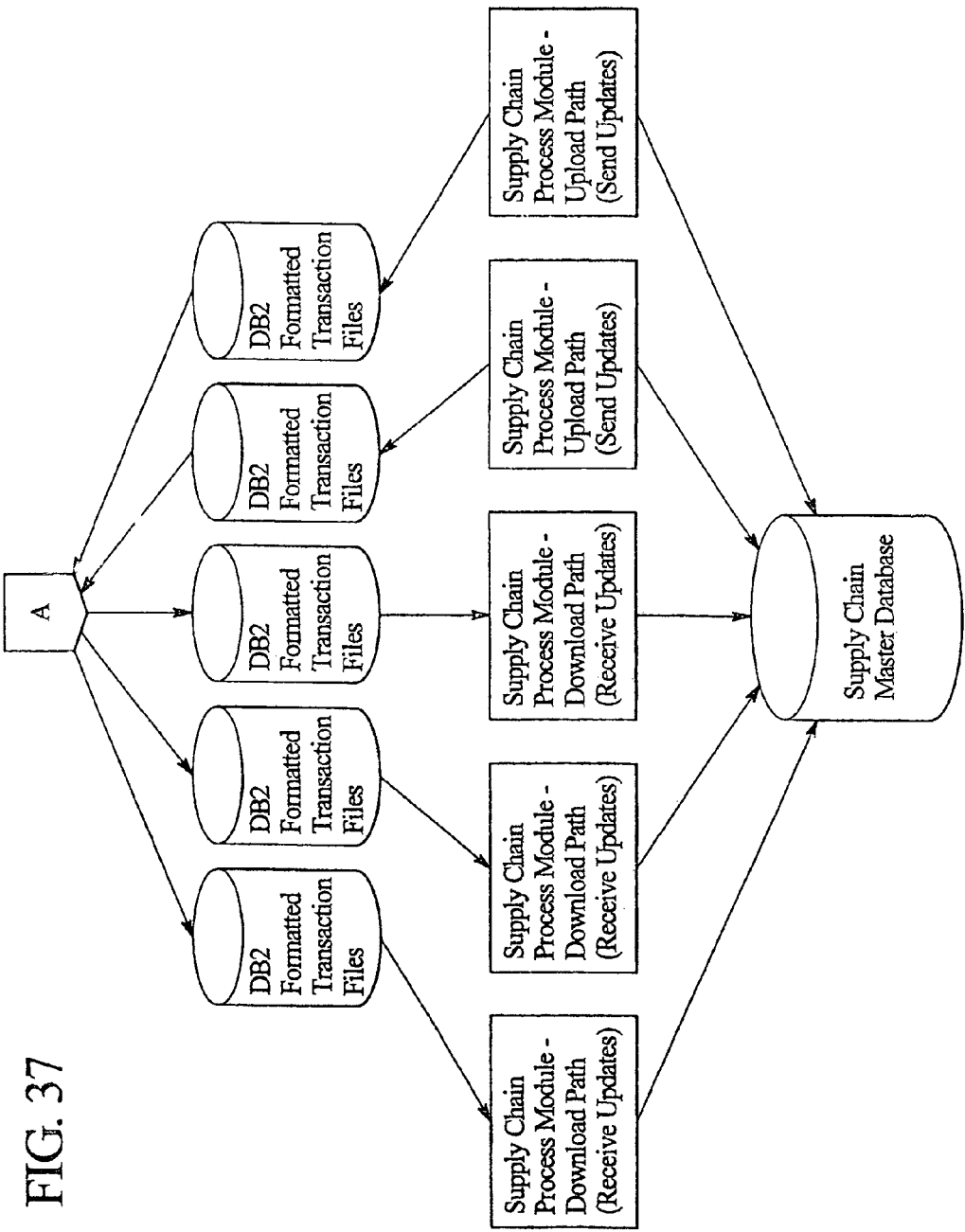
FIG. 37 illustrates user requirement specifications for effecting delivery of prescriptions and prescription information via a supply chain in an embodiment of the present invention.
Figure 38:
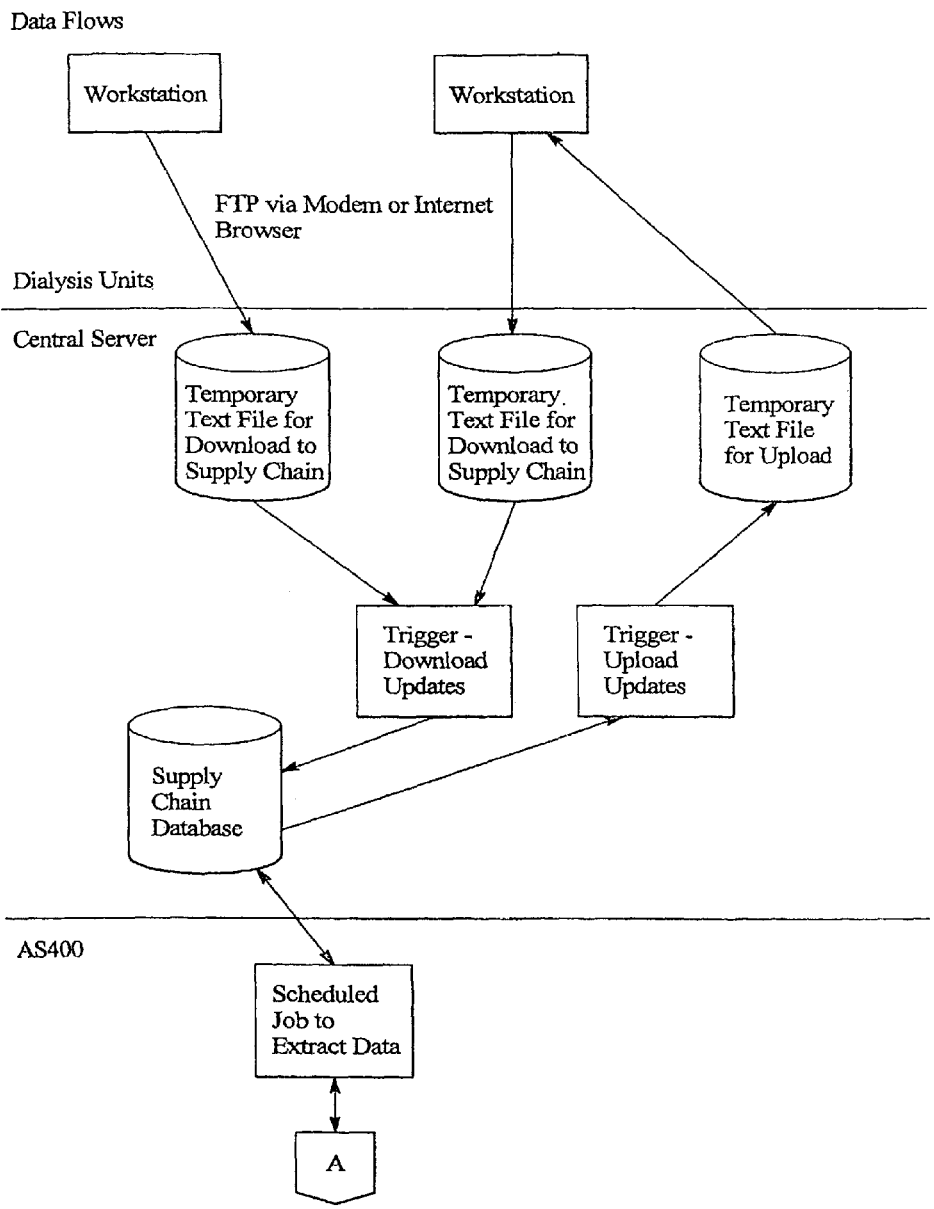
FIG. 38 illustrates user requirement specifications for effecting delivery of prescriptions and prescription information via a supply chain in an embodiment of the present invention.

FIGS. 37 and 38 generally illustrate user requirement specifications for effecting delivery of prescription and prescription information via a supply chain.

FIGS. 39 to 49 generally illustrate the program architecture for the system 1 and method 100 of the present invention. The architecture shown and described with reference to FIGS. 39 to 49 shows a process from which Chronic Kidney Disease (CKD) patient may be evaluated by a multi-disciplinary team providing care to the patient.

Figure 39:
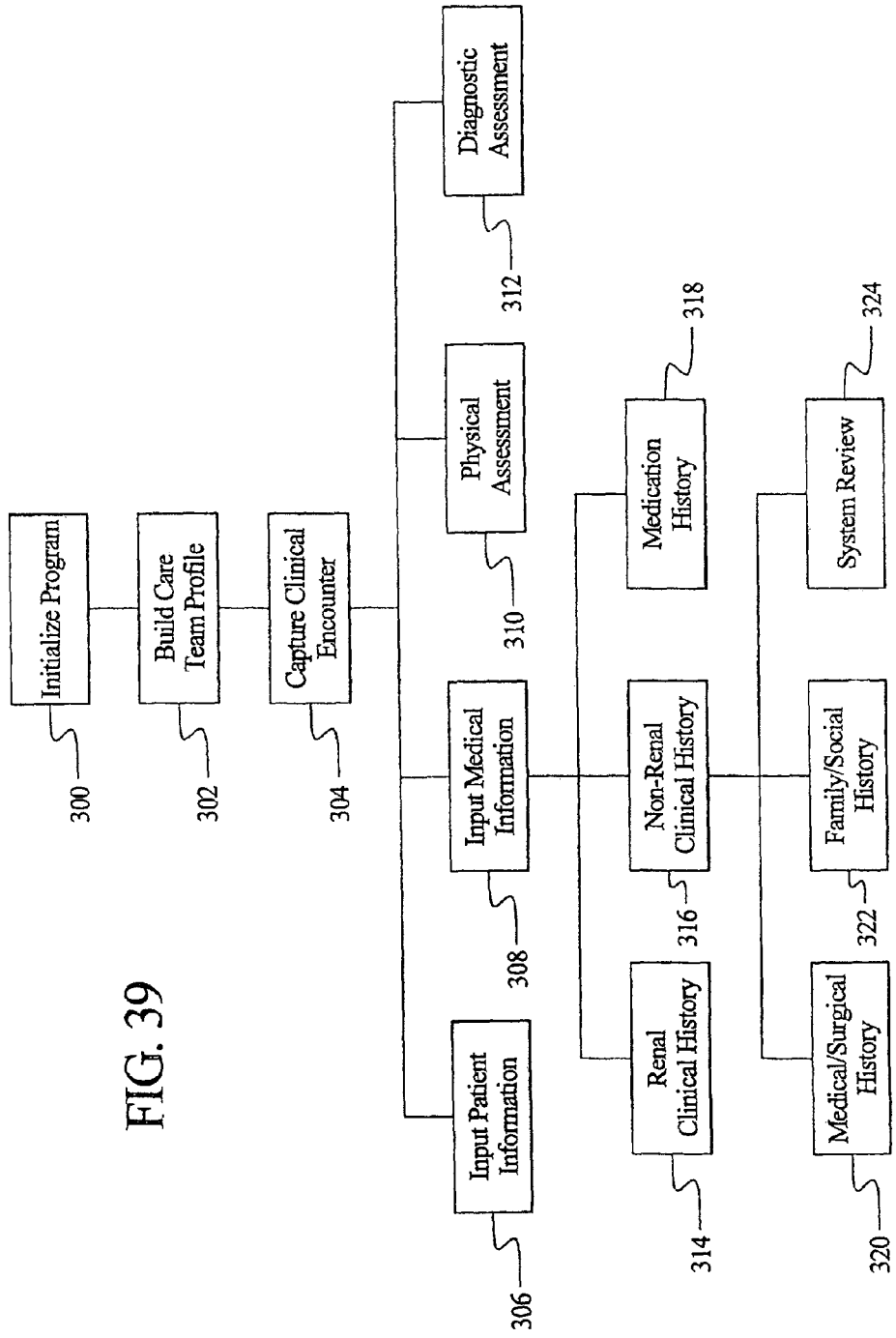
FIG. 39 illustrates a block diagram of a method for capturing a clinical encounter in an embodiment of the present invention.

To this end, as illustrated in FIG. 39, a program may be initialized at step 300 to allow the team at a renal facility to be entered to identify the individuals who may provide care to the patient. Individuals become part of a selected care team as identified at step 302. At that time, a clinical encounter, as shown at step 304, follows patient assignment to a physician. The clinical encounter includes the input of patient information as shown at step 306, the input of medical information as shown at 308, a physical assessment as shown at step 310, and a diagnostic assessment as shown at step 312. The input medical information may include a renal clinical history as shown at step 314, a non-renal clinical history as shown at step 316, and a medication history as shown at step 318. In addition to the non-renal history, that information may be further subdivided into medical surgical history as shown at step 320, family/social history as shown in step 322, and a system review as shown at step 324.

Figure 40:
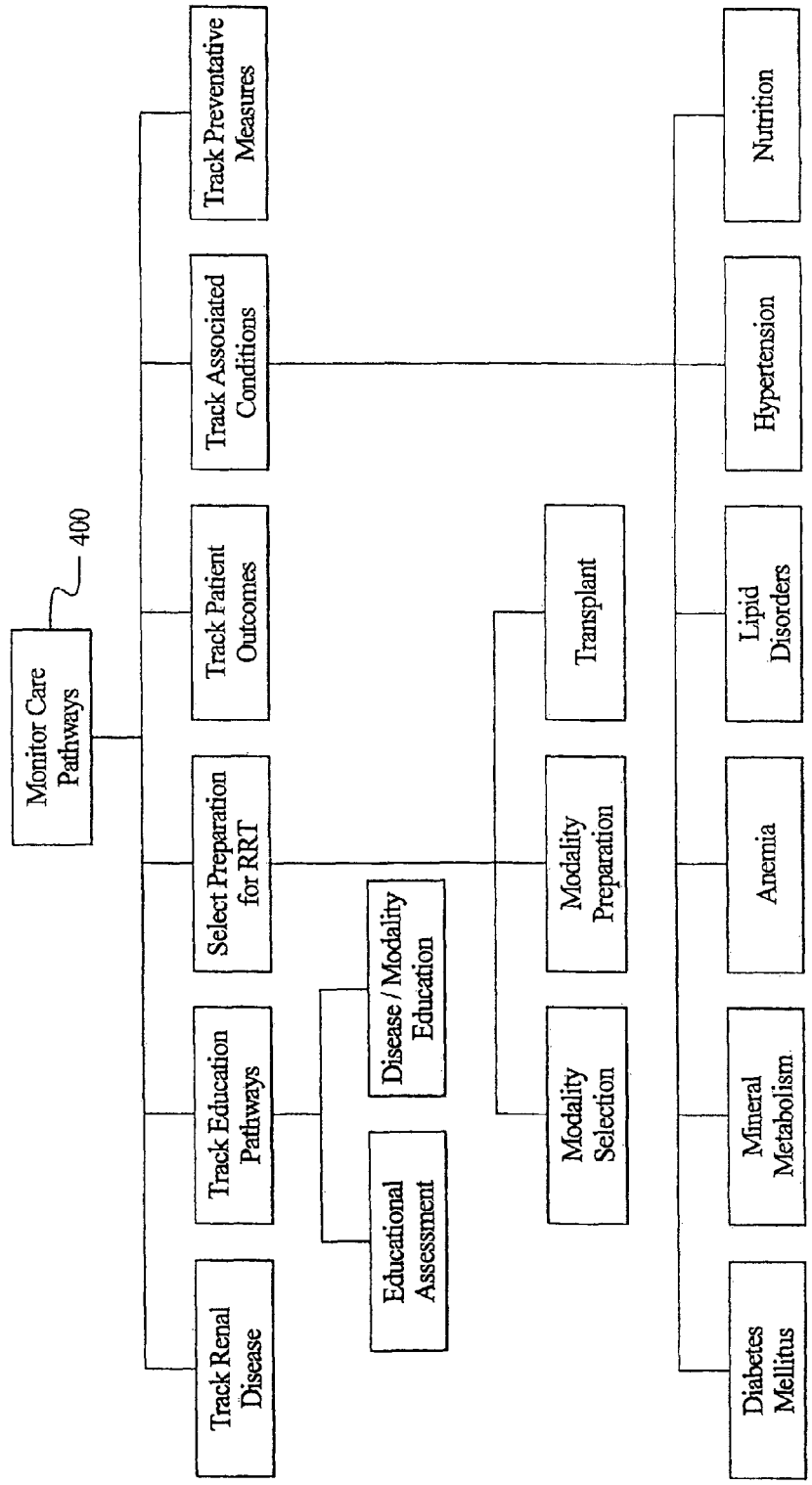
FIG. 40 illustrates a block diagram of a method for monitoring care pathways in an embodiment of the present invention.
Figure 41:
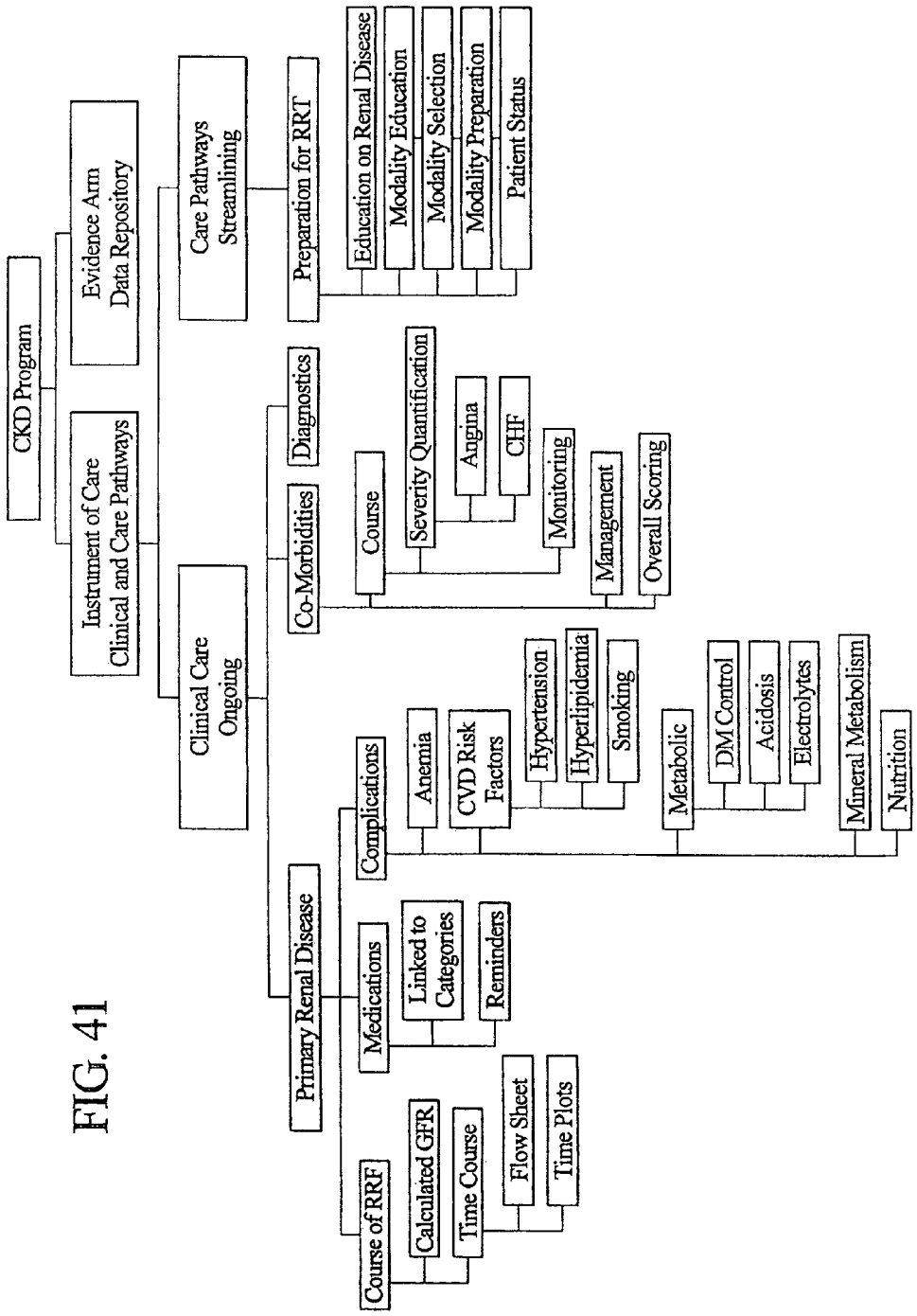
FIGS. 41-49 illustrate block diagrams of tracking that occurs through the clinical and care pathways for the dialysis patient in an embodiment of the present invention.
Figure 42:
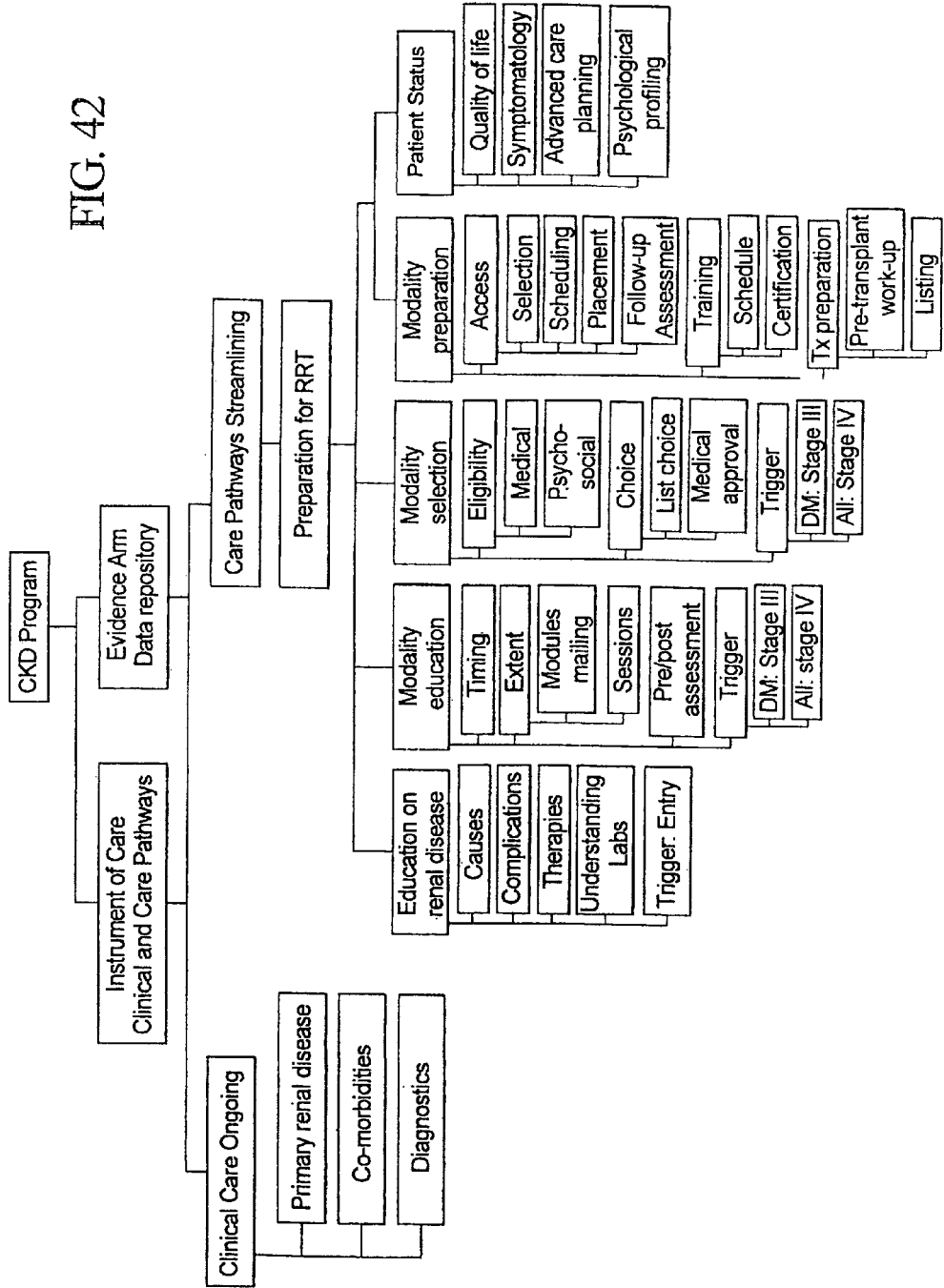
Figure 43:
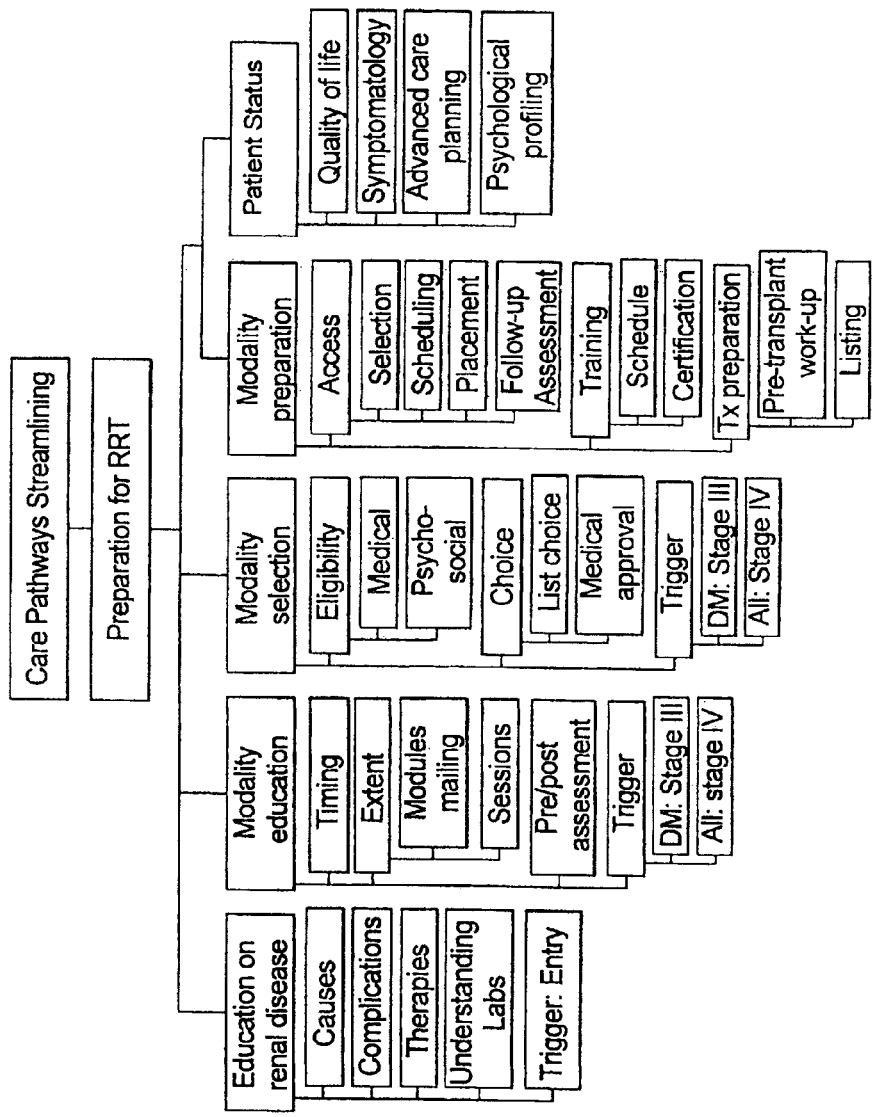
Figure 44:
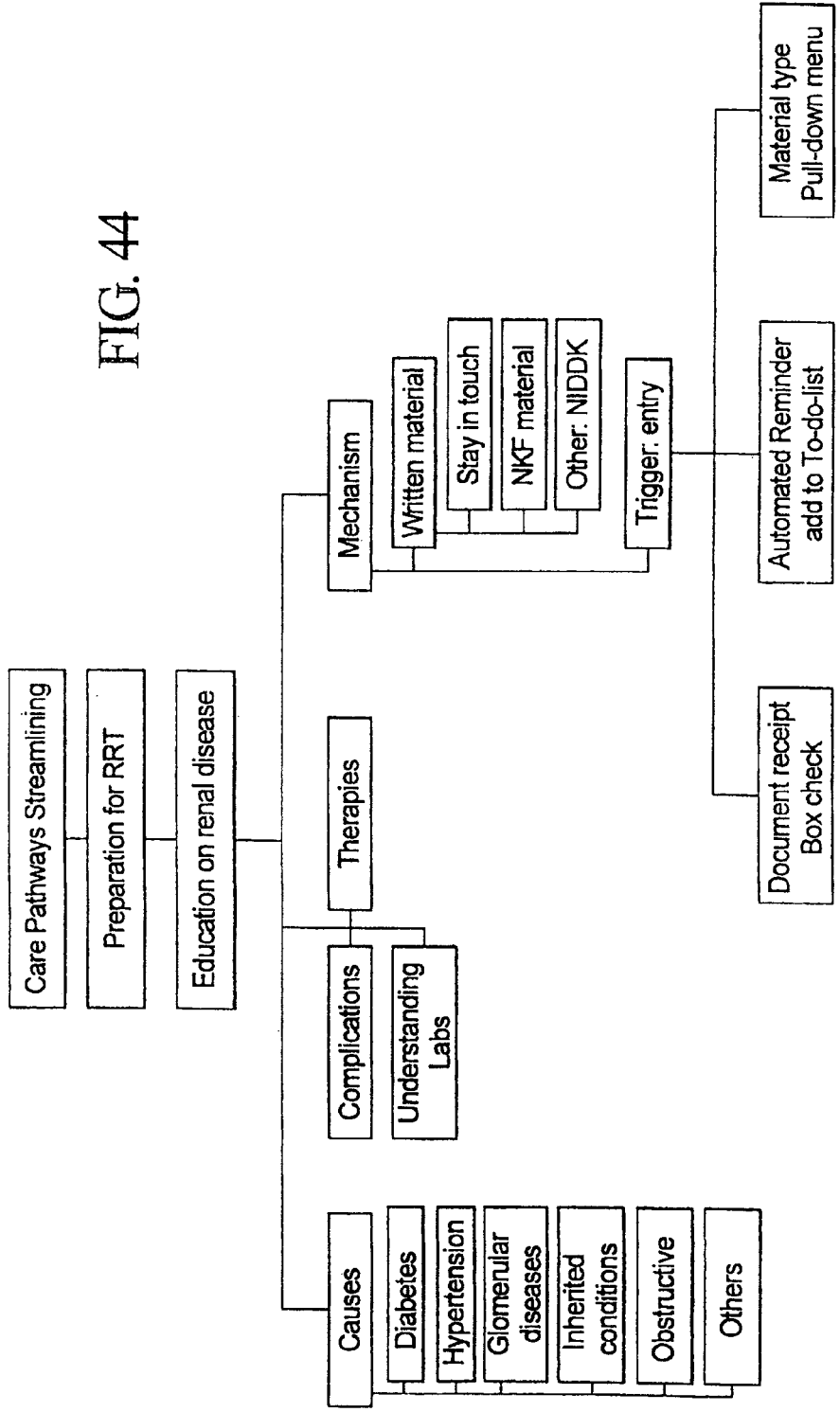
Figure 45:
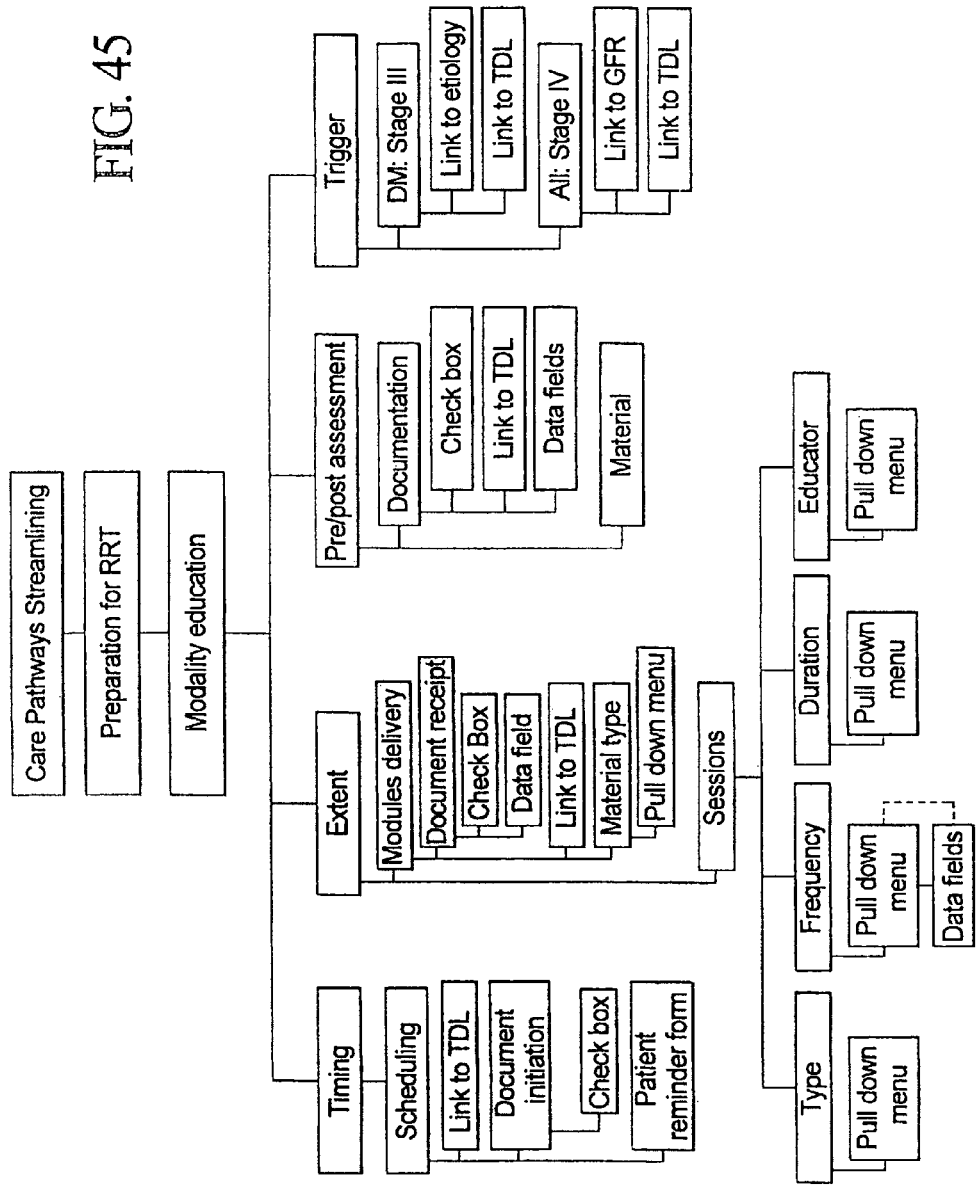
Figure 46:
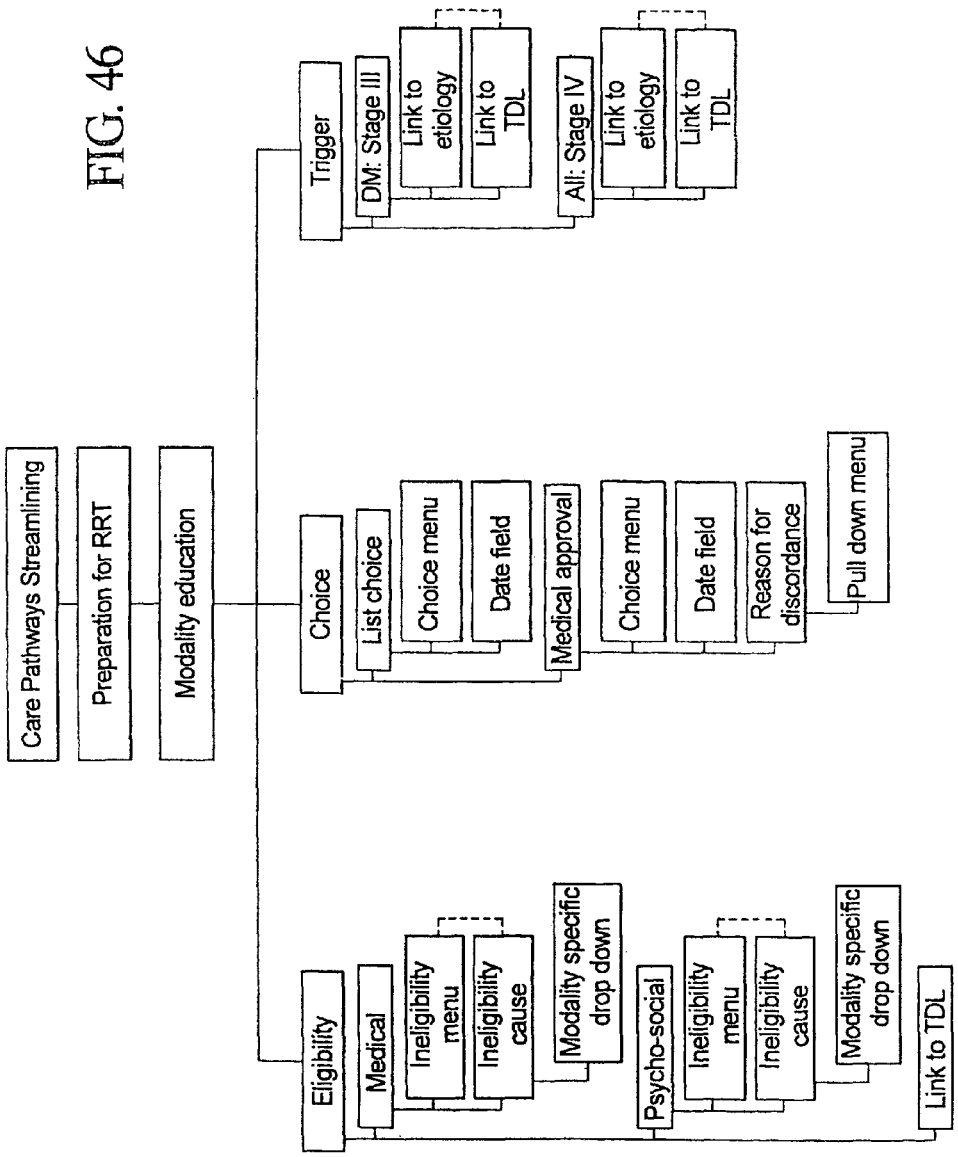
Figure 47:
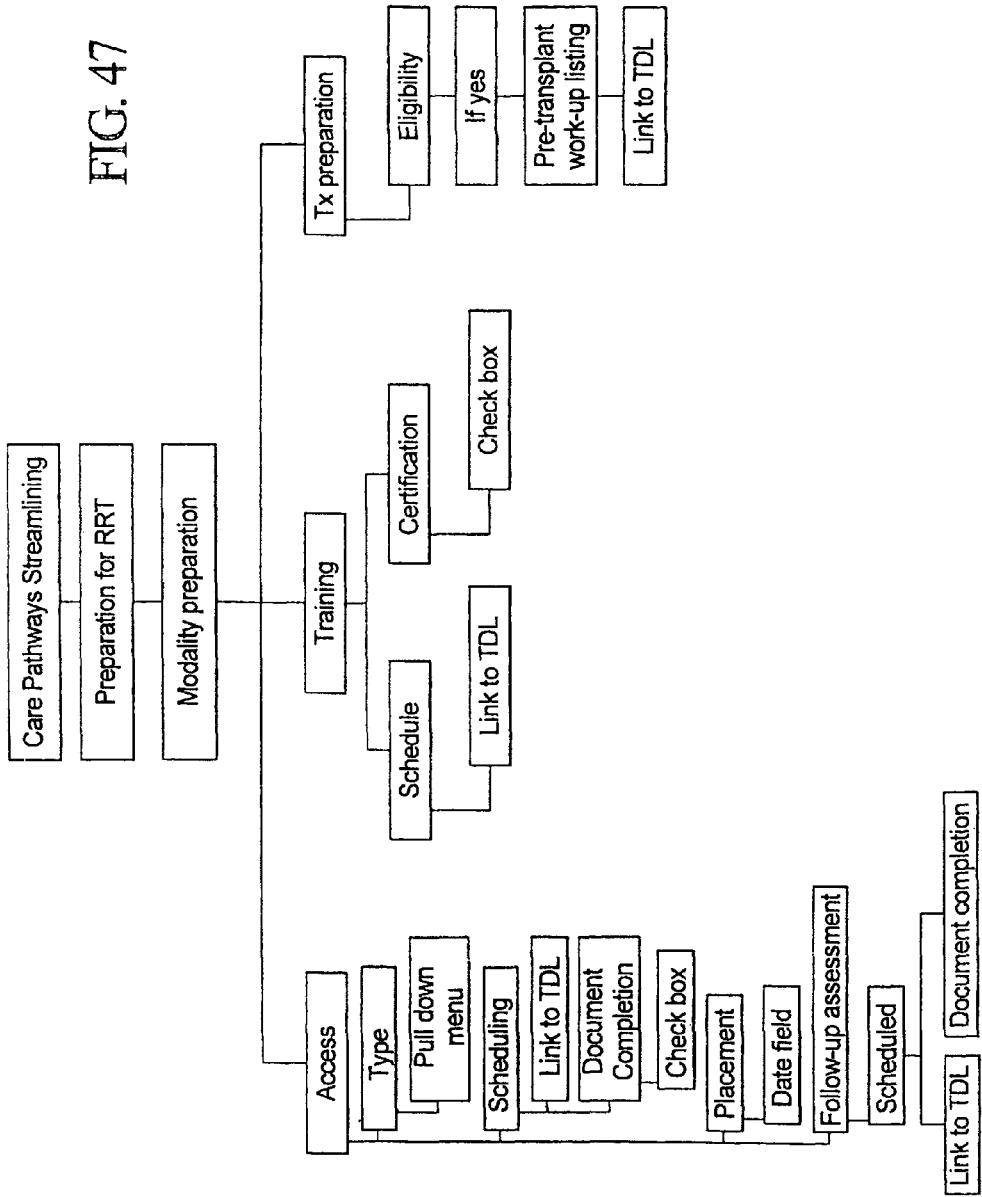
Figure 48:
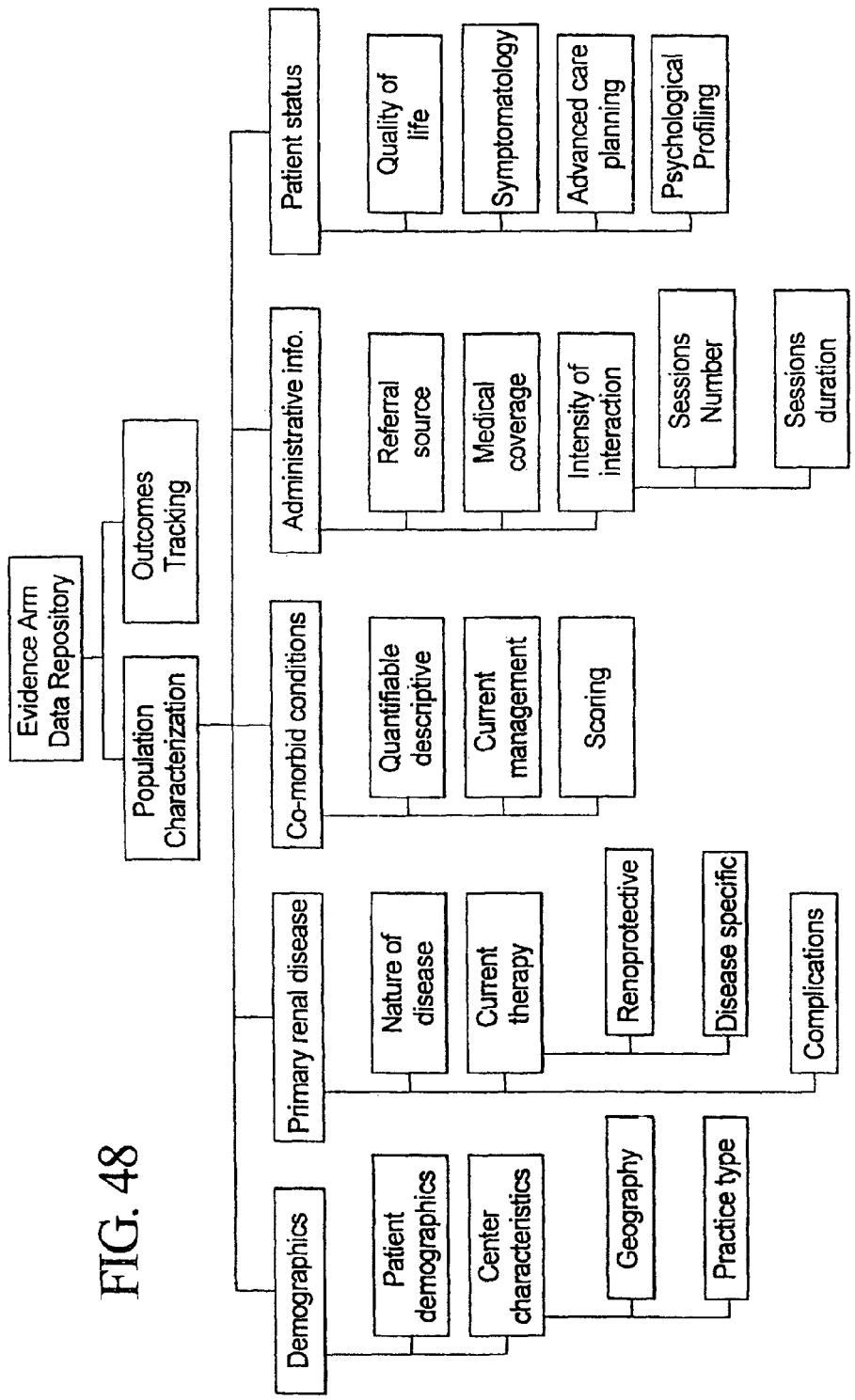
Figure 49:
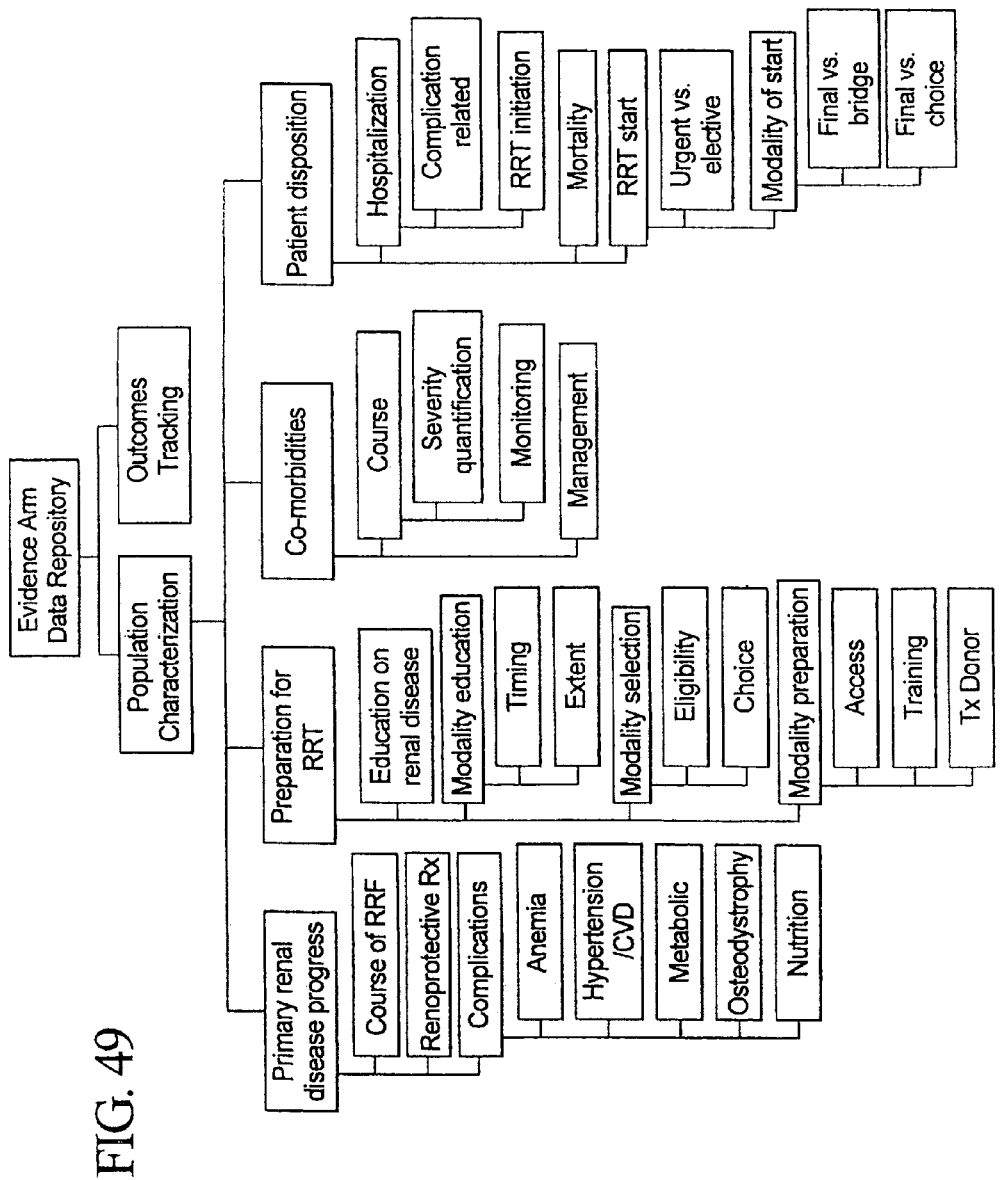

Monitoring of care pathways occurs as shown in FIG. 40 at step 400. Monitoring of care pathways takes pertinent aspects of clinical care of a renal patient into consideration. Each aspect may be reviewed and the needs and/or care of the patients as pertaining to a particular disease state, i.e. anemia, mineral metabolism, and the like may be evaluated. Data may be imported from other areas in the system that apply specifically to the problem addressed. For example, to evaluate anemia, lab values and/or medications which pertain to the doctor or physician or other healthcare decision relating to anemia are imported to a screen directed to anemia. Aspects of patient education may also be included to enhance delivery of education and patient choices as a result of the education.

FIGS. 41 to 49 illustrate the specific tracking that occurs through the clinical and care pathways for the dialysis patient. Each of the clinical and care pathways and their respective program descriptions as generally illustrated in FIGS. 41 to 49 will be more clearly described with reference to the subsequent description regarding each of the pathways.

Figure 50:
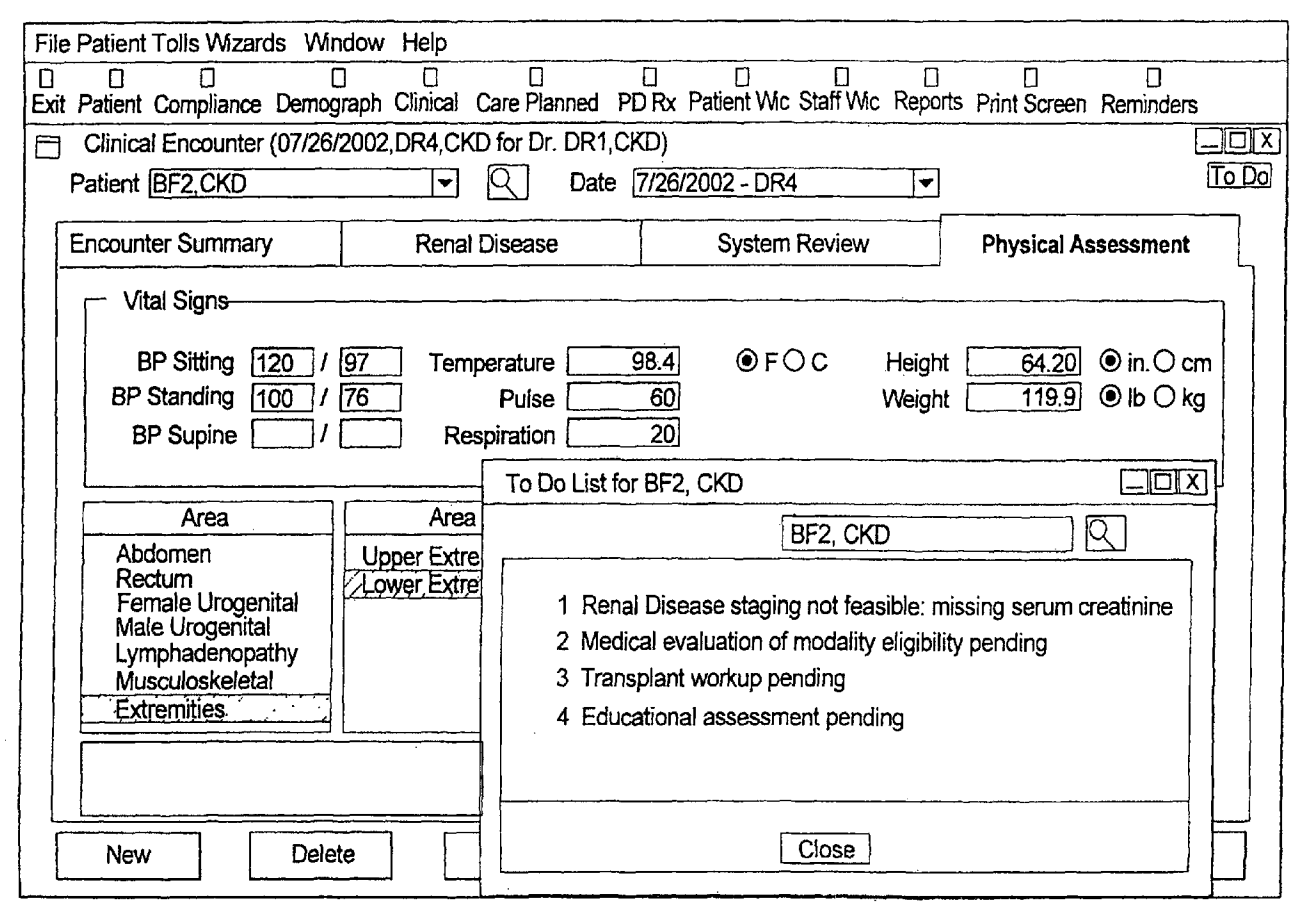

The system 1 and the method 100 of the present invention may also create a "to-do list" indicative of any areas have not been completed. The "to-do list" at a center may be created which may identify a patient or patients that may not have received one or more aspects of care at a particular level or levels of renal function. For example, a list of patients who have reached stage 4 of renal failure and who have not been educated on dialysis and transplanting options may be generated on a "to-do list". FIG. 50 generally illustrates a screen that pops up as a reminder regarding specific items that must be completed in a "to-do list" format.

An encounter summary screen may also be provided as a summary of medical history and current assessment and data on a patient on a particular date. The encounter summary represents a "snap shot" of a visit of the patient with a particular doctor or medical professional on a specific date and time. The encounter summary may include categories of information relating to renal disease history, medications, allergies and physical assessment. These categories of information may be entered in subsequent pages and may then be printed on the encounter summary page as a summary. The information is historical in nature and may be saved for each visit of each patient. In addition, while previous dates may be chosen in the field after a selection, a summary for the date may be shown. The remaining figures should be considered in conjunction with the architecture shown and described with reference to FIGS. 41 through 49.

A renal disease pathway screen is shown which provides a summary for imported information including renal diagnosis, performed biopsy, lab values and medications pertinent to renal disease treatment or prevention or that which delays the progression of renal disease. The renal disease pathway brings the renal disease related information to a single screen which a physician may review to treat or otherwise evaluate renal disease. The medication list may be viewed by selecting medications on tabs available with the screen. A hyperlink may be provided to link to published guideline sites for treatment of renal disease which may be obtained by selecting the guidelines prompt. The information provided on the clinical pathway for renal disease may include information imported from other parts of the system collected that may be appropriate for the renal disease clinical pathways page. The lab information may be input into the system through a lab interface as previously described and grouped according to the appropriate pathways, such as the renal pathway. The medications associated with the clinical pathway for renal disease may display a medications window and may provide access to the functionality set forth to describe the medications/allergies tabs for a clinical encounter. A guidelines button launches a pop-up dialogue with guidelines for this pathway and links to specified guideline documents. Further, tabs may be provided for renal disease, anemia, diabetes mellitus, mineral metabolism, hypertension, lipid disorders, nutrition and preventative. CKD stage calculations are provided with stage 1 for GFR.gtoreq.90 wherein the GFR calculations are provided in the renal disease tab. Stage 2 is calculated with 60.ltoreq.GFR<90; stage 3 has 30<GFR or <60; stage 4 has 15.ltoreq.GFR or <30; stage 5 has GFR<15. Calculated fields are present on the-renal pathways window, such as, serum chemistries which may display an ion gap, corrected calcium or creatinine clearance. The system 1 and the method 100 of the present invention verify that all units are using the same measure, or the units are converted. Preferably, the nature of the renal disease may be displayed as information from the most recent clinical encounter, and any information from the previous encounter is automatically re-worded to the current encounter.

Figure 52:
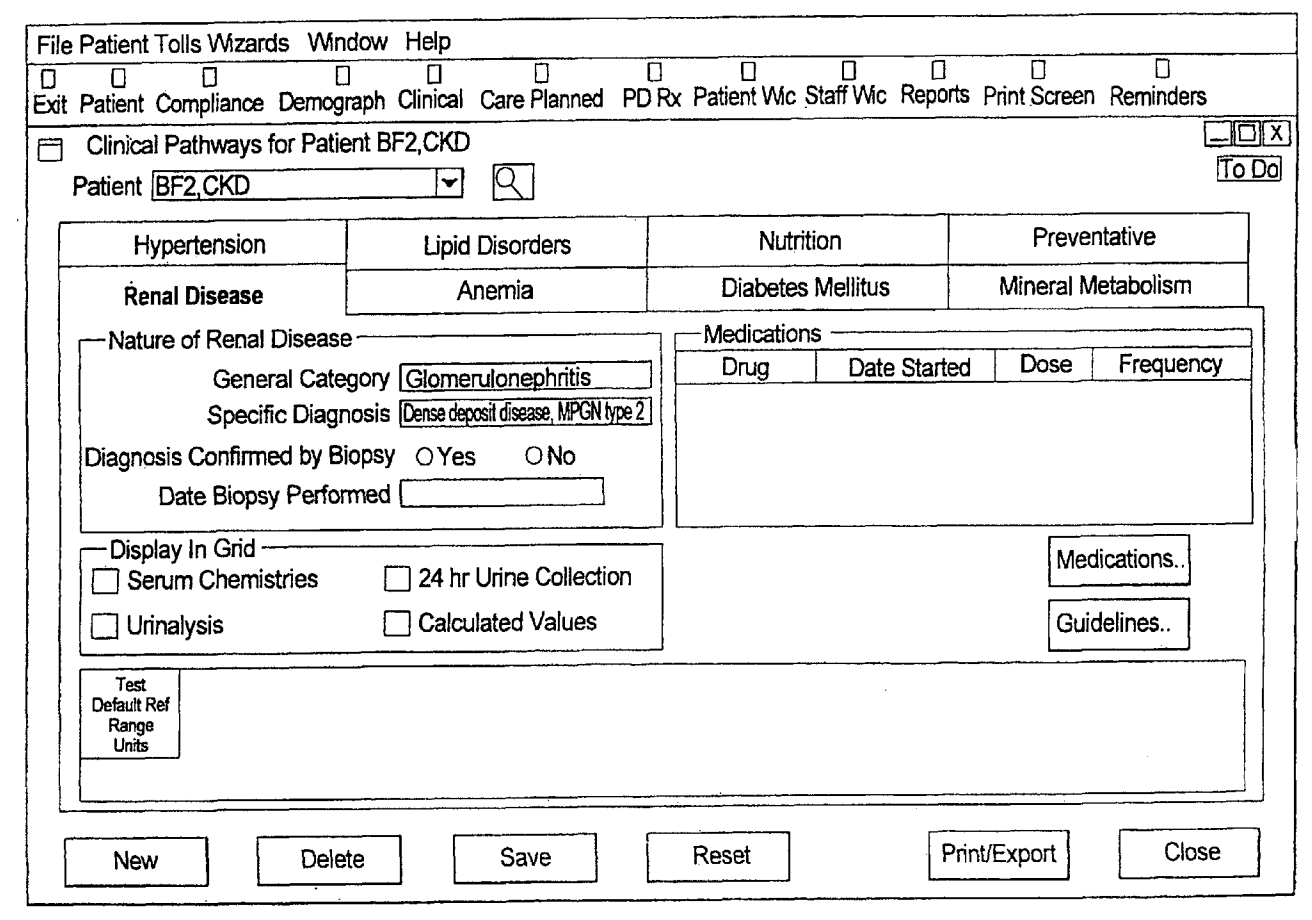
Figure 53:
FIG. 53 illustrates a screen containing a diabetes mellitus pathway in an embodiment of the present invention.

Referring now to FIG. 53, the diabetes mellitus pathway is generally shown with the screen illustrated in FIG. 53. The pathway is a page of imported information and/or manually entered information pertaining to diagnosis and treatment of diabetes mellitus (DM). The imported information may include lab values and medications used to diagnose or treat DM. Manually entered information may be provided to assist with information related to the prescription of DM treatment. In addition, information regarding the patient in treatment, such as glucose monitoring, exercise, diet and other DM related issues including foot care may be provided. The same functionality exists with the tabs in the screen of FIG. 53 as that described with respect to the renal disease clinical pathway in FIG. 52.

Figure 54:
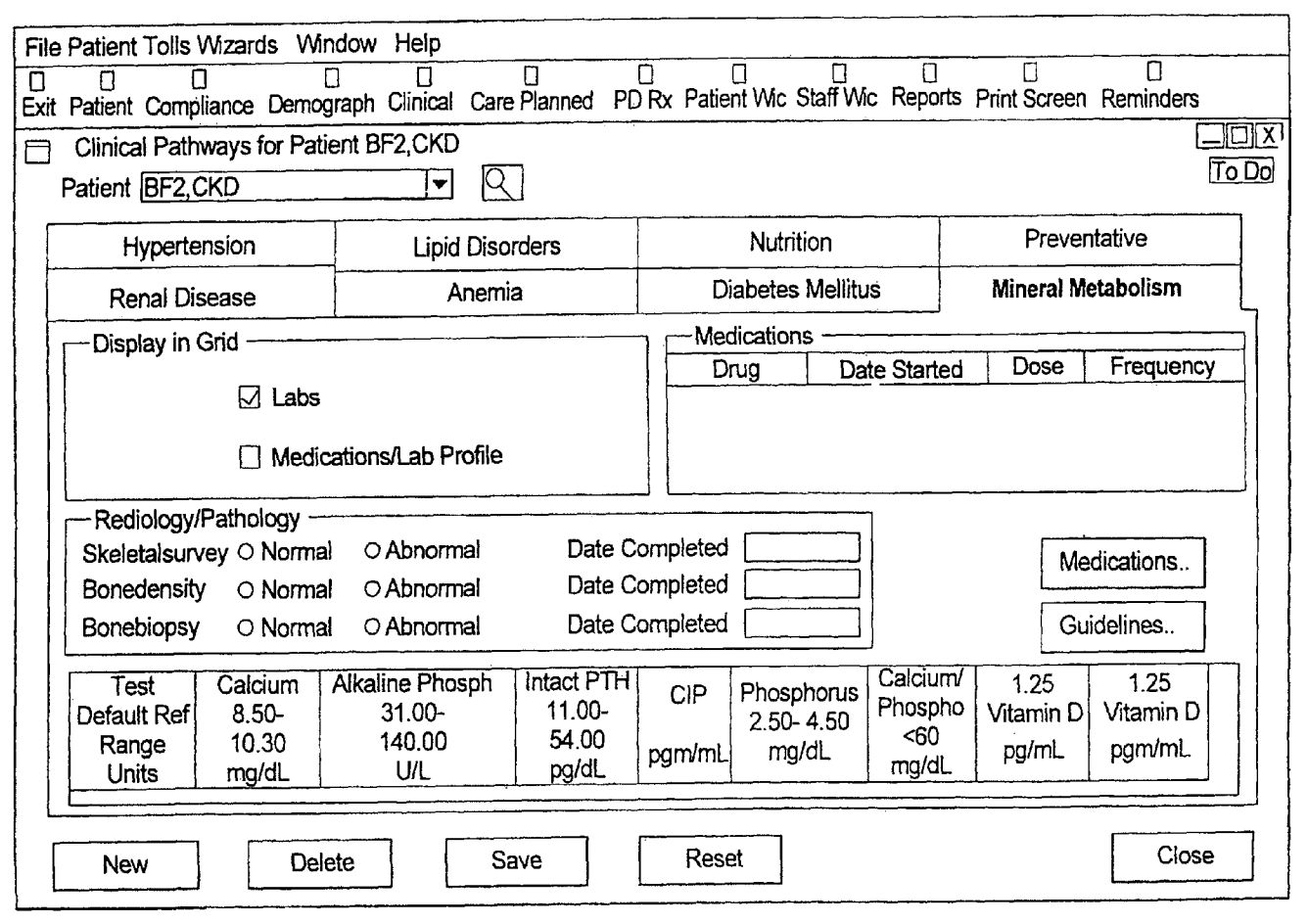

Referring now to FIG. 54, a mineral metabolism pathway is generally illustrated which includes a screen of imported information pertaining to the diagnosis and/or treatment of bone disease in a renal patient. Lab imports include calcium, phosphorus, parathyroid levels which must be maintained to decrease bone disease progression. Medication lists may be viewed in a side-by-side profile to view effectiveness of the treatment. The medication lists may be viewed as well as guidelines and/or sites pertaining to the treatment of bone disease in renal patients.

Figure 55:
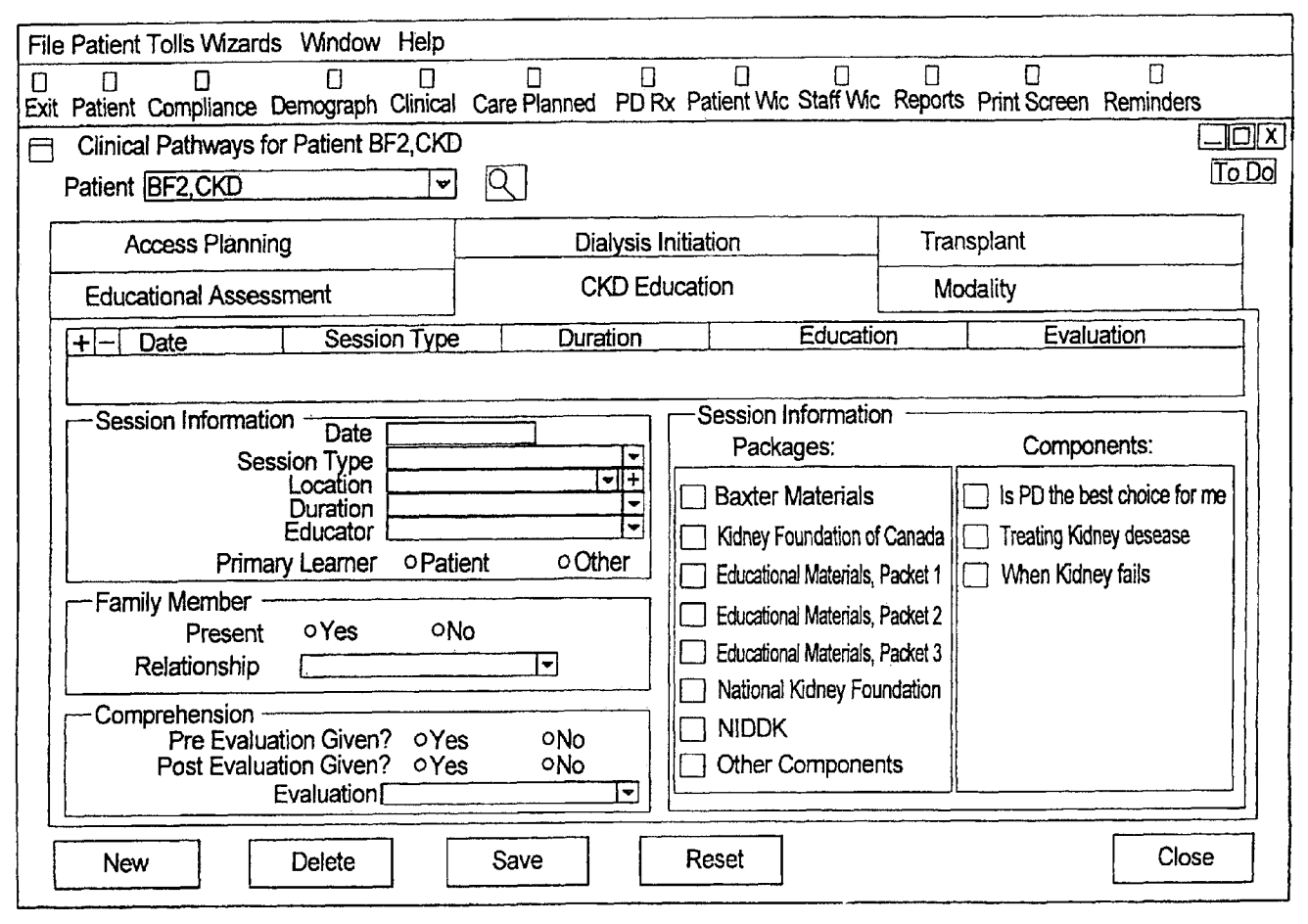

Referring now to FIG. 55, care pathways for education tracking are generally illustrated wherein the doctor or other user or medical professional may track delivery of education by time spent and/or type of session. In addition, parameters relating to the location, participants present, an individual versus group, type of educational materials dispensed, as well as family members and/or partner present may also be input. The screen further provides for tracking of pre-learning and post-learning assessment as a result of the training or education. The navigation link includes a print button that opens a pop-up dialogue allowing a user to select materials for printing. Under the materials discussed, items in each list are selected, a components list may populate with subordinate components and are shown as selected. The user may de-select individual components. Selecting a package removes the subordinate components from the list. Preferably, the grid is sorted in descending date order.

Figure 56:
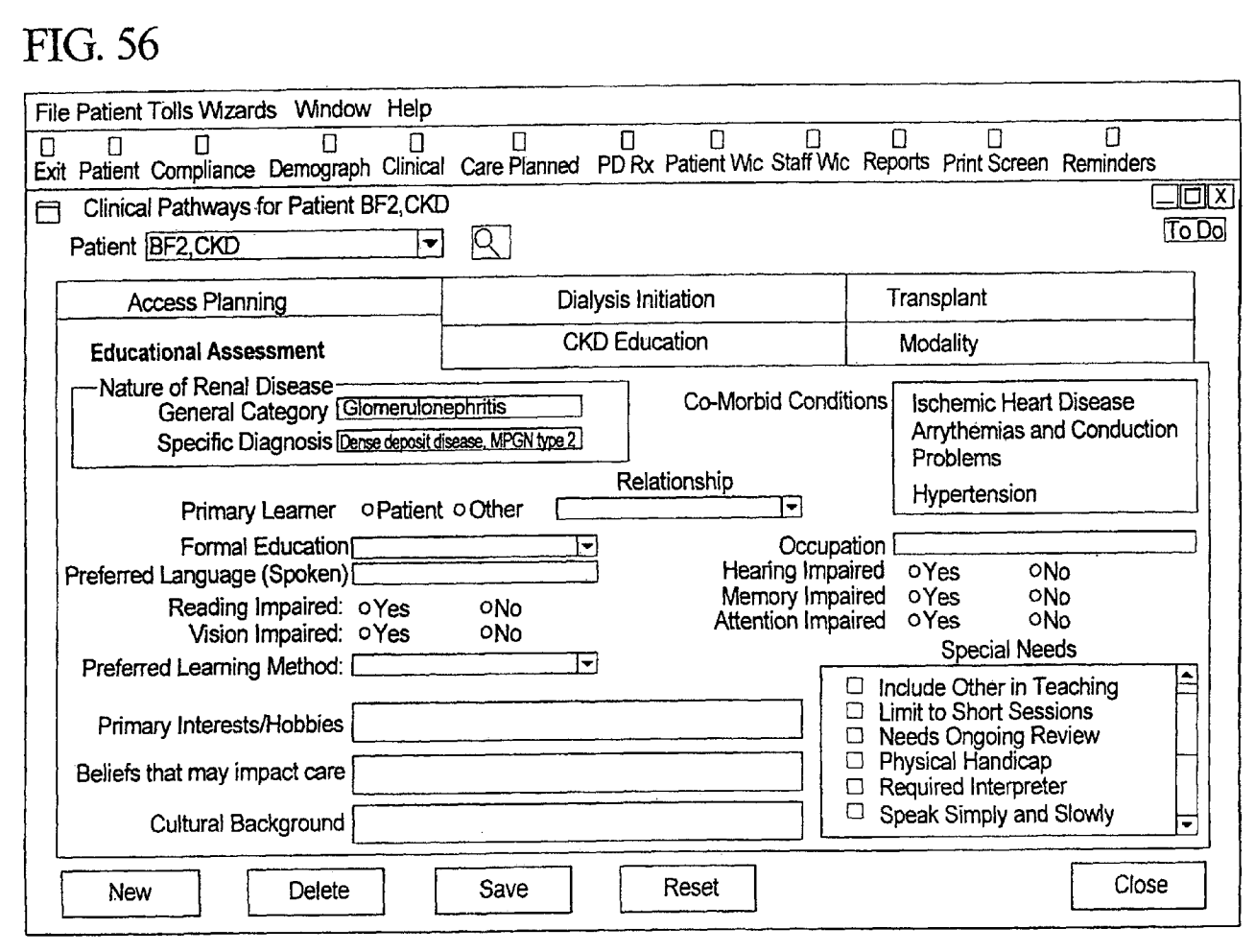

Referring to FIG. 56, a care pathway for educational assessment may be provided that provides information that allows an educator to tailor education towards the grade level of the patient, interests, disease stage, and/or physical deficiencies. The learning methods for the patients may be identified with free text fields within the educational assessment screen that allow the user to identify hobbies, interests and social or religious factors which may impact the education delivery. A number of tabs and/or sub-tabs may be provided in the screen including educational assessment, CKD education, modality planning including eligibility evaluation and modality choice, access planning, dialysis initiation and/or transplant workup. Personnel within a clinic may be restricted to various pathway tabs based on their role within the clinic.

Figure 57A:
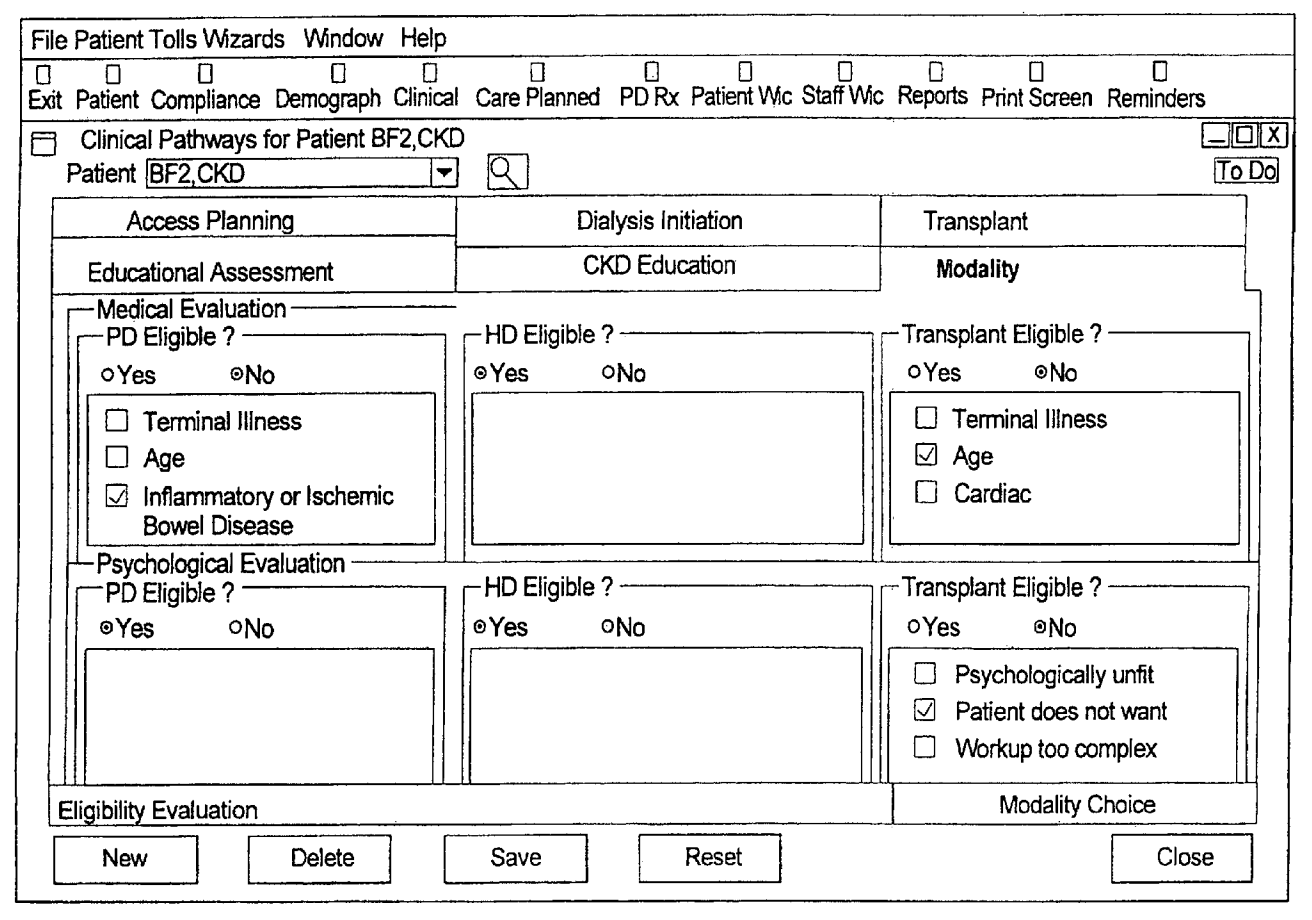
Figure 57B:
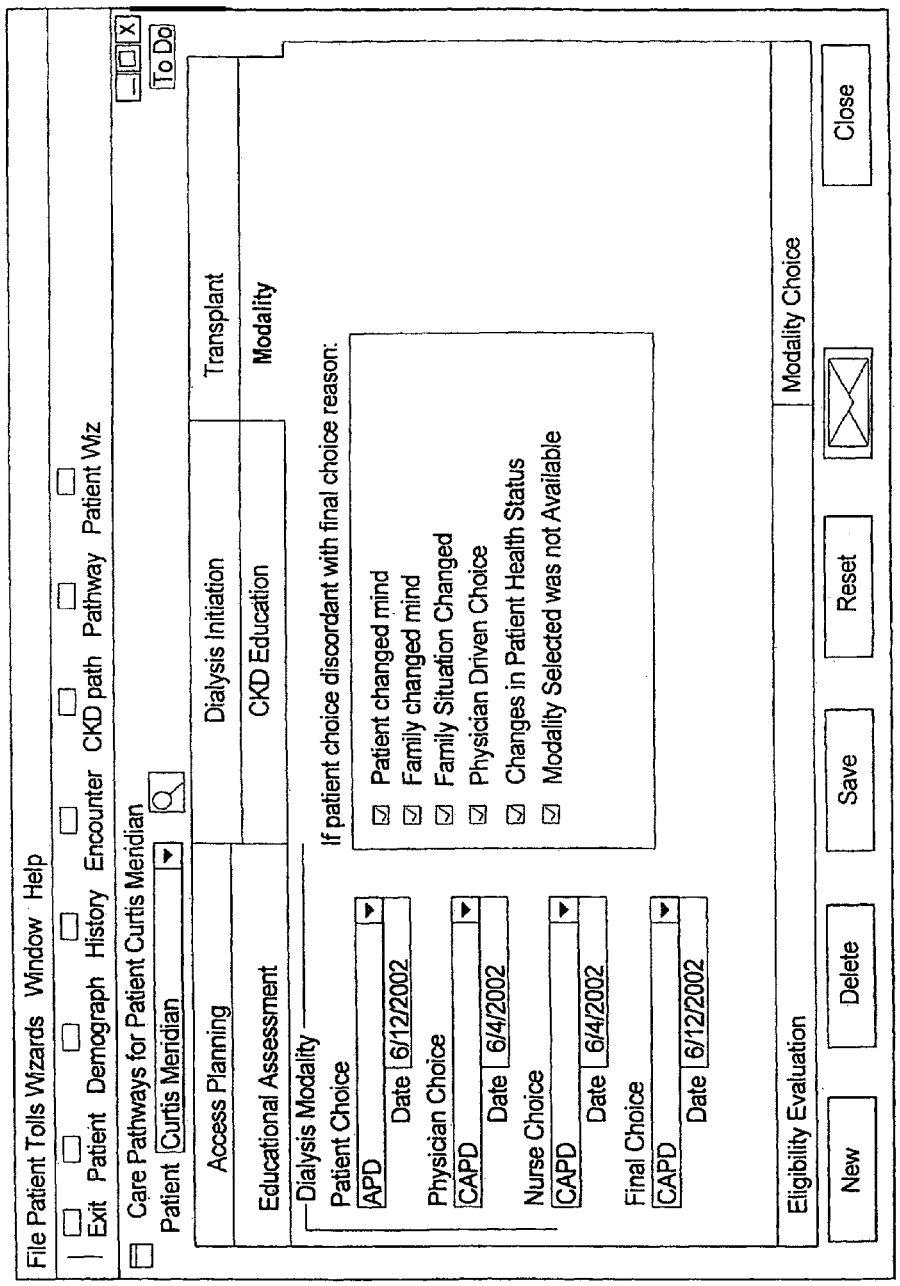

Referring to FIGS. 57(a) and 57(b), a care pathway for modality eligibility and/or planning may be provided via the screen shown in FIGS. 57(a) and 57(b). With respect to FIG. 57(a), the modality eligibility screen allows a clinician or educator to document whether the patient may be eligible for peritoneal dialysis (PD), hemodialysis (HD), or transplantation (T) from a medical and/or psycho-social perspective. Any particular category may be checked "no", and one or more reasons for eligibility may be prompted by the modality eligibility screen. The information allows the user to monitor patients who may be eligible for therapies who may not be receiving them and/or identifying an issue leaving the particular patients ineligible for various therapies. FIG. 57(b) illustrates the modality choice following the eligibility evaluation conducted with respect to FIG. 57(a).

Figure 58A:
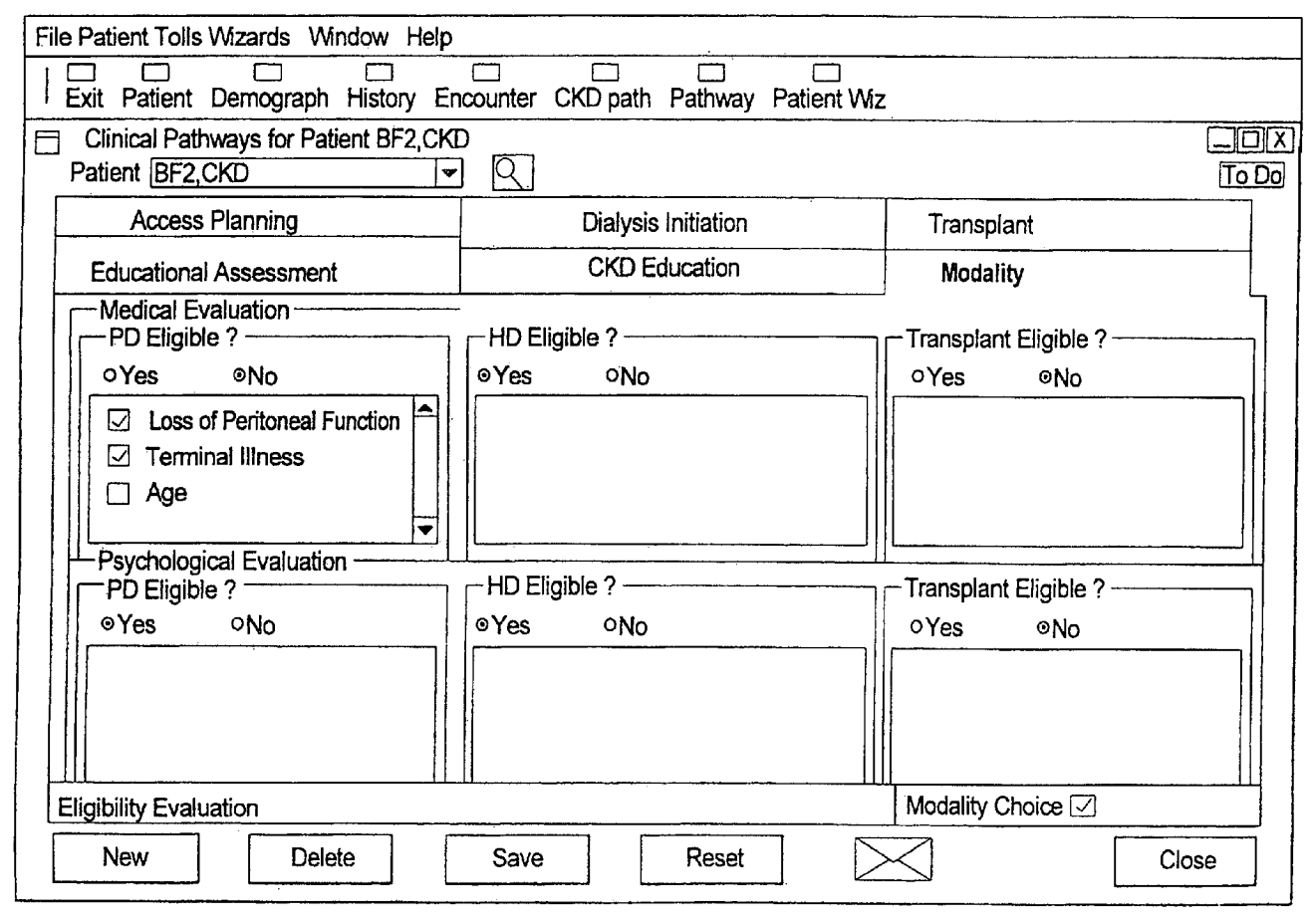

FIGS. 58(a) and 58(b) relate to modality choice including discordant reasons. The screens illustrated in FIGS. 58(a) and 58(b) regard modality choice which indicate the care giver's opinion or opinions for which therapy should be chosen for the patient based on eligibility criteria or patient discussion. A patient, a nurse, a doctor, or other health care professional has made a choice, and the choice is noted. If the patient and health care choice is discrepant, the reason may be noted. Information may then reveal that the patient or medical professional has a bias or differing choice than the reason, or its occurrence may require determination.

Figure 59:
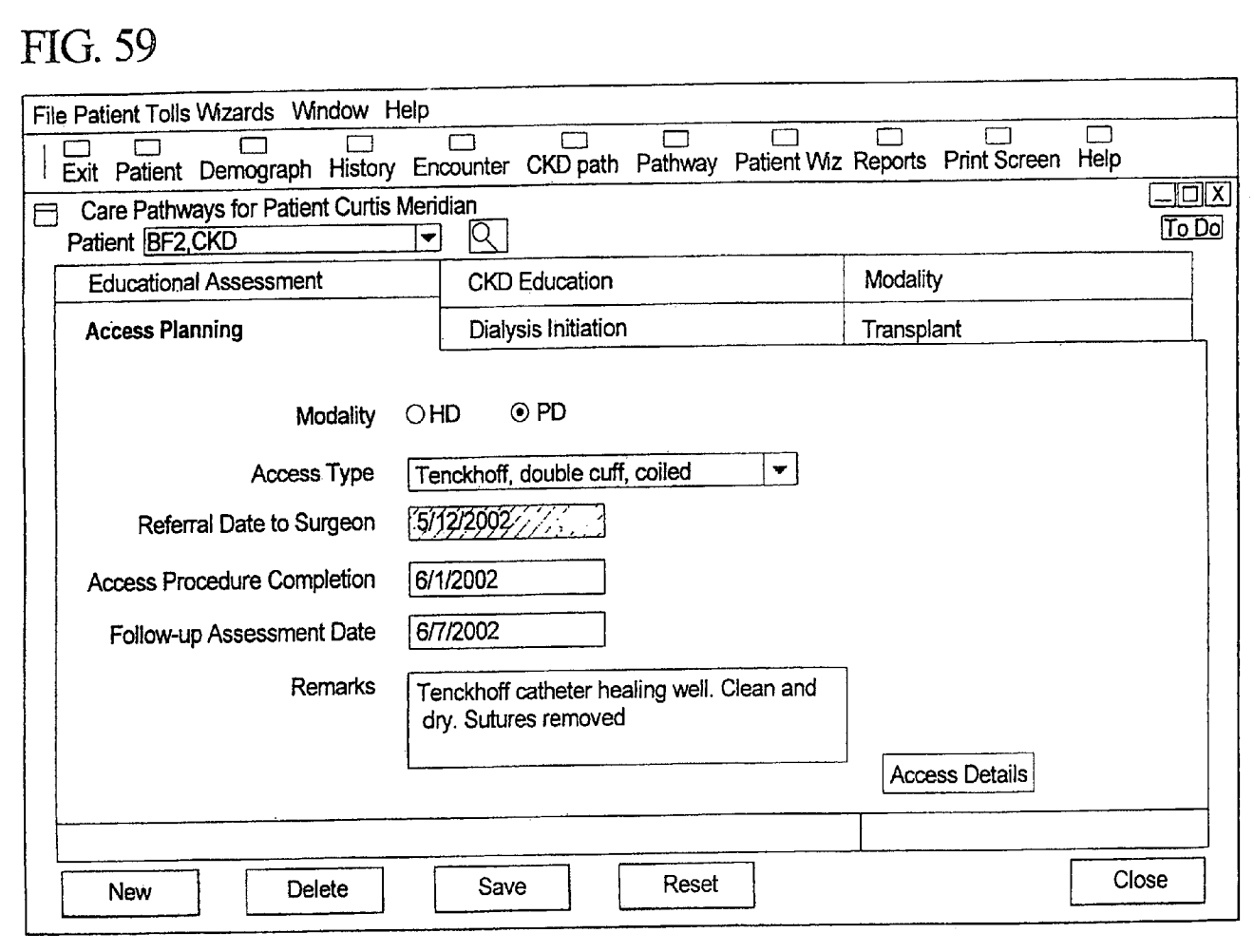

Referring to FIG. 59, an access planning screen may be provided to note the type of dialysis access chosen to be placed. A reference date to the surgeon, when the access is placed, and a follow-up appointment made, may be information provided on the screen. The access planning screen encourages monitoring of the patient for access placement and follows access placement. The text field notes results of patient placement following surgical access placement.

Figure 60A:
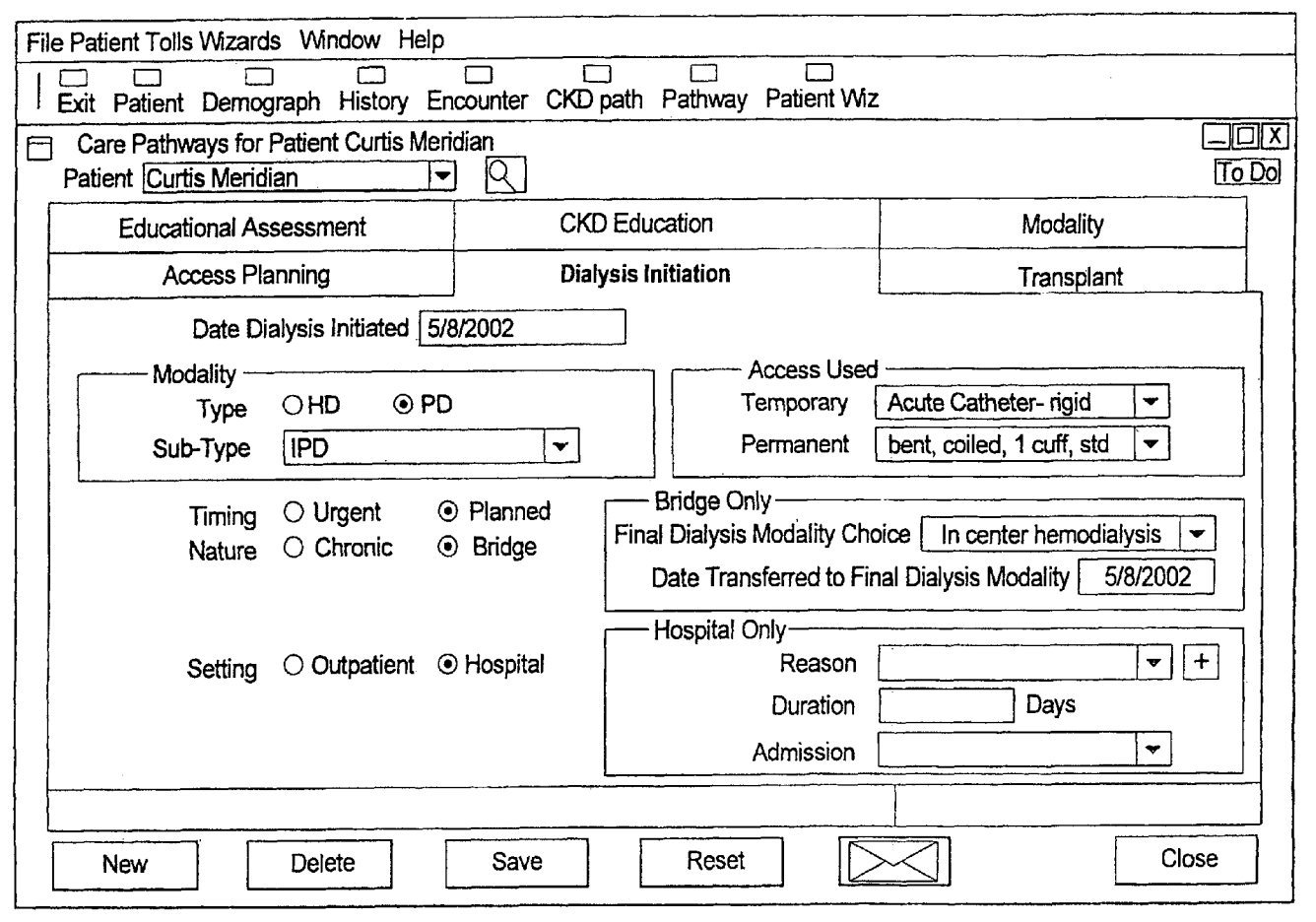

Referring now to FIGS. 60(a) and 60(b), dialysis initiation screens may be provided to track the type of dialysis access being placed and/or whether the access is a permanent type or temporary type. Preferably, access is placed soon enough to heal (permanent access) and tracking of where the access is placed (inpatient versus outpatient) and a place within the hospital where the patient was admitted. FIG. 60(a) relates to modality initiation within the care pathway, and FIG. 60(b) relates to transplant workup. Within the modality initiation, the sub-type depends on the modality type selected. Temporary and permanent access lists under the access used section depends on modality type. Further, a bridge-only panel is disabled if chronic is selected; and the hospital only panel is disabled if outpatient is selected. The final dialysis modality choice may be pre-populated based on the final choice made on the modality planning form. The user may be prompted if they attempt to change tabs without saving changes. Referring to FIG. 60(b), a transplant workup may be identified as complete after a submitted referral has been checked and the date entered. On cadaver wait list may be entered or LRD workup may be checked and date entered; or all initial workup fields checked and dates entered.

Referring now to FIGS. 61(a)-61(f), charts are illustrated defining various care pathway assignments based on various laboratory results. Laboratory results may then be fed into the pathway as identified in the charts shown in FIGS. 61(a)-61(f) automatically.

FIG. 62 illustrates a clinical pathway relating to preventative measures, for example, vaccinations and screenings. A date may be entered relating to each vaccination received, and screening dates may be entered for the next scheduled or necessary date to obtain a particular screening.

Figure 63:
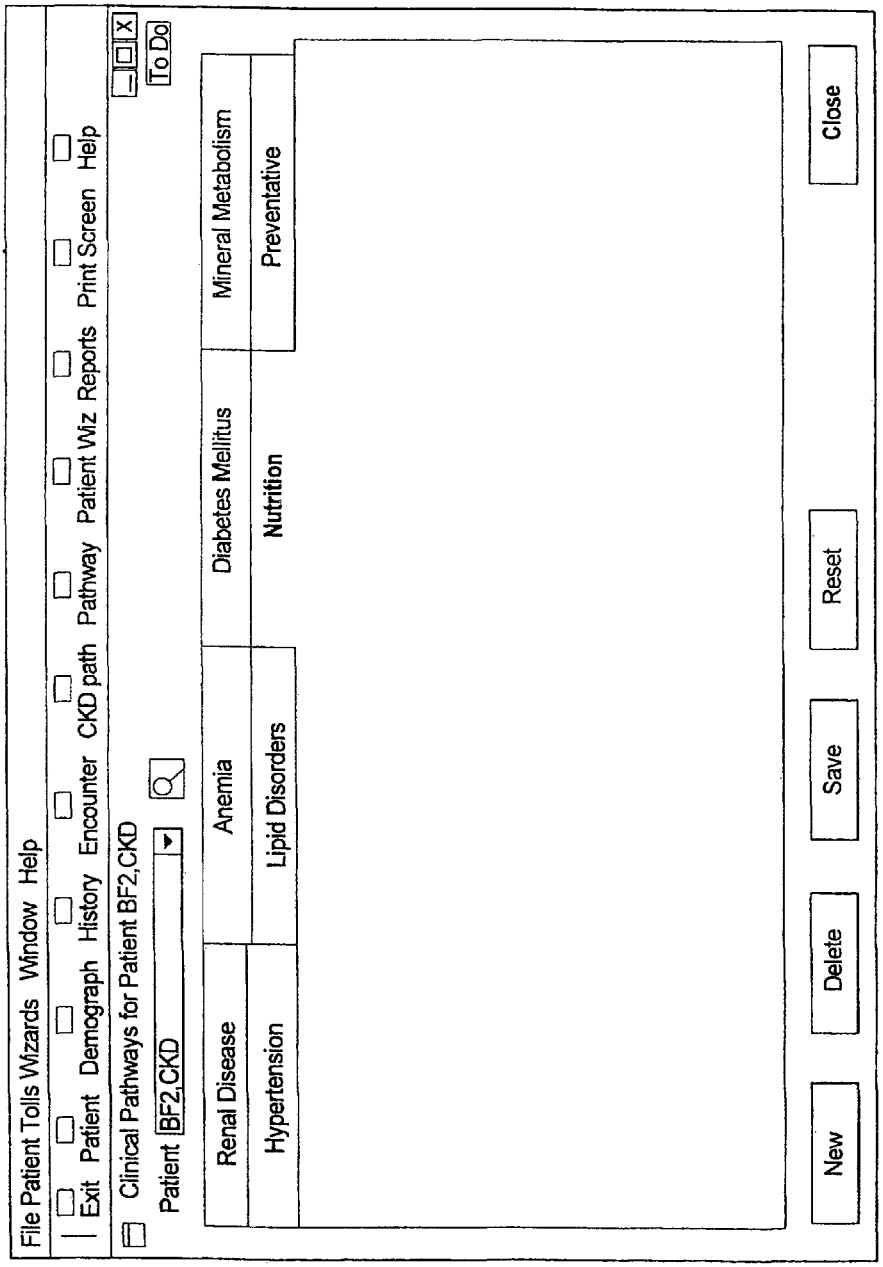
FIG. 63 illustrates a nutrition pathway screen in an embodiment of the present invention.

A nutrition pathway is illustrated in FIG. 63 which may include information based on past, current or future nutritional requirements.

Figure 64:
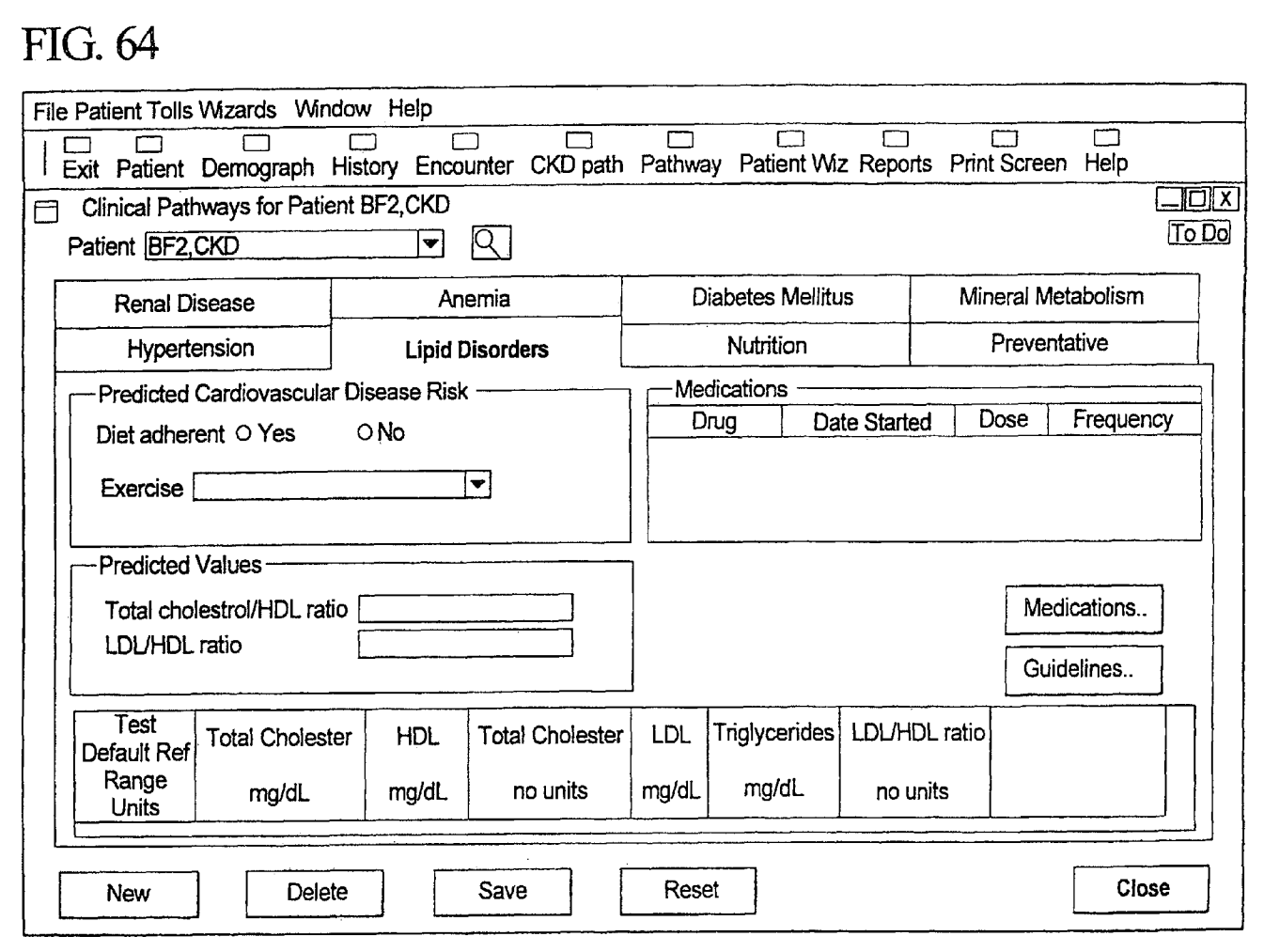

FIG. 64 illustrates a clinical pathway screen for lipid disorders including values for total cholesterol, HDL, LDL, triglycerides and/or LDL/HDL ratio. Imported information may be provided from the medications as previously discussed.

Figure 65:
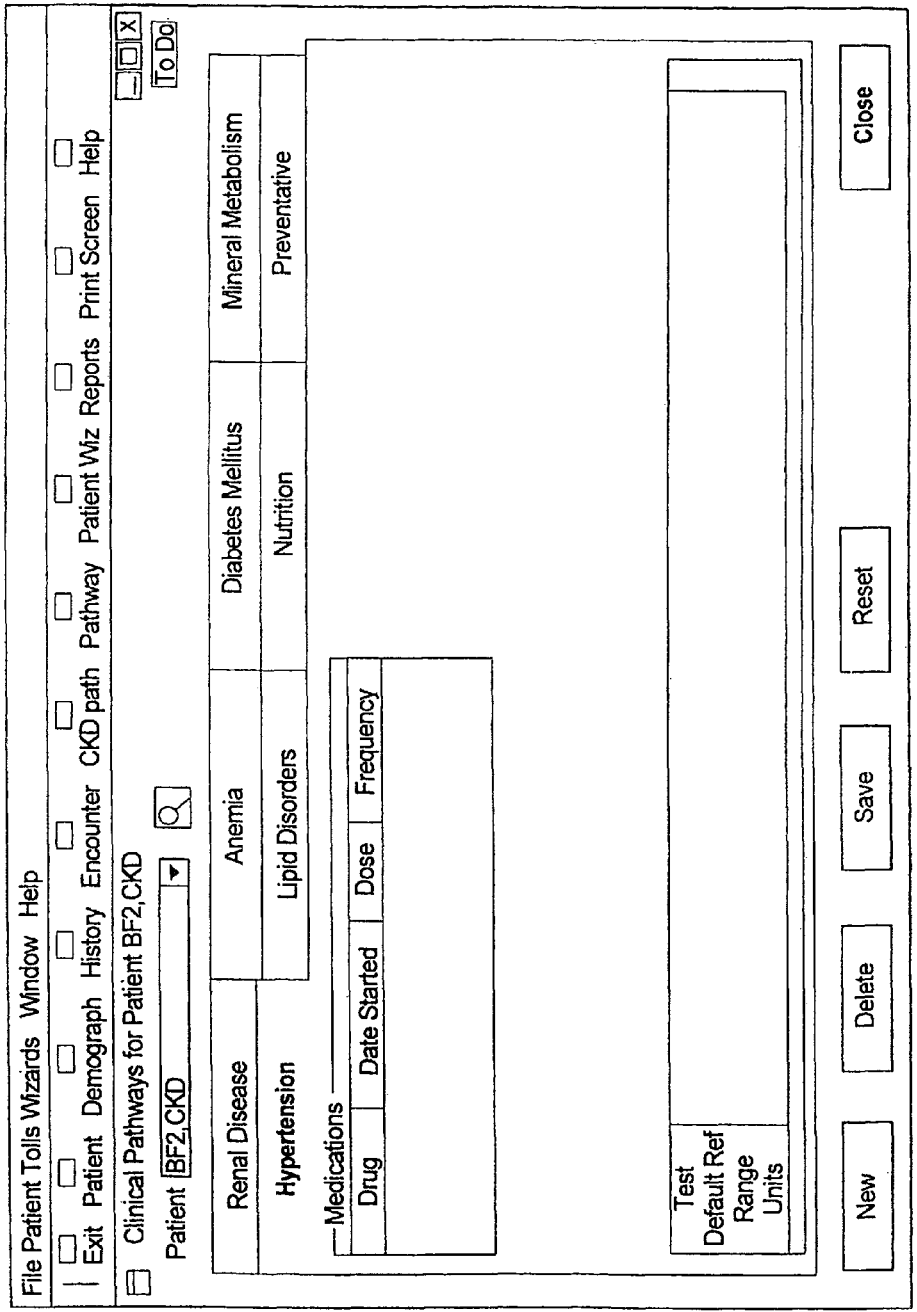
FIG. 65 illustrates a hypertension pathway screen in an embodiment of the present invention.

Referring to FIG. 65, a hypertension pathway may be provided which includes text information with respect to any condition related to hypertension as well as any imported or other information regarding medications.

Figure 66:
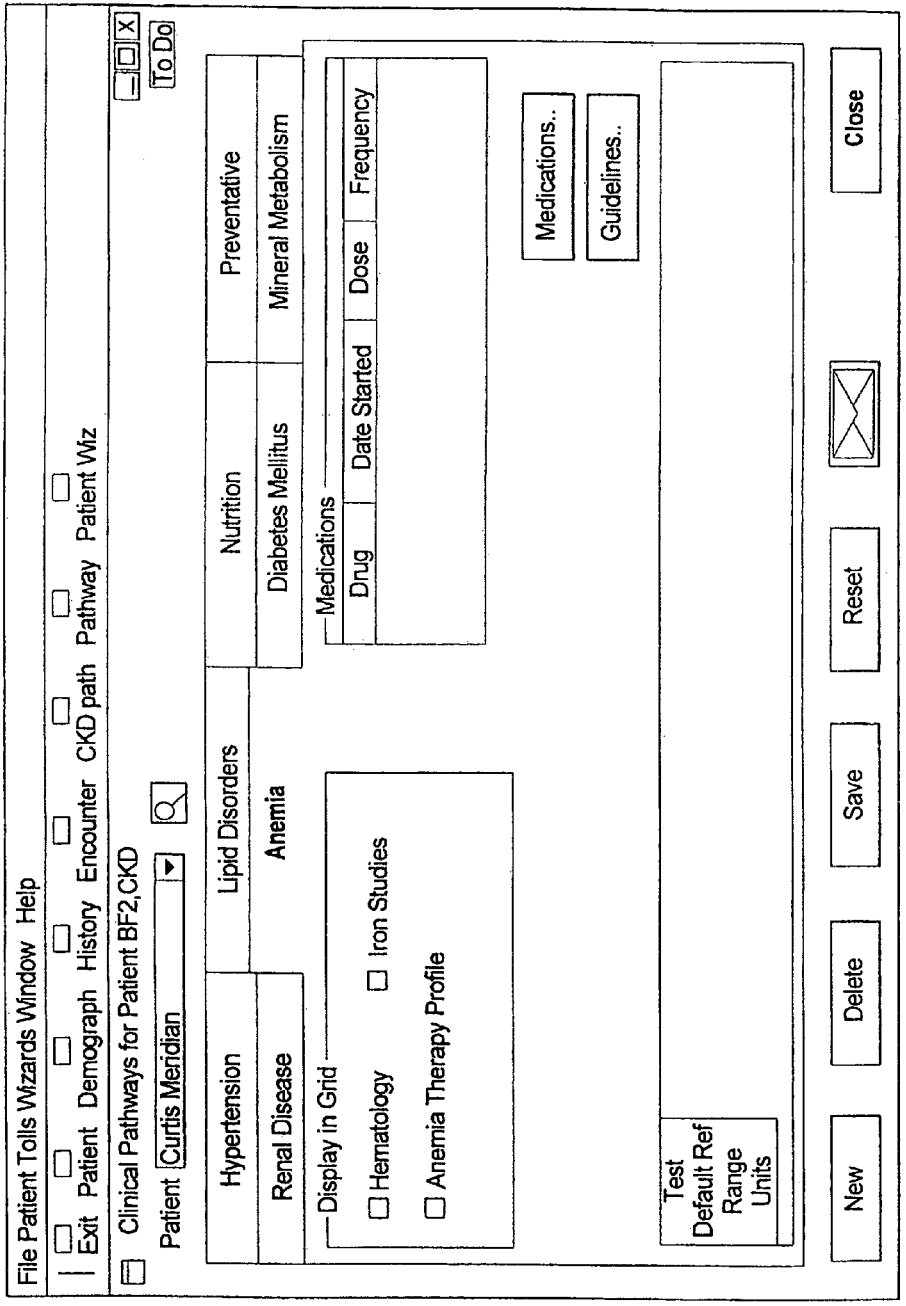
FIG. 66 illustrates an anemia pathway screen in an embodiment of the present invention.

Referring now to FIG. 66, the anemia pathway is imported information from other areas of the software which may be pertinent to the diagnosis and/or treatment of anemia. Information may include lab values such as hematology and iron studies and medications used in the treatment of anemia in renal disease patients. Prescription of medications may be identified by clicking on medications. The guidelines pertinent to the treatment of anemia may also be seen as an appropriate website by clicking "guidelines." The format of the screen encourages medical professionals to view all aspects of anemia that impact treatment and/or effectiveness of the treatment, such as low iron levels that may decrease effectiveness of erythroeocitic medication. Otherwise, the doctor may review whether blood levels are low while the erythroeocities which may be due to low iron. Various calculated fields may be provided, such as, for example, transferrin saturation, calculated transferrin and calculated TIBC. All units may be converted and preferably conventionally input as required to perform the calculations.

FIGS. 67-83 illustrate a renal peritoneal dialysis (PD) and hemodialysis (HD) access management system. The PD and HD access management system is a comprehensive tool to track PD and HD access information. As used hereinafter, "access" may refer to access placement, infections and non-infection related problems associated with PD and/or HD, medications associated with PD and/or HD, and hospitalizations associated with PD and/or HD.

Figure 67:
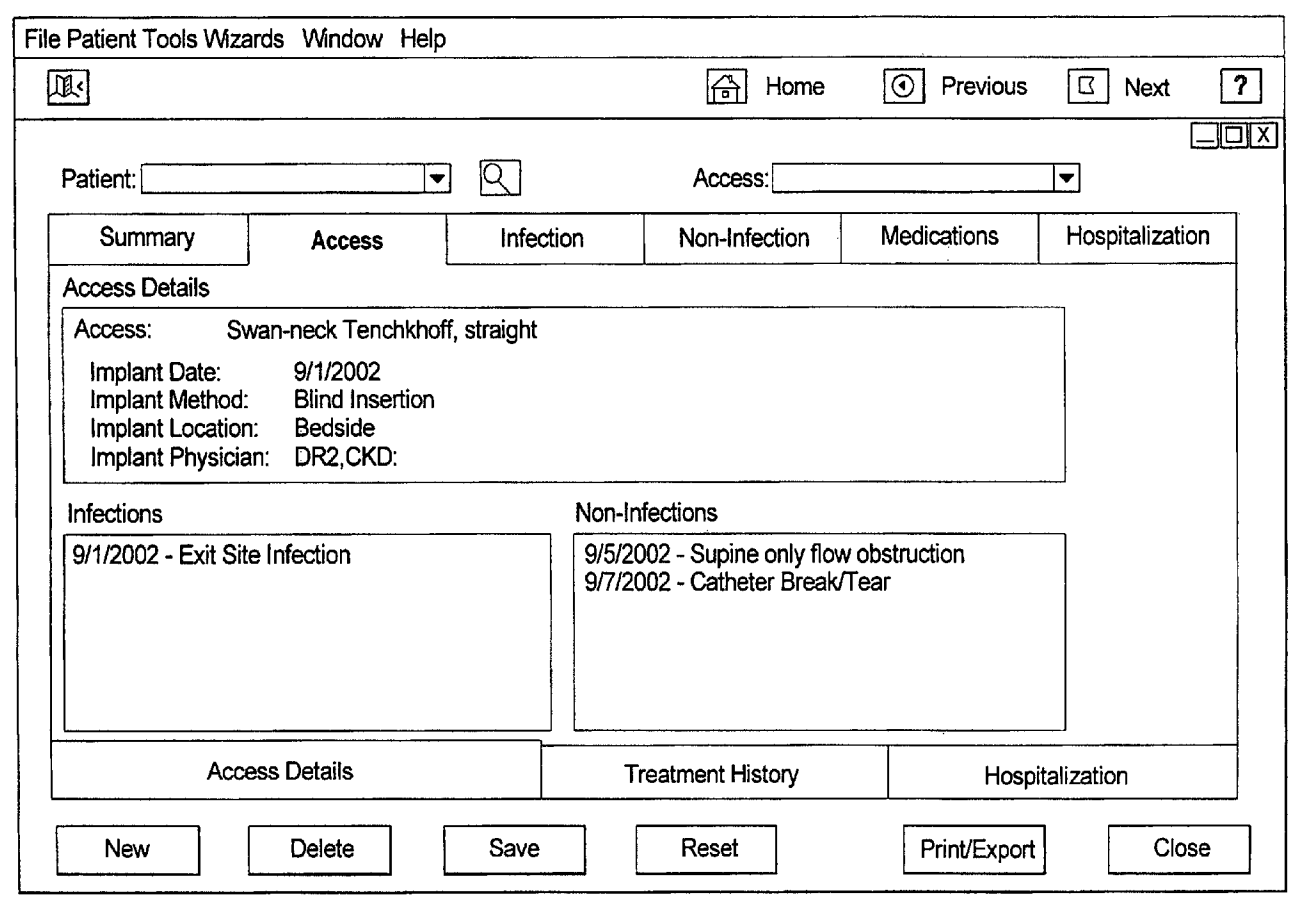

Referring now to FIG. 67, an access summary report screen is generally illustrated. The access summary report screen may be displayed on a computer to be viewed by a patient, a physician and/or a user. An access report may be provided on the access summary report screen and may provide an overview of the patient care relating to access treatment. A summary report may be provided on the access summary report screen beneath the access report and may display data about the access of a patient. The report summary may contain relevant data, such as, for example, implant date, surgeon and/or treatment facility. The information may be presented in a reverse chronological order to compare infection problems and non-infection problems in a manner to simplify comparison of the infection problems and the non-infection problems.

Figure 68:
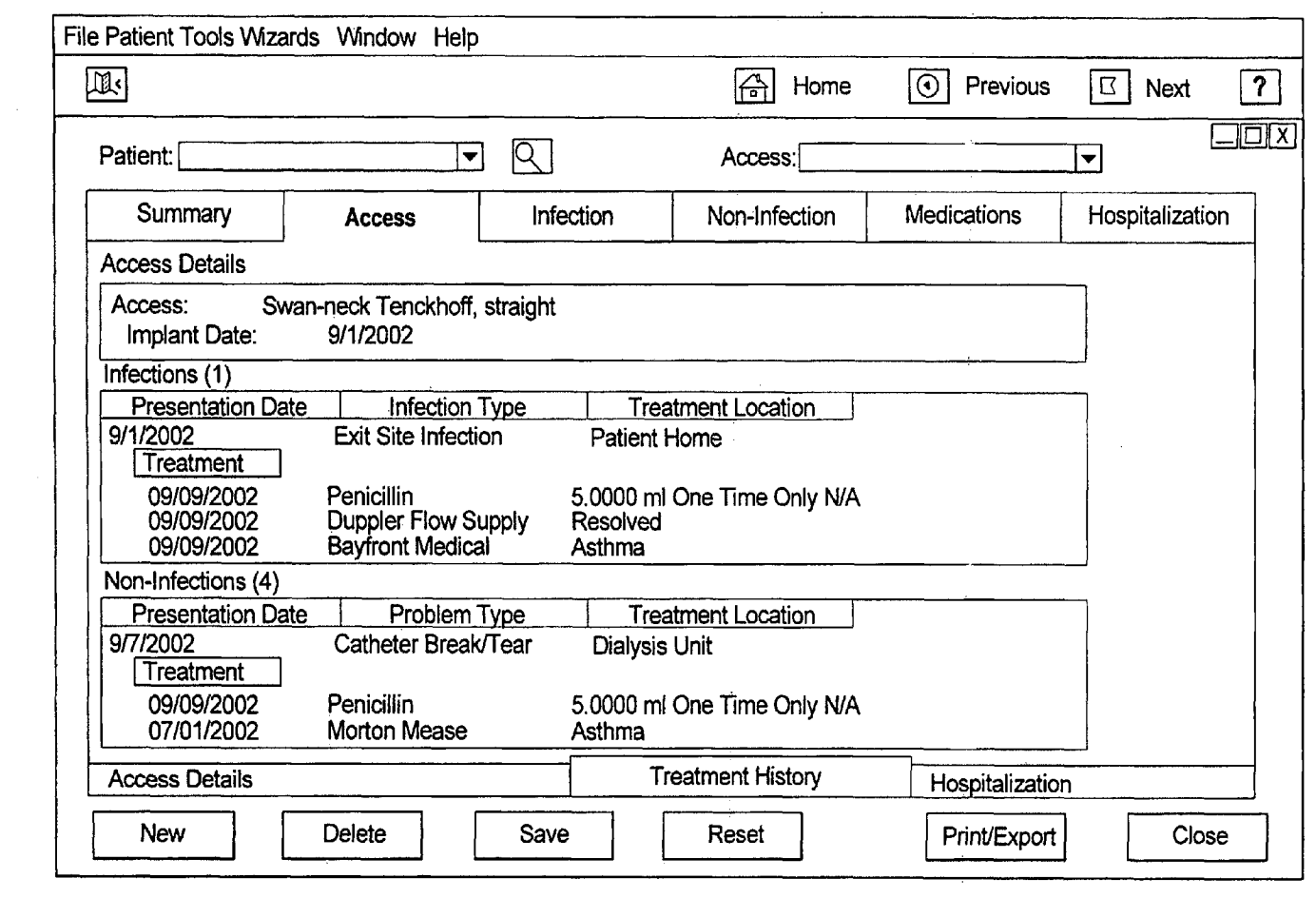

Referring now to FIG. 68, a treatment history screen is generally illustrated. A treatment history report may be provided on the treatment history screen and may provide a collection of information from a history of a patient. The treatment history report may include, for example, a collection of medications, hospitalizations and/or interventions performed for any problems associated with the access. The treatment history report may provide a description of the access followed by a section for infection problems and a section for the non-infection problems. Data for the infection problems and non-infection problems may be displayed, including the dates, treatment and/or treatment locations associated with the treatment of the patient. Medications assigned for either an infection problem or a non-infection problem may be displayed on the screen including, for example, duration, dosage, route and/or frequency of the medication.

Further, the treatment history report may display hospitalization information associated with the infection problems and/or the non-infection problems. The hospitalization information may include an admit date and/or a discharge date as well as a final diagnosis for the patient. Interventions, treatments and/or outcomes of the interventions for the patient receiving treatment may also be illustrated on the treatment history screen. The interventions, treatments and/or outcomes of the interventions may be displayed in reverse chronological order to display a time line of treatments associated with the access of the patient and/or a complication with the access.

FIG. 69 illustrates a hospitalization summary report screen as displayed on a computer. The hospitalization summary report screen may contain and/or may display a description and/or information related to hospital admissions associated with an access and/or a problem associated with the access. The hospitalization summary report screen may display hospitalization data displayed and may have sections displaying infection problems and/or non-infection problems that may require hospitalization.

Referring now to FIGS. 70-78, an access tab screen may be displayed on a computer containing data pertaining to the access of the patient. The access tab screen may be divided into three subtabs including implant details, clinical assessment and/or dynamic assessment. The access tab screen may be provided to track and/or to manage the history of treatment for the patient. The access tab display screen may display access implantation and/or removal/abandonment for the patient.

Figure 70:
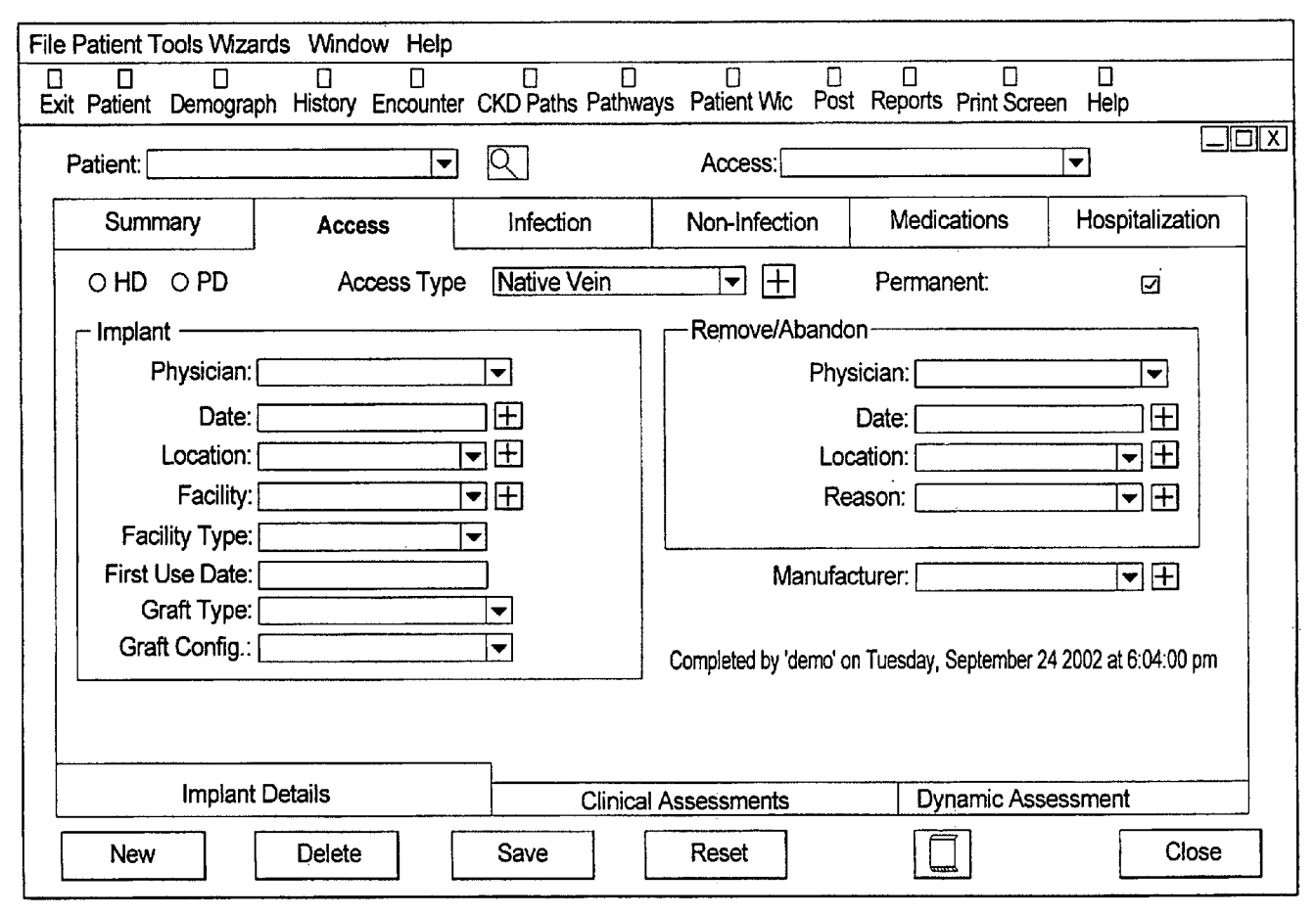

FIG. 70 illustrates an implant detail screen. The implant detail screen may contain data relating to access implantation for the patient. Implantation data, such as, for example, implantation date, physician and/or implantation facility type may be collected for a single access and/or for a plurality of accesses of the patient. PD specific data such as, for example, break in method (for inserting an access) and/or first full prescription date may be collected and/or displayed on the implant detail screen. HD specific data, such as, for example, access location and/or first use date, may be collected based on the modality of the access. The implant detail screen may display subsequent access removal and/or abandonment data of the patient.

Figure 71:
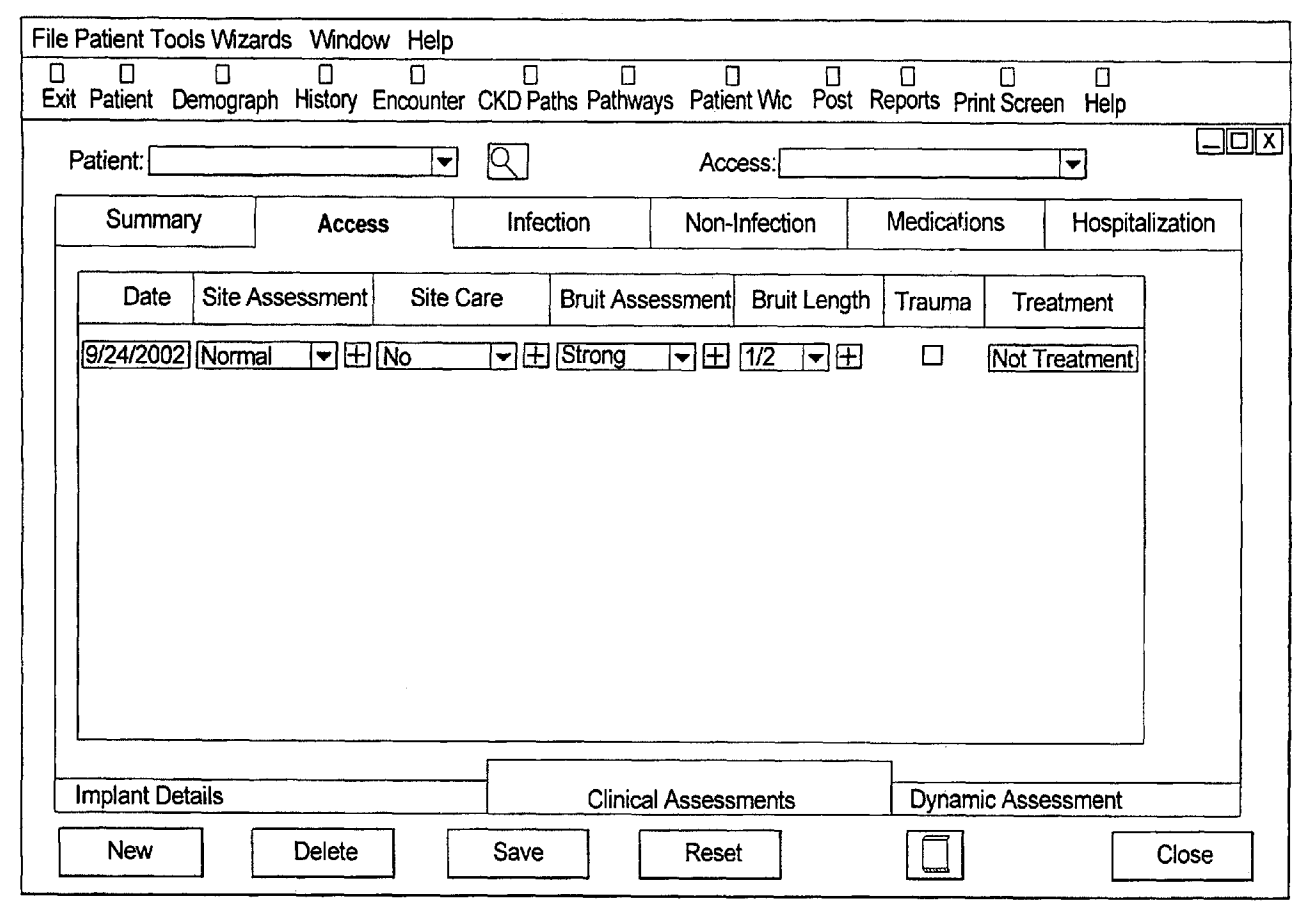
Figure 72:
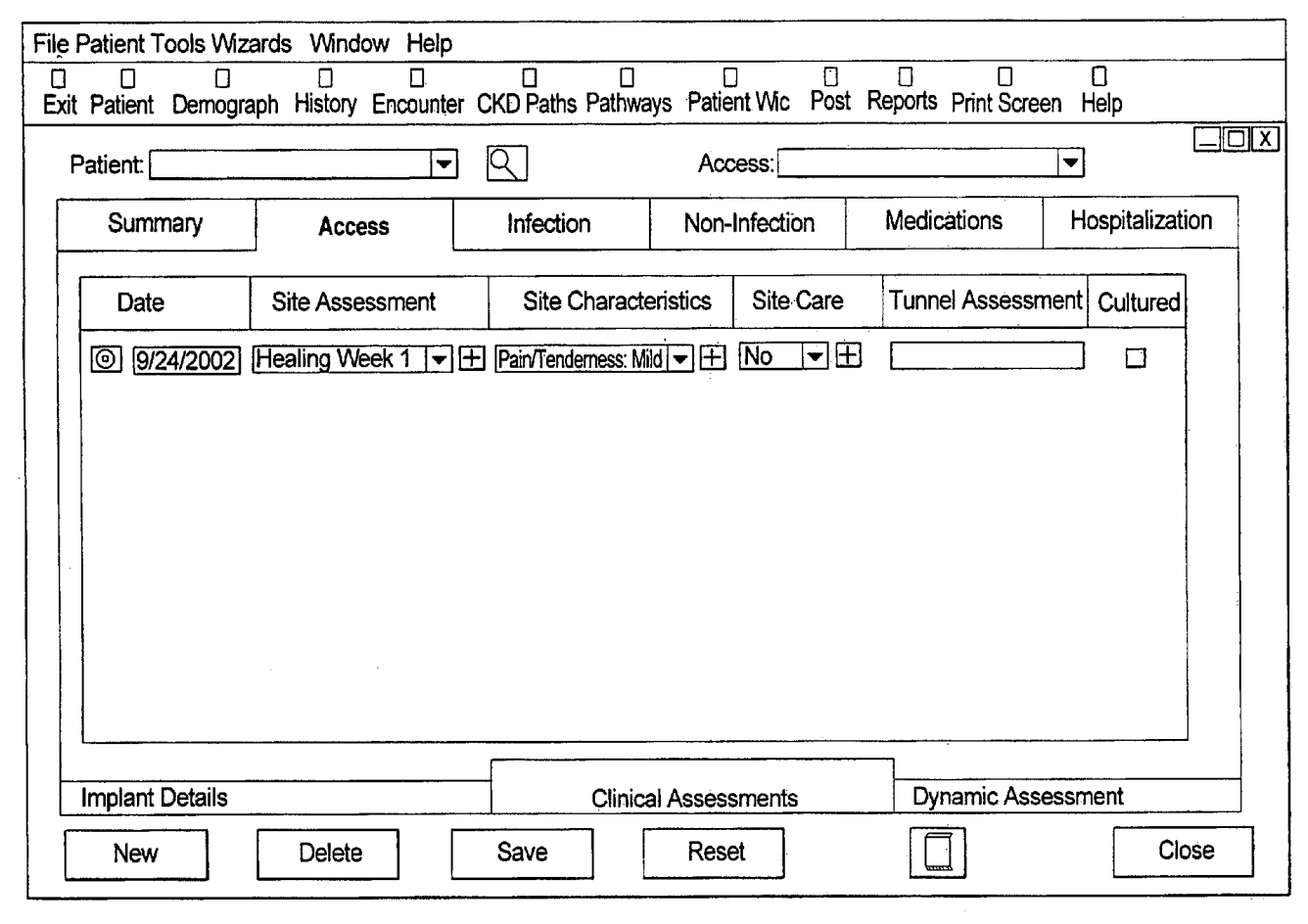

FIG. 71 illustrates a clinical assessment screen displayed on a computer which may provide information on care of the patient. Subsequent to implant data entered into the system, clinical assessments for the implant data may be entered for an access of the patient. Data collected as part of the clinical assessment may vary depending on the type of access/patient modality. Clinical assessments may be displayed in reverse chronological order so the most recent assessment may be visible when the access tab is selected. The assessment screen for a patient undergoing HD, for example, may collect data on the time of assessment of the patient including pre-treatment, post-treatment or no treatment data. Additionally, a physician and/or user may enter clinical assessment data directly into the clinical assessment screen. FIG. 72 further illustrates a clinical assessment screen that may contain a PD assessment area. The screen may illustrate, for example, that a culture was taken as part of the clinical assessment process.

Figure 73:
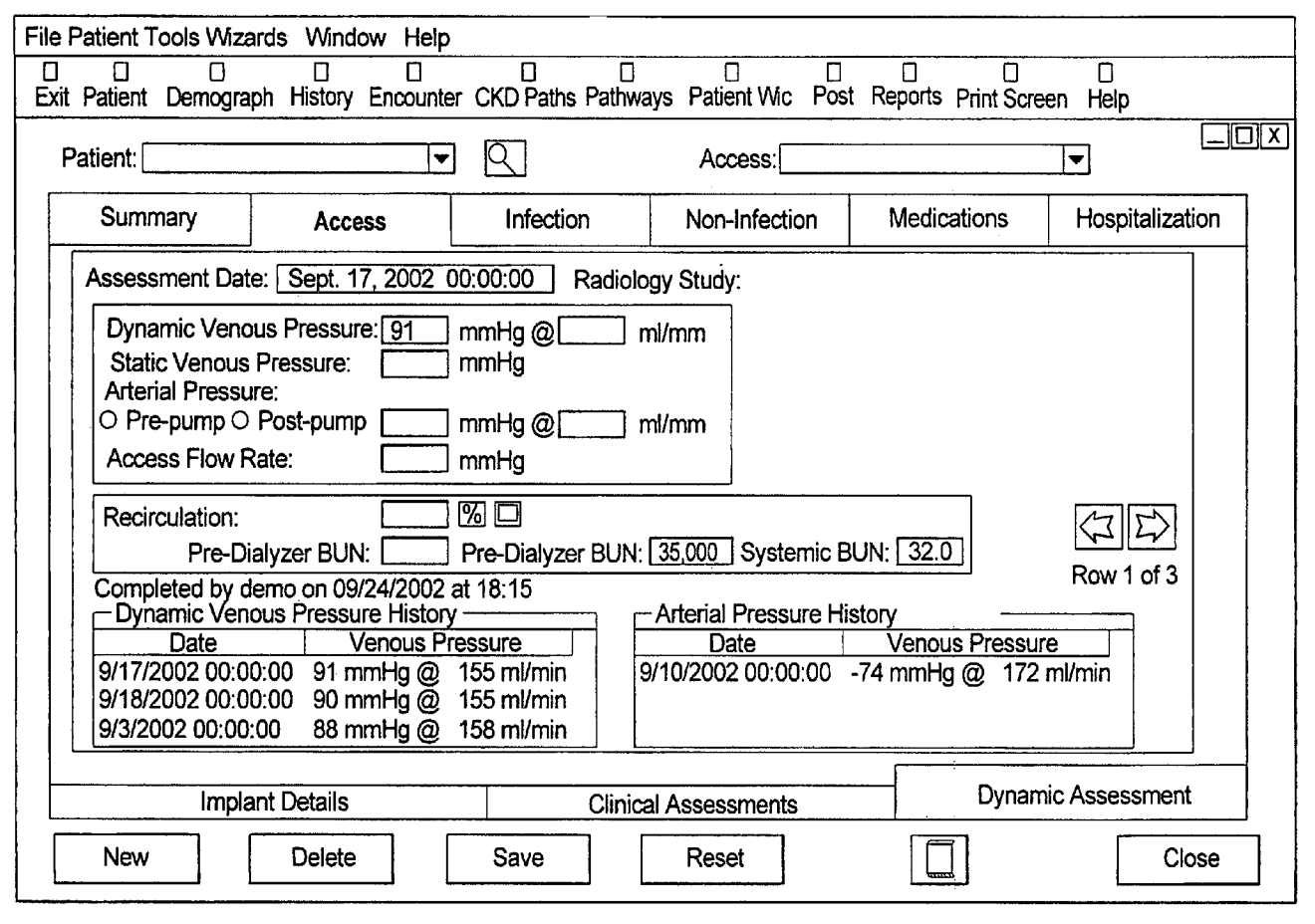

Referring now to FIG. 73, a dynamic assessment screen is illustrated. The dynamic assessment tab may contain collected data on an outside assessment performed with regard to the patient. Measurements for dynamic venous pressure and/or arterial pressure may be displayed on the dynamic assessment screen to assist the user with measuring the tendencies of the data. A user may enter pre-pump and post-pump arterial pressure. The screen may allow a user to calculate the re-circulation percentage for the patient based on BUN values and/or a user may enter a re-circulation percentage directly into the field or may enter all required BUN values. Blood urea nitrogen (BUN) is a measure of the amount of urea nitrogen, a waste product of protein metabolism, in the blood. Urea is formed by the liver and carried by the blood to the kidneys for excretion. Because urea may be cleared from the bloodstream by the kidneys, a test for measuring an amount of urea nitrogen that remains in the blood may be used as a test of renal function. If the required BUN values are entered, a calculator associated with the dynamic assessment screen may display a re-circulation percentage for the input values. The formula for calculating re-circulation may be: 1 100 [BUN (systemic)-BUN (pre)] [BUN (systemic)-BUN (post)]

If the re-circulation percentage is entered manually, changes to the BUN values may not be re-calculated. The re-circulation percentage may be saved to a database.

Figure 74:
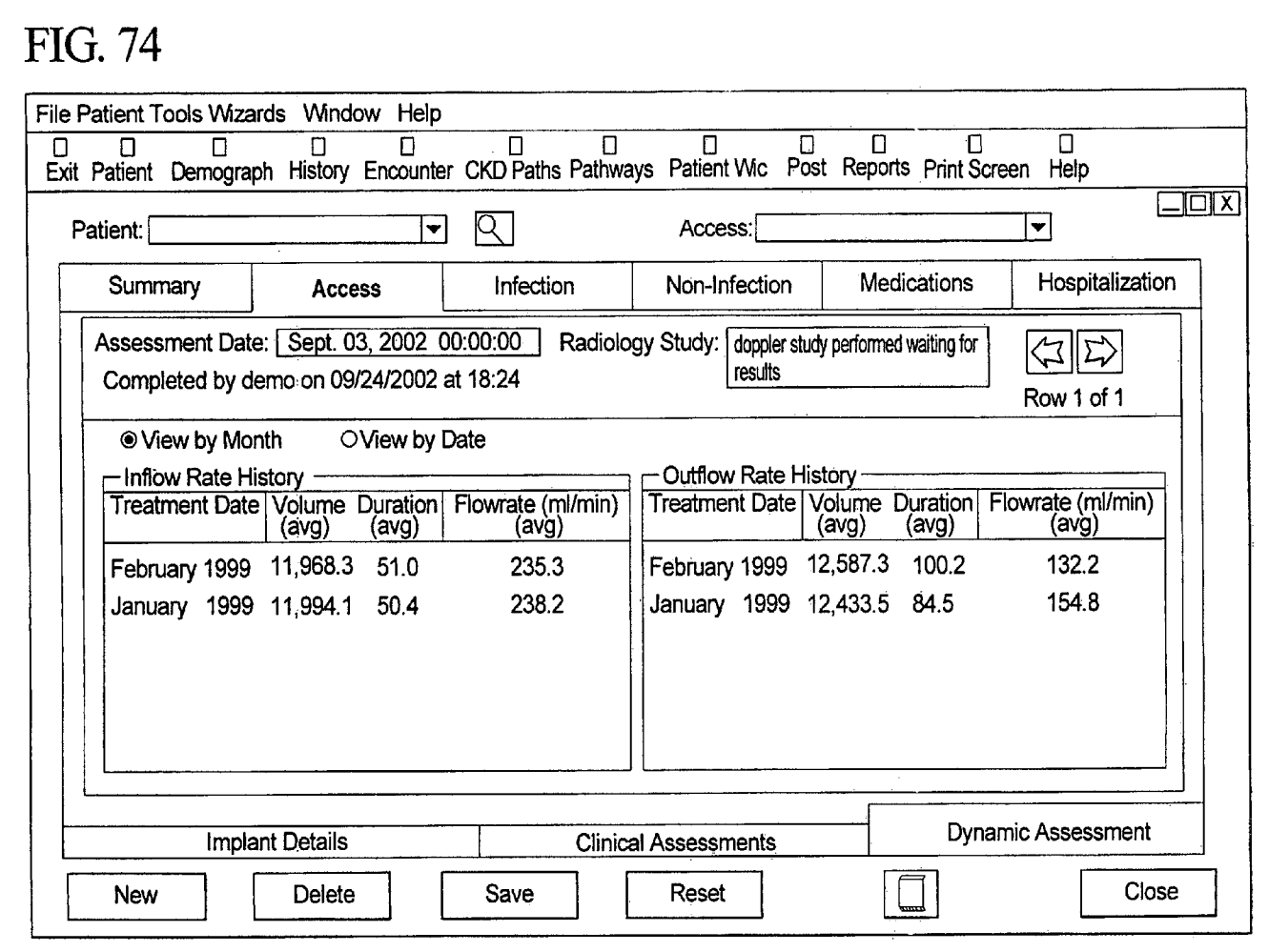

Referring now to FIG. 74, a secondary dynamic assessments screen is illustrated. The secondary tab may display collected data on radiology studies with regard to the access of the patient. The tab may also display BUN flow rates for APD patients that may be collected by a home BUN detection device. Flow rates may be viewed periodically, such as monthly, or by a specific date. The tab may also display flow rates including inflow and drain information.

Figure 75:
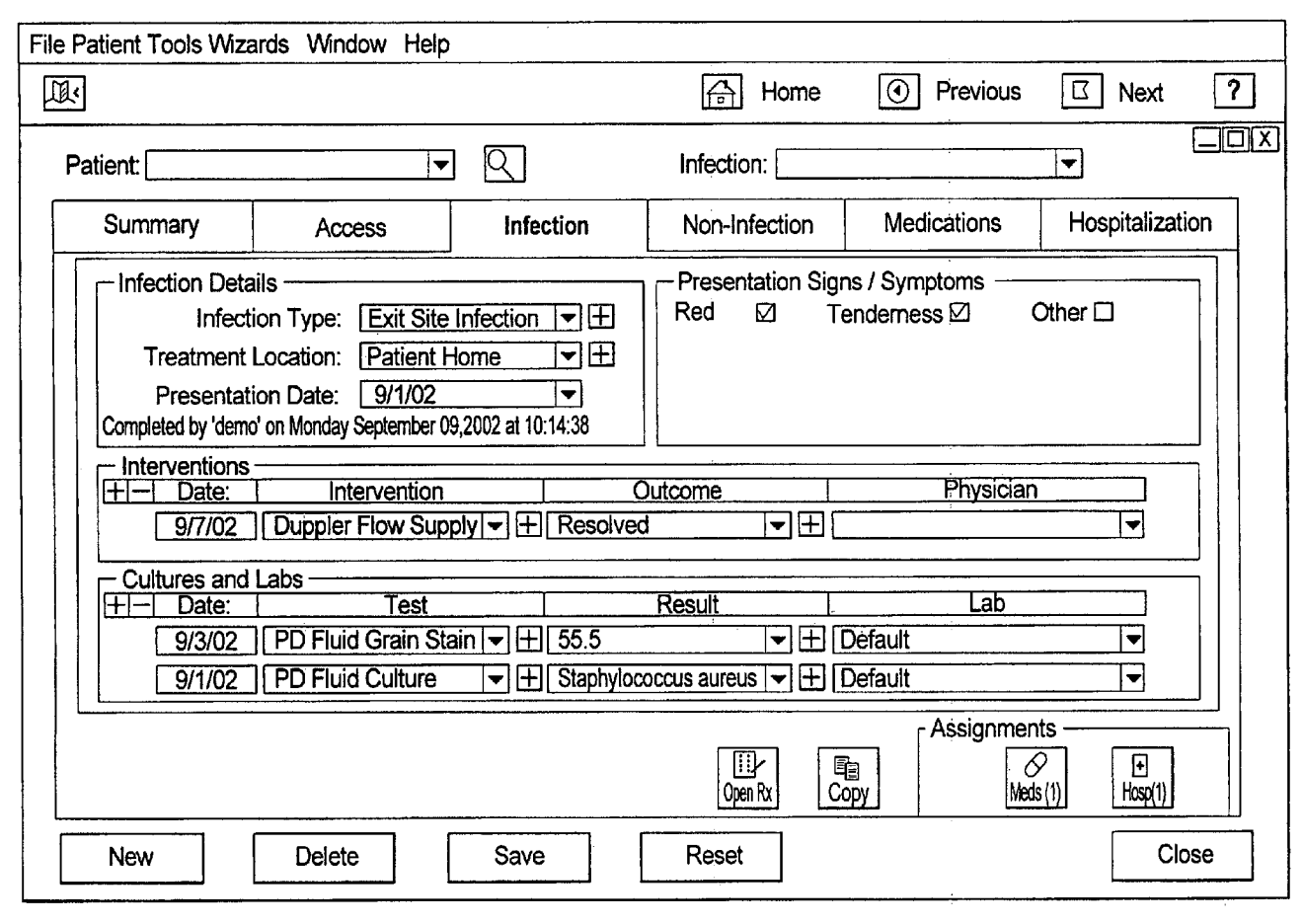

Referring now to FIG. 75, an infection tab screen as displayed on a computer is illustrated. The infection tab screen may provide infection information for an access of the patient. The screen may display collected data on an infection associated with the access of the patient. Infection data may be displayed in reverse chronological order, and the most recent infection may be viewed first. The infection tab screen may display infection information based on, for example, whether the access is for a PD patient and/or an HD patient. Access infection culture and/or laboratory data may also be entered by a physician and/or a user on the infection tab screen. Further, the infection tab screen may display the active treatment for the patient undergoing PD or HD. The medication screen may be opened from the infection tab by a user by clicking on an Open PD Rx button on the infection tab screen. After the medication screen is open, a new PD prescription and/or a new HD prescription may be entered for the patient.

Figure 76:
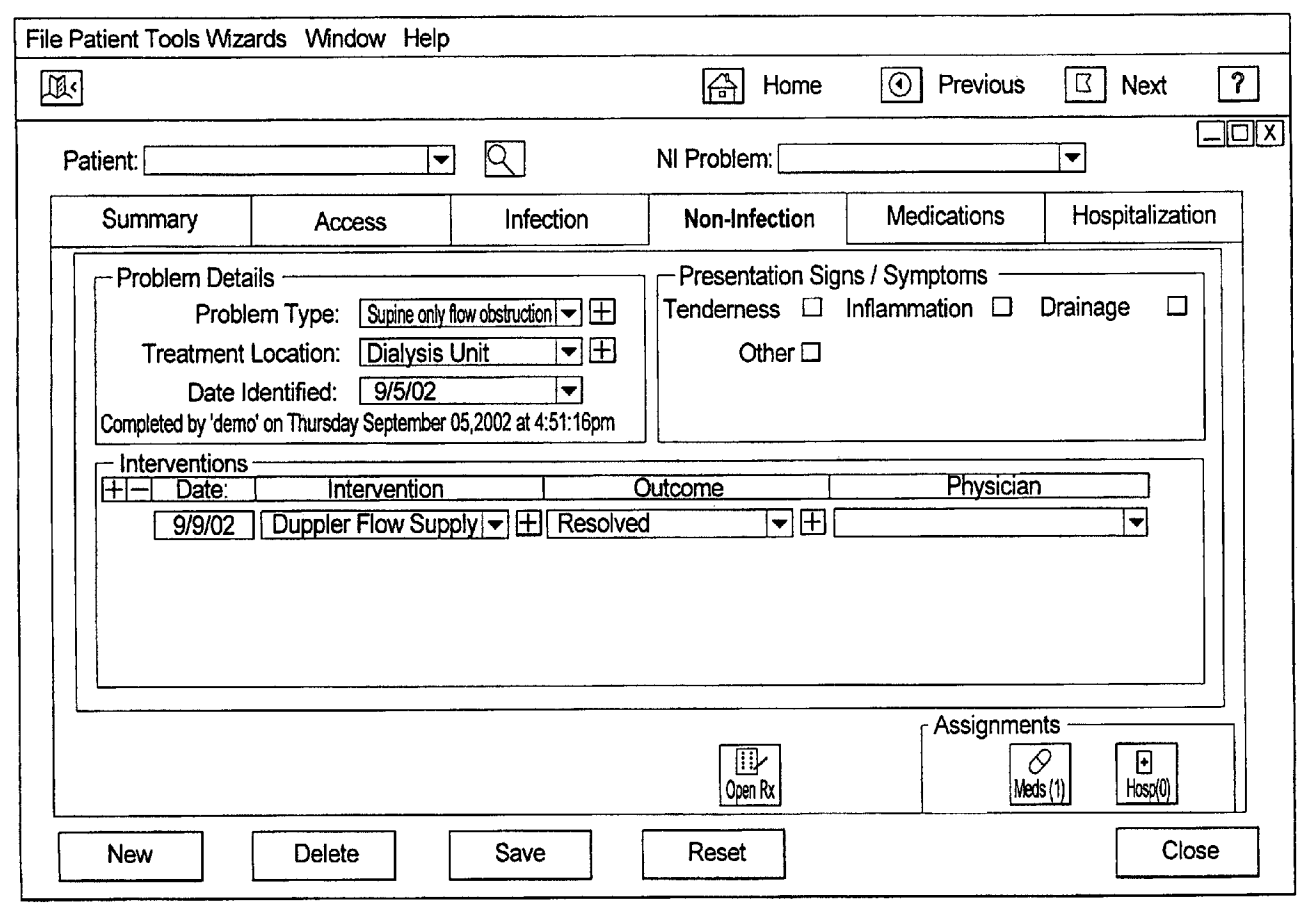

Referring now to FIG. 76, a non-infection tab screen is illustrated. The screen may display collected data on non-infection problems associated with the access of the patient. The non-infection problems associated with the access of the patient may be displayed on the screen in reverse chronological order. For example, the most recent non-infection access problem may be shown first. If non-infection data is saved in the system, medication prescription data associated with the non-infection problem may be displayed.

Figure 77:
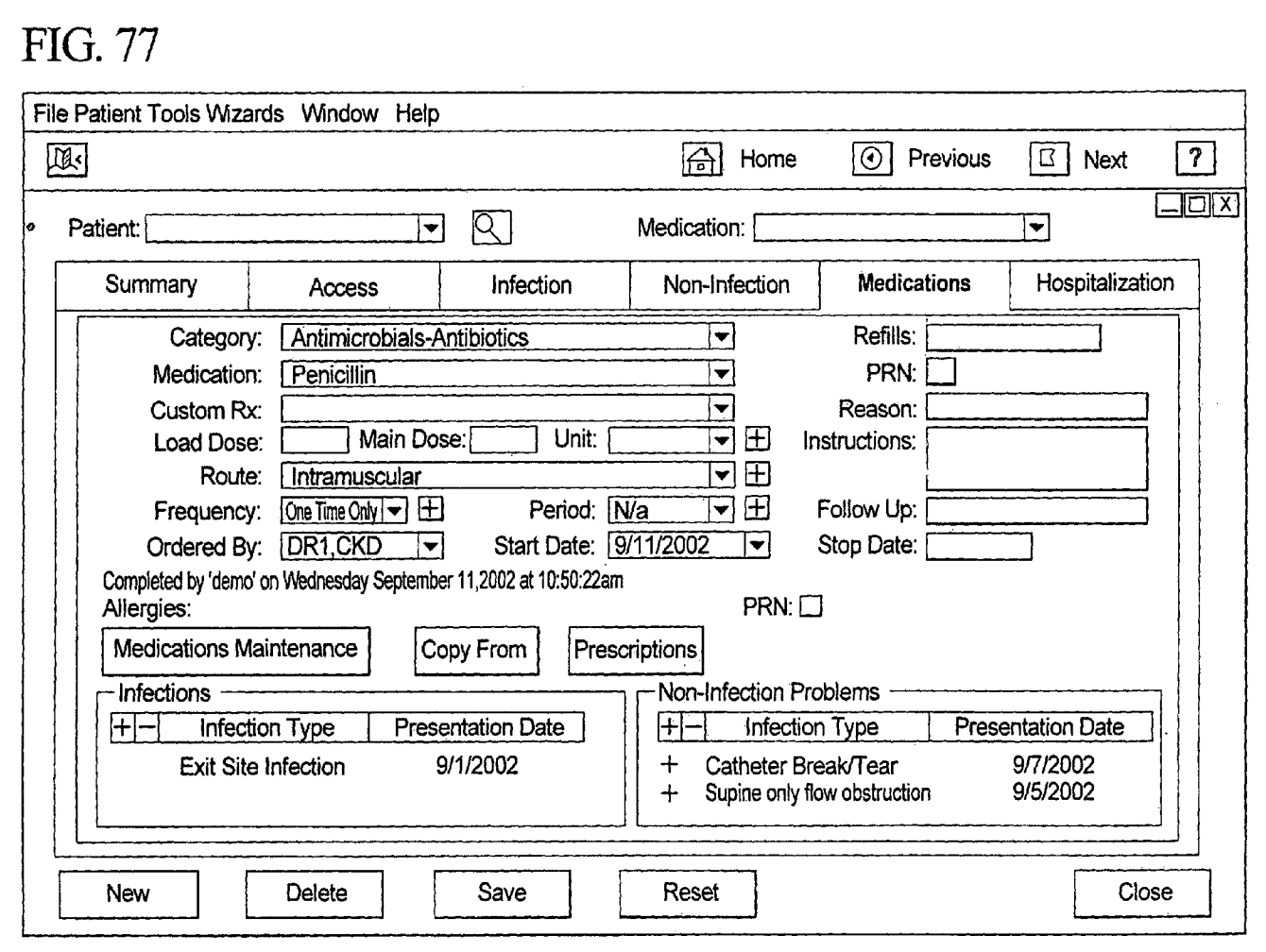

FIG. 77 illustrates a medication tab. The medication tab in the access window may allow a physician and/or a user to enter prescription data for medications that may be used to treat access infection problems and non-infection problems. The medication tab may display an association between the medication and the infection problems and/or the non-infection problems. Previously associated infection problems and/or non-infection problems may be displayed on the medication tab. A user may enter new prescription information into the medication tab. If a user returns to the infection or non-infection tab, the screens associated with the infection problems and/or the non-infection problems may display the new medications associated with the current infection.

Figure 78:
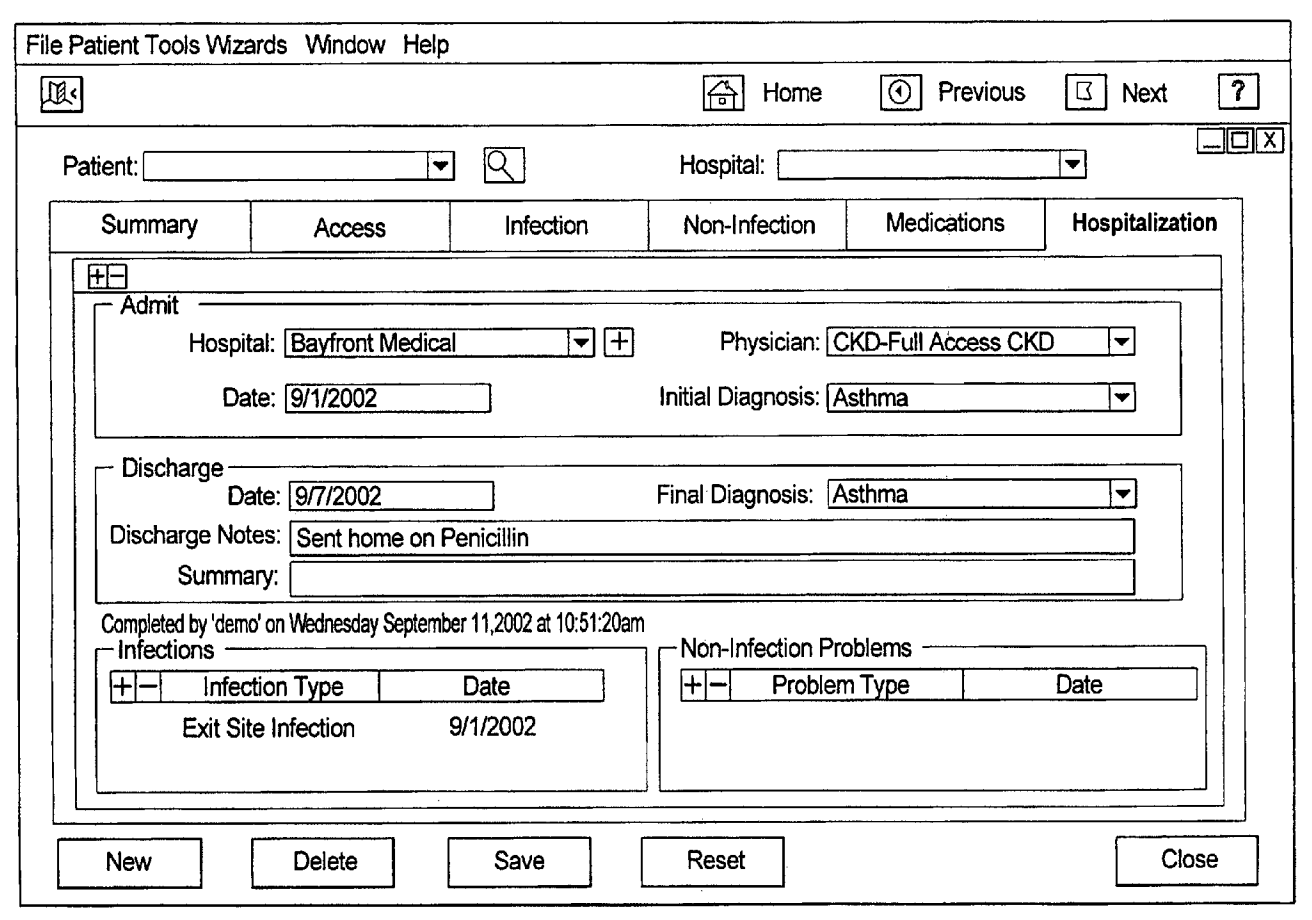

Referring now to FIG. 78, a hospitalization tab is illustrated allowing a user to enter and/or obtain hospital admission data for infection problems and non-infection problems relating to the care of the patient. The hospital tab may include hospitalization information, such as, for example, admission date, hospital location, physician, diagnosis, discharge date and/or discharge notes. The hospitalization tab may also identify the infection problems and/or the non-infection problems for the patient.

Figure 80:
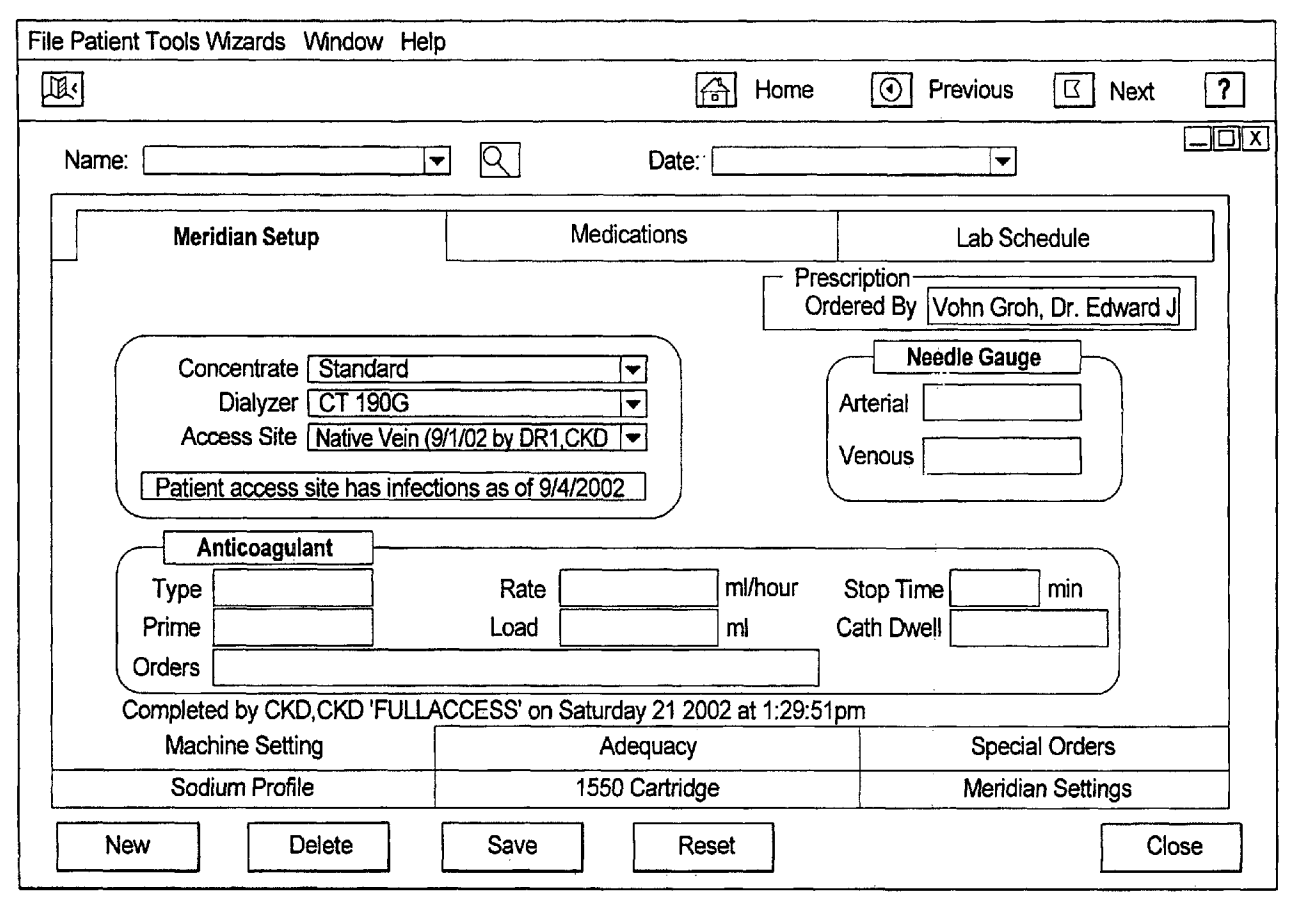

Referring to FIGS. 79-83, various screens relating to Chronic Kidney Disease (CKD) access planning are shown. FIG. 79 illustrates a CKD access planning screen which may be used to track and/or to manage the treatment of the patient. The CKD access planning screen may allow a user to input information to facilitate the planning of dialysis care for the patient. The planning screen may include, for example, access detail, access type, assessment dates, implantation details and the type of modality to be used in the treatment of the patient. Referring to FIG. 80, a screen associated with hemodialysis (HD) prescription may be provided. The HD prescription screen may provide information relating to the most recent access for a patient. The HD prescription screen may display, for example, medications prescribed to treat an infection problem and/or a non-infection problem, prescribing physician, medical devices used, and laboratory schedules for the patient.

FIG. 81 illustrates a hemodialysis treatment window. The HD treatment window may provide information relating to the treatment of an infection problem or a non-infection problem of the patient. The window may display, for example, treatment for a patient access, laboratory studies, dialyzer reuse, fluid work sheets, vital signs, physician and/or user observations, medications and a final sign off by the physician and/or user relating to the care of the patient undergoing hemodialysis.

Figure 82:
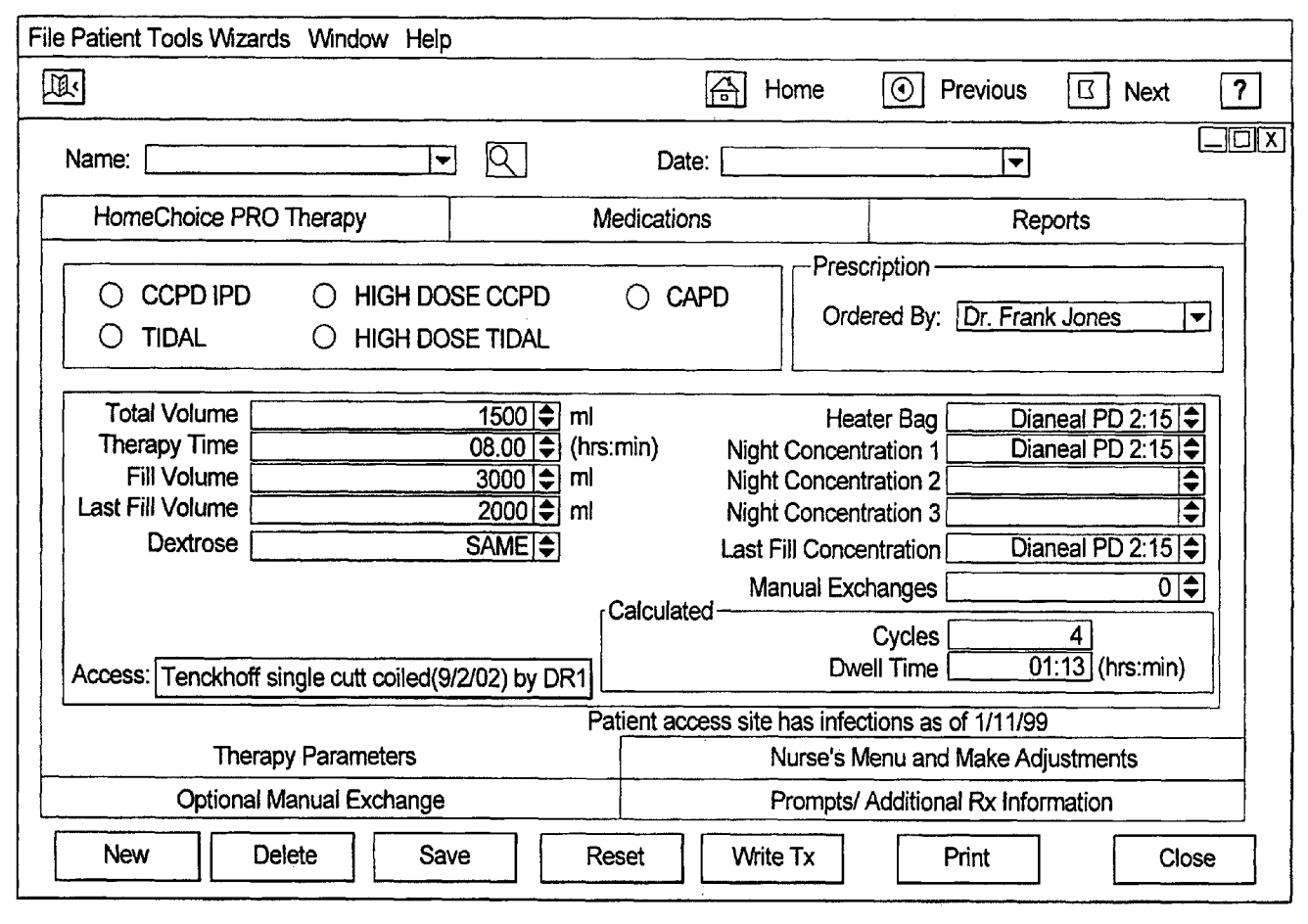

Referring now to FIG. 82, a PD prescription screen is illustrated. The PD prescription screen may display, for example, treatment progression, medications and reports on the treatment of the patient. A user may view a single PD access site or multiple PD access sites. The data may be stored in a table which may associate the medication to the access. The access may be modified at any time without impacting the prescription.

FIG. 83 illustrates a screen displaying PD compliance. Compliance factors for each date in a selected date range may be queried by a physician and/or user. The alert may be displayed on the screen if the compliance item is out of range.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

The invention is claimed as follows:

1. A method for monitoring patient compliance with a prescribed treatment for a patient undergoing a peritoneal dialysis therapy using a system including at least one display device, at least one memory device, at least one processor and at least one peritoneal dialysis instrument, the method comprising:

a peritoneal dialysis module organizing information for presentation at a first location in a plurality of screens using the at least one display device, the at least one memory device, and the at least one processor, wherein each screen presents information pertinent to a particular aspect of the peritoneal dialysis therapy;

the peritoneal dialysis module displaying in the plurality of screens at the first location (i) a peritoneal dialysis prescription screen for prescribing a treatment for the patient using the dialysis instrument and (ii) information about access to the peritoneal cavity of the patient;

prescribing a treatment for the patient using the peritoneal dialysis prescription screen, the dialysis instrument configured to remove ultrafiltration from the patient and deliver a volume of fluid to the patient based upon the prescribed treatment, the prescribed treatment including at least one of: (i) ultrafiltration to be removed by the dialysis instrument, (ii) total volume to be delivered by the dialysis instrument, or (iii) time of treatment to be performed by the dialysis instrument;

the at least one dialysis instrument performing at a first time the prescribed treatment on the patient at a second, different location;

recording results of performing the treatment at the second, different location, including results about at least one of: (a) ultrafiltration removed by the dialysis instrument, (b) total volume delivered by the dialysis instrument, (c) time of treatment performed by the dialysis instrument, (d) patient dry weight, (e) skipped treatments, or (f) a change in the prescribed treatment;

the peritoneal dialysis module displaying a compliance screen at the first location, wherein the compliance screen displays the recorded results, including at least one of (a) ultrafiltration removed by the dialysis instrument, (b) total volume delivered by the dialysis instrument, (c) time of treatment performed by the dialysis instrument, (d) patient dry weight, (e) skipped treatments, or (f) a change in the prescribed treatment, of performing the treatment at the second, different location; and the peritoneal dialysis module causing the at least one processor to compare the recorded results with an acceptable range for at least one of (a) to (f) and generate an alert at a second time after performing the prescribed treatment if the recorded results are outside the acceptable range.

2. The method of claim 1, which includes displaying the information about access to the peritoneal cavity of the patient at the prescription screen.

3. The method of claim 1, which includes displaying the information about access to the peritoneal cavity of the patient on an access implant detail screen at the first location.

4. The method of claim 3, which includes displaying at least one item of information selected from the group consisting of: physician, date, location, facility, facility type, first use, graft type and graft configuration on the access implant detail screen.

5. The method of claim 3, wherein if an implant has been removed, displaying at least one item of information selected from the group consisting of: a physician that removed the implant, a date the implant was removed, a location the implant was removed and a reason the implant was removed on the access implant detail screen.

6. The method of claim 1, which includes displaying the information about access to the peritoneal cavity of the patient on an access summary screen at the first location.

7. The method of claim 6, which includes displaying at least one item of information selected from the group consisting of: an implant date, an implant method, an implant location, an implant physician and a summary of patient problems sorted by infection problems and non-infection problems on the access summary screen.

8. A method for monitoring patient compliance with a prescription for a patient undergoing a peritoneal dialysis therapy under a system including at least one display device, at least one memory device, at least one processor and at least one peritoneal dialysis instrument for performing the peritoneal dialysis therapy, the method comprising:

organizing, via a peritoneal dialysis module, information for presentation in a plurality of screens using the at least one display device, the at least one memory device, and the at least one processor, wherein each screen presents information pertinent to a particular aspect of the peritoneal dialysis therapy;

the peritoneal dialysis module displaying in the plurality of screens information about the patient's prescription for the peritoneal dialysis therapy, the prescription including at least one of: (i) ultrafiltration to be removed by the dialysis instrument, (ii) total volume to be delivered by the dialysis instrument, or (iii) time of therapy to be performed by the dialysis instrument, information about medication the patient is taking in connection with the peritoneal dialysis therapy, and information about the patient's compliance with the prescription for the peritoneal dialysis therapy recorded by the dialysis instrument, the information about the patient's compliance including at least one of (a) ultrafiltration removed by the dialysis instrument, (b) total volume delivered by the dialysis instrument, (c) time of therapy performed by the dialysis instrument, (d) patient dry weight, (e) skipped therapies, or (f) a change in the prescription;

performing via the at least one dialysis instrument, the peritoneal dialysis therapy based on the prescription for the patient by removing ultrafiltration from the patient and delivering a volume of fluid to the patient, the prescription including at least one of: (i) ultrafiltration to be removed by the at least one dialysis instrument, (ii) total volume to be delivered by the at least one dialysis instrument, or (iii) time of treatment to be performed by the at least one dialysis instrument; and causing, via the peritoneal dialysis module, the at least one processor to compare the information about the patient's compliance with an acceptable range for at least one of (a) to (f) and generate an alert after performing the peritoneal dialysis therapy if the information about the patient's compliance is outside the acceptable range.

9. The method of claim 8, which further includes displaying in the plurality of screens information concerning the patient's peritoneal dialysis access site.

10. The method of claim 8, wherein displaying information about the patient's prescription for the peritoneal dialysis therapy includes displaying information about at least one of: (i) total volume, (ii) therapy time, (iii) fill volume, and (iv) last fill volume.

11. The method of claim 8, wherein displaying information about the patient's prescription for the peritoneal dialysis therapy includes displaying information about solution type used for the peritoneal dialysis therapy.

12. The method of claim 11, wherein information about solution type used for the peritoneal dialysis therapy includes information about at least one of solution brand and solution dextrose level.

13. The method of claim 8, wherein displaying information about the patient's prescription for the peritoneal dialysis therapy includes displaying information about peritoneal dialysis therapy type.

14. The method of claim 13, wherein the peritoneal dialysis therapy types are selected from the group consisting of: continuous circulating peritoneal dialysis ("CCPD"), tidal peritoneal dialysis, high dose CCPD, high dose tidal peritoneal dialysis, and continuous ambulatory peritoneal dialysis.

15. The method of claim 8, which includes displaying information about the patient's prescription on a first prescription screen and displaying information about the patient's compliance on a second compliance screen.

16. The method of claim 8, wherein information about the patient's compliance with the prescription for the peritoneal dialysis therapy includes information broken down by date.

17. The method of claim 8, wherein information about the patient's compliance with the prescription for the peritoneal dialysis therapy includes cross-referencing a plurality of dates with a plurality of compliance factors.

18. A method for monitoring patient compliance with a peritoneal dialysis therapy goal for a patient undergoing a peritoneal dialysis therapy using at least one display device, at least one memory device, at least one processor, and a peritoneal dialysis instrument for performing a prescribed peritoneal dialysis therapy, the method comprising:

a peritoneal dialysis module displaying information about the patient's prescribed peritoneal dialysis therapy type;

the peritoneal dialysis module displaying information about the patient's prescribed peritoneal dialysis therapy solution type;

the peritoneal dialysis module displaying information about the patient's prescribed peritoneal dialysis therapy solution volume;

the at least one processor calculating and the at least one display device displaying at least one peritoneal dialysis therapy parameter that is related to and based on the peritoneal dialysis therapy solution volume;

the peritoneal dialysis module displaying at least one peritoneal dialysis therapy goal;

the dialysis instrument performing the prescribed peritoneal dialysis therapy based on the peritoneal dialysis therapy goal by removing ultrafiltration from the patient and delivering a volume of fluid to the patient, the peritoneal dialysis therapy goal including at least one of (i) ultrafiltration to be removed by the dialysis instrument, (ii) total volume to be delivered by the dialysis instrument, or (iii) time of treatment to be performed by the dialysis instrument:

the peritoneal dialysis module indicating whether the at least one peritoneal dialysis goal has been met based upon peritoneal dialysis therapy results recorded by the dialysis instrument; and the peritoneal dialysis module causing the at least one processor to generate an alert after performing the peritoneal dialysis therapy if the at least one peritoneal dialysis goal has not been met.

19. The method of claim 18, wherein the at least one calculated peritoneal dialysis therapy parameter related to and based on the peritoneal dialysis therapy solution volume includes a number of therapy cycles or a dwell time.

20. The method of claim 18, wherein the at least one peritoneal dialysis therapy goal includes an ultrafiltration removed goal, a total volume delivered goal, a total time for therapy goal or a dry weight goal.

21. The method of claim 1, which includes causing the at least one processor to generate the alert after displaying the compliance screen.

22. The method of claim 1, which includes causing the at least one processor to generate the alert in response to a query.

23. The method of claim 8, which includes causing the at least one processor to generate the alert after displaying the information about the patient's compliance with the prescription for the peritoneal dialysis therapy.

24. The method of claim 8, which includes causing the at least one processor to generate the alert in response to a query.

25. The method of claim 18, which includes causing the at least one processor to generate the alert after indicating whether the at least one peritoneal dialysis goal has been met.

26. The method of claim 18, which includes causing the at least one processor to generate the alert in response to a query.

* * * * *